(12) United States Patent
Eggenweiler et al.

(10) Patent No.: US 7,312,328 B2
(45) Date of Patent: Dec. 25, 2007

(54) BENZOYLPYRIDAZINES

(75) Inventors: Hans-Michael Eggenweiler, Darmstadt (DE); Michael Wolf, Darmstadt (DE); Norbert Beier, Reinheim (DE); Joachim Leibrock, Pfungstadt (DE); Michael Gassen, Munich (DE); Thomas Ehring, Remscheid (DE)

(73) Assignee: Merck Patent GmbH, Darmstadt (DE)

( * ) Notice: Subject to any disclaimer, the term of this patent is extended or adjusted under 35 U.S.C. 154(b) by 487 days.

(21) Appl. No.: 10/451,393

(22) PCT Filed: Dec. 19, 2001

(86) PCT No.: PCT/EP01/15070

§ 371 (c)(1),
(2), (4) Date: Jun. 23, 2003

(87) PCT Pub. No.: WO02/051814

PCT Pub. Date: Jul. 4, 2002

(65) Prior Publication Data

US 2004/0067954 A1    Apr. 8, 2004

(30) Foreign Application Priority Data

Dec. 23, 2000  (DE) ................................ 100 64 997

(51) Int. Cl.
*A61K 31/50*   (2006.01)
*A61K 31/495*  (2006.01)

(52) U.S. Cl. ........................ 544/224; 514/247; 514/252

(58) Field of Classification Search ................. 544/224, 544/247, 252
See application file for complete search history.

(56) References Cited

U.S. PATENT DOCUMENTS 5,684,151 A * 11/1997 Combs ........................ 544/224
6,479,494 B1 * 11/2002 Rochus et al. ............... 514/247

FOREIGN PATENT DOCUMENTS

DE   19632549    2/1998
WO   WO 9401412  10/1994

OTHER PUBLICATIONS

Combs et al., "Nonsteroidal Progersterone Receptor Ligands . . . ", J. Med. Chem. 1995, 38, 4878-4879.*
Combs et al., "Nonsteroidal Progersterone Receptor Ligands . . . ", J. Med. Chem. 1995, 38, 4880-4884.*
D.W. Combs et al.; Nonsteroidal progesterone receptor ligands; Journal of Medicinal Chemistry vol. 38, No. 25, 1995, pp. 4878-4879, XP002047380.
D.W. Combs et al.; Nonsteroidal Progesterone Receptor Ligands 2; Journal of Medicinal Chemistry vol. 38, No. 25, 1995, pp. 4880-4884, XP002195498.

* cited by examiner

*Primary Examiner*—Johann R. Richter
*Assistant Examiner*—Paul V. Ward
(74) *Attorney, Agent, or Firm*—Millen, White, Zelano & Branigan, P.C.

(57) ABSTRACT

This invention relates to compounds of the formula (I) in which $R^1$, $R^2$, $R^3$, X and Q are as defined above and their use as PDE IV inhibitors.

11 Claims, No Drawings

BENZOYLPYRIDAZINES

The invention relates to compounds of the formula I

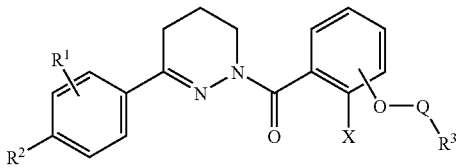

in which
R¹ and R² are each, independently of one another, H, OH, OR⁴, SR⁴, SOR⁴, SO₂R⁴ or Hal, where R¹ and R² together may alternatively be —O—CH₂—O—,
R³ is Hal, OH, OA, NO₂, NH₂, NHA¹, NA¹A², CN, COOH, COOA¹, CONH₂, CONHA¹, CONA¹A², NHCOA¹, NHSO₂A¹, NHCOOA¹,

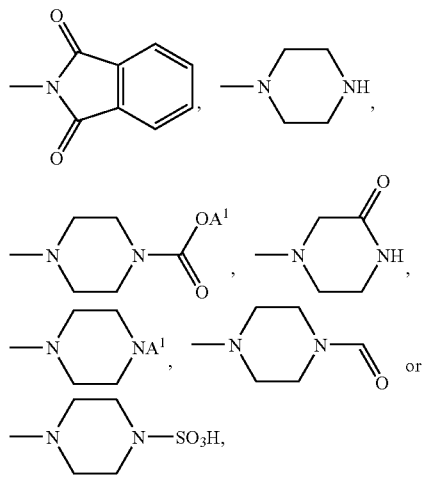

R⁴ is A¹, cycloalkyl having from 3 to 7 carbon atoms, alkylene-cycloalkyl having from 4 to 8 carbon atoms or alkenyl having from 2 to 8 carbon atoms,
A¹ and A² are each, independently of one another, alkyl having from 1 to 12 carbon atoms, which may be substituted by from 1 to 5 F and/or Cl atoms or OH-groups, where A¹ and A² together may alternatively be cycloalkyl or cycloalkylene having from 3 to 7 ring members, in which one or more CH₂ groups may be replaced by —S—, —O—, —NH—, —NA¹-, —NCOA¹- or —NCOOA¹-,
X is H or Hal,
Hal is F, Cl, Br or I, and
Q is alkyl or alkenyl having from 1 to 15 carbon atoms, in which from 1 to 5 —CH₂— groups may be replaced by —O—, —S—, —SO₂—, —CH(Hal)-, —C(Hal)₂—, —CHA¹-, —CA¹A²-, —NH— or —NA¹-,
and salts and solvates thereof.

1-Benzoyltetrahydropyridazines as progesterone receptor ligands are described, for example, in J. Med. Chem. 38, 4878 (1995). Similar compounds are also disclosed in DE 196 32 549 A1.

The invention had the object of finding novel compounds having valuable properties, in particular those which can be used for the preparation of medicaments.

It has been found that the compounds of the formula I and salts and solvates thereof have very valuable pharmacological properties as well as being well tolerated.

Compounds of formula I inhibit the PDE IV isozyme and thereby have a wide range of therapeutic applications, because of the essential role which the PDE IV family of isozymes plays in the physiology of all mammals. The enzymatic role performed by the PDE IV isozymes is the intracellular hydrolysis of adenosine 3',5'-monophosphate (cAMP) within pro-inflammatory leukocytes. cAMP, in turn, is responsible for mediating the effects of numerous hormones in the body, and as a consequence, PDE IV inhibition plays a significant role in a variety of physiological processes. There is extensive literature in the art describing the effects of PDE inhibitors on various inflammatory cell responses, which in addition to cAMP elevation, include inhibition of superoxide production, degranulation, chemotaxis and tumor necrosis factor (TNF) release in eosinophils, neutrophils and monocytes.

The compounds according to the invention can be employed for the treatment of asthmatic diseases. The antiasthmatic action of PDE IV inhibitors has been described, for example, by T. J. Torphy et al. in Thorax, 46, 512-523 (1991) and can be determined, for example, by the method of T. Olsson, Acta allergologica 26, 438-447 (1971).

Since cAMP inhibits bone-degrading cells and stimulates bone-forming cells (S. Kasugai et al., M 681 and K. Miyamoto, M 682, in Abstracts of the American Society for Bone and Mineral Research, 18th Annual Meeting, 1996), the compounds according to the invention can be employed for the treatment of osteoporosis.

The invention therefore furthermore relates to the use of the compounds of the formula I and/or physiologically acceptable salts and solvates thereof for the preparation of a medicament for the treatment and prophylaxis of diseases which are caused by an excessively low cAMP level and/or can be influenced by an increase in the cAMP level.

In addition, the compounds exhibit an antagonistic action to the production of TNF (tumour necrosis factor) and are therefore suitable for the treatment of allergic and inflammatory illnesses, autoimmune diseases and transplant rejection reactions. They can furthermore be employed for the treatment and prophylaxis of memory disorders, tumours, atherosclerosis, rheumatoid arthritis, multiple sclerosis, Crohn's disease, atopic dermatitis, diabetes mellitus, ulcerative colitis, cachexia, sepsis and AIDS.

The antiinflammatory action of the substances according to the invention and their efficacy for the treatment of, for example, autoimmune diseases, such as multiple sclerosis or rheumatoid arthritis, can be determined analogously to the methods of N. Sommer et al., Nature Medicine 1, 244-248 (1995) or L. Sekut et al., Clin. Exp. Immunol. 100, 126-132 (1995).

The compounds can be employed for the treatment of cachexia. The anti-cachectic action can be tested in TNF-dependent models of cachexia (P. Costelli et al., J. Clin. Invest. 95, 2367ff. (1995); J. M. Argiles et al., Med. Res. Rev. 17, 477ff. (1997)).

PDE IV inhibitors can also inhibit the growth of tumour cells and are therefore suitable for tumour therapy (D. Marko et al., Cell Biochem. Biophys. 28, 75ff. (1998)). The action of PDE IV inhibitors in the treatment of tumours is described, for example, in WO 95/35281, WO 95/17399 and WO 96/00215.

The invention therefore furthermore relates to the use of the compounds of the formula I and/or physiologically acceptable salts and solvates thereof for the preparation of a medicament for the treatment and prophylaxis of diseases which are caused by excessive production of tumour necrosis factor (TNF) and/or can be influenced by a reduction in the production of TNF.

PDE IV inhibitors can prevent mortality in models for sepsis and are therefore suitable for the therapy of sepsis (W. Fischer et al., Biochem. Pharmacol. 45, 2399ff. (1993)).

They can furthermore be employed for the treatment of memory disorders, atherosclerosis, atopic dermatitis and AIDS.

The action of PDE IV inhibitors in the treatment of asthma, inflammatory diseases, diabetes mellitus, atopic dermatitis, psoriasis, AIDS, cachexia, tumour growth or tumour metastases is described, for example, in EP 779 291.

The invention also relates to the use of the compounds of fomula I for the preparation of a medicament to treat myocardial diseases.

Coronary artery disease is the most common cause of death in the western world. In the presence of a critical stenosed coronary artery, a decrease of blood flow may result in myocardial ischemia. Initiation of reperfusion results, depending on the severity of the preceding ischemic period, in a reversibly or irreversibly injured myocardium, which is characterized by a long-lasting depression or an irreversible loss of contractile function. Depending on the size of the affected myocardial area, an acute or a chronic heart failure may develop.

A particular clinical problem in the above mentioned scenario is the development of restenosis after a primarily successful reperfusion intervention by PTCA, even after stent implantation, thrombolysis or coronary artery bypass grafting.

From experimental animal and clinical studies evidence exists, that in the different above mentioned heart diseases, i.e. coronary artery disease itself, reversible or irreversible myocardial ischemia/reperfusion injury, acute or chronic heart failure and restenosis, including instent-restenosis and stent-in-stent-restenosis, inflammatory processes play a casual role.

These inflammatory processes involve resident and invading macrophages as well as neutrophils and $TH_1$ and $TH_2$ helper cells. This leukocyte response produces the characteristic cytokine pattern, involving TNF-α, IL-1β, IL-2, and IL-6, as well as IL-10 and IL-13 (Pulkki K J: Cytokines and cardiomyocyte death. Ann. Med. 1997 29: 339-343.

Birks E J, Yacoub M H: The role of nitric oxide and cytokines in heart failure. Coron. Artery. Dis. 1997 8: 389-402).

The formation of these species has been demonstrated in human patients with myocardial ischemia. Animal models show that cytokine production correlates with the invasion of peripheral macrophages and neutrophils which can spread the damage into the still intact myocardium.

The main player in the cytokine response, however, is TNF-α, which integrates inflammatory and pro-apoptotic responses and additionally has a direct negative ionotropic effect on cardiac myocytes (Ceconi C, Curello S, Bachetti T, Corti A, Ferrari R: Tumor necrosis factor in congestive heart failure: a mechanism of disease for the new millennium? Prog. Cardiovasc. Dis. 1998 41: 25-30.

Mann DL: The effect of tumor necrosis factor-alpha on cardiac structure and function: a tale of two cytokines. J. Card. Fail. 1996 2: S165-S172. Squadrito F, Altavilla D, Zingarelli B, et al: Tumor necrosis factor involvement in myocardial ischaemia-reperfusion injury. Eur. J. Pharmacol. 1993 237: 223-230).

It has been shown in animal models of myocardial infarction, that TNF-α is rapidly released during the reperfusion phase (Herskowitz A, Choi S, Ansari A A, Wesselingh S: Cytokine mRNA expression in postischemic/reperfused myocardium. Am. J. Pathol. 1995 146: 419-428) and that the protective effects of drugs such as dexamethasone (Arras M, Strasser R, Mohri M, et al: Tumor necrosis factor-alpha is expressed by monocytes/macrophages following cardiac microembolization and is antagonized by cyclosporine. Basic. Res. Cardiol. 1998 93: 97-107), cyclosporin A (Arras M, Strasser R, Mohri M, et al: Tumor necrosis factor-alpha is expressed by monocytes/macrophages following cardiac microembolization and is antagonized by cyclosporine. Basic. Res. Cardiol. 1998 93: 97-107.

Squadrito F, Altavilla D, Squadrito G, et al: Cyclosporin-A reduces leukocyte accumulation and protects against myocardial ischaemia reperfusion injury in rats. Eur. J. Pharmacol. 1999 364: 159-168) or clorichromene (Squadrito F, Altavilla D, Zingarelli B, et al: The effect of cloricromene, a coumarine derivative, on leukocyte accumulation, myocardial necrosis and TNF-alpha production in myocardial ischaemia-reperfusion injury. Life Sci. 1993 53: 341-355) correspond with a reduction of circulating TNF-α.

Preferred compounds of formula I are potent antagonists of macrophage and T-cell cytokine production. They also inhibit the proliferation of T cells. Consequently, PDE IV inhibition may have a beneficial effect in those myocardial diseases, which are causally linked to cytokine production and inflammatory processes.

The invention also relates to the use of the compounds of the formula I and/or physiologically acceptable salts and solvates thereof for the preparation of a medicament for the treatment and prophylaxis of diseases which are caused by excessive production of macrophages and T-cells and/or can be influenced by a reduction in macrophage and T-cell production.

The invention also relates to the use of the compounds of the formula I and physiologically acceptable salts and/or solvates thereof for the preparation of a medicament for the treatment and prophylaxis of diseases which are caused by excessive proliferation of the T-cells and/or can be influenced by an inhibition of the proliferation of the T-cells.

As compared with PDE III inhibitors and the early PDE IV inhibitor Rolipram, the compounds of the present invention are devoid of hemodynamic side effects, which can be dose limiting for the treatment of most cardiovascular disorders.

Preferably, the invention provides for the use of the compounds of formula I for preparing a medicament in treating or preventing one or members selected from the groups of diseases, disorders, and conditions consisting of:

asthma of whatever type, etiology, or pathogenesis; or asthma that is a member selected from the group consisting of atopic asthma; non-atopic asthma; allergic asthma; atopic, bronchial, IgE-mediated asthma; bronchial asthma; essential asthma; true asthma; intrinsic asthma caused by pathophysiologic disturbances; extrinsic asthma caused by environmental factors; essential asthma of unknown or inapparent cause; non-atopic asthma; bronchitic asthma; emphysematous asthma; exercise-induced asthma; occupational asthma; infective asthma caused by bacterial, fungal, protozoal, or viral infection; non-allergic asthma; incipient asthma; wheezy infant syndrome;

chronic or acute bronchoconstriction; chronic bronchitis; small airways obstruction; and emphysema;

obstructive or inflammatory airways diseases of whatever type, etiology, or pathogenesis; or an obstructive or inflammatory airways disease that is a member selected from the group consisting of asthma; pneumoconiosis; chronic eosinophilic pneumonia; chronic obstructive pulmonary disease (COPD); COPD that includes chronic bronchitis, pulmonary emphysema or dyspnea associated therewith; COPD that is characterized by irreversible, progressive airways obstruction; adult respiratory distress syndrome (ARDS), and exacerbation of airways hyper-reactivity consequent to other drug therapy;

pneumoconiosis of whatever type, etiology, or pathogenesis; or pneumoconiosis that is a member selected from the group consisting of aluminosis or bauxite workers' disease; anthracosis or miners' asthma; asbestosis or steam-fitters' asthma; chalicosis or flint disease; ptilosis caused by inhaling the dust from ostrich feathers; siderosis caused by the inhalation of iron particles; silicosis or grinders' disease; byssinosis or cotton-dust asthma; and talc pneumoconiosis;

bronchitis of whatever type, etiology, or pathogenesis; or bronchitis that is a member selected from the group consisting of acute bronchitis; acute laryngotracheal bronchitis; arachidic bronchitis; catarrhal bronchitis; croupus bronchitis; dry bronchitis; infectious asthmatic bronchitis; productive bronchitis; staphylococcus or streptococcal bronchitis; and vesicular bronchitis;

bronchiectasis of whatever type, etiology, or pathogenesis; or bronchiectasis that is a member selected from the group consisting of cylindric bronchiectasis; sacculated bronchiectasis; fusiform bronchiectasis; capillary bronchiectasis; cystic bronchiectasis; dry bronchiectasis; and follicular bronchiectasis;

seasonal allergic rhinitis; or perennial allergic rhinitis; or sinusitis of whatever type, etiology, or pathogenesis; or sinuisitis that is a member selected from the group consisting of purulent or nonpurulent sinusitis; acute or chronic sinusitis; and ethmoid, frontal, maxillary, or sphenoid sinusitis, rheumatoid arthritis of whatever type, etiology, or pathogenesis; or rheumatoid arthritis that is a member selected from the group consisting of acute arthritis; acute gouty arthritis; chronic inflammatory arthritis; degenerative arthritis; infectious arthritis; Lyme arthritis; proliferative arthritis; psoriatic arthritis; and vertebral arthritis;

gout, and fever and pain associated with inflammation;

an eosinophil-related disorder of whatever type, etiology, or pathogenesis; or an eosinophil-related disorder that is a member selected from the group consisting of eosinophilia; pulmonary infiltration eosinophilia; Loffier's syndrome; chronic eosinophilic pneumonia; tropical pulmonary eosinophilia; bronchopneumonic aspergillosis; aspergilloma; granulomas containing eosinophils; allergic granulornatous angijtis' or Churg-Strauss syndrome; polyarteritis nodosa (PAN); and systemic necrotizing vasculitis;

atopic dermatitis; or allergic dermatitis; or allergic or atopic eczema;

urticaria of whatever type, etiology, or pathogenesis; or urticaria that is a member selected from the group consisting of immune-mediated urticaria; complement-mediated urticaria; urticariogenic material-induced urticaria; physical agent-induced urticaria; stressinduced urticaria; idiopathic urticaria; acute urticaria; chronic urticaria; angioedema; cholinergic urticaria; cold urticaria in the autosomal dominant form or in the acquired form; contact urticaria; giant urticaria; and papular urticaria;

conjunctivitis of whatever type, etiology, or pathogenesis; or conjunctivitis that is a member selected from the group consisting of actinic conjunctivitis; acute catarrhal conjunctivitis; acute contagious conjunctivitis; allergic conjunctivitis; atopic conjunctivitis; chronic catarrhal conjunctivitis; purulent conjunctivitis; and vernal conjunctivitis;

uveitis of whatever type, etiology, or pathogenesis; or uveitis that is a member selected from the group consisting of inflammation of all or part of the uvea; anterior uveitis; iritis; cyclitis; iridocyclitis; granulornatous uveitis; nongranulornatous uveitis; phacoantigenic uveitis; posterior uveitis; choroiditis; and chorioretinitis;

psoriasis;

multiple sclerosis of whatever type, etiology, or pathogenesis; or multiple sclerosis that is a member selected from the group consisting of primary progressive multiple sclerosis; and relapsing remitting multiple sclerosis;

autoimmune/inflammatory diseases of whatever type, etiology, or pathogenesis; or an autoimmune/inflammatory disease that is a member selected from the group consisting of autoimmune hematological disorders; hemolytic anemia; aplastic anemia; pure red cell anemia; idiopathic thrombocytopenic purpura; systemic lupus erythematosus; polychondritis; scleroderma; Wegner's granulomatosis; dermatomyositis; chronic active hepatitis; myasthenia gravis; Stevens-Johnson syndrome; idiopathic sprue; autoimmune inflammatory bowel diseases; ulcerative colitis; Crohn's disease; endocrin opthamopathy; Grave's disease; sarcoidosis; alveolitis; chronic hypersensitivity pneumonitis; primary biliary cirrhosis; juvenile diabetes or diabetes mellitus type 1; anterior uveitis; granulornatous or posterior uveitis; keratoconjunctivitis sicca; epidemic keratoconjunctivitis; diffuse interstitial pulmonary fibrosis or interstitial lung fibrosis; idiopathic pulmonary fibrosis; cystic fibrosis; psoriatic arthritis; glomerulonephritis with and without nephrotic syndrome; acute glomerulonephritis; idiopathic nephrotic syndrome; minimal change nephropathy; inflammatory/hyperproliferative skin diseases; psoriasis; atopic dermatitis; contact dermatitis; allergic contact dermatitis; benign familial pemphigus; pemphigus erythematosus; pemphigus foliaceus; and pemphigus vulgaris;

prevention of allogeneic graft rejection following organ transplantation;

inflammatory bowel disease (IBD) of whatever type, etiology, or pathogenesis; or inflammatory bowel disease that is a member selected from the group consisting of ulerative colitis (UC); collagenous colitis; colitis polyposa; transmural colitis; and Crohn's disease (CD);

septic shock of whatever type, etiology, or pathogenesis; or septic shock that is a member selected from the group consisting of renal failure; acute renal failure; cachexia; malarial cachexia; hypophysial cachexia; uremic cachexia; cardiac cachexia; cachexia suprarenalis or Addison's disease; cancerous cachexia; and cachexia as a consequence of infection by the human immunodeficiency virus (HIV);

liver injury;

pulmonary hypertension; and hypoxia-induced pulmonary hypertension;

bone loss diseases; primary osteoporosis; and secondary osteoporosis;

central nervous system disorders of whatever type, etiology, or pathogenesis; or a central nervous system disorder that is a member selected from the group consisting of depression; Parkinson's disease; learning and memory impairment; tardive dyskinesia; drug. dependence; arteriosclerotic dementia; and dementias that accompany Huntington's chorea, Wilson's disease, paralysis agitans, and thalamic atrophies;

infection, especially infection by viruses wherein such viruses increase the production of TNF-α in their host, or wherein such viruses are sensitive to upregulation of TNF-α in their host so that their replication or other vital activities are adversely impacted, including a virus which is a member selected from the group consisting of HIV-1, HIV-2, and HIV-3; cytornegalovirus, CMV; influenza; adenoviruses; and Herpes viruses, including Herpes zoster and Herpes simplex;

yeast and fungus infections wherein said yeast and fungi are sensitive to upregulation by TNF-α or elicit TNF-α production in their host, e.g., fungal meningitis; particularly when administered in conjunction with other drugs of choice for the treatment of systemic yeast and fungus infections, including but are not limited to, polymixins, e.g., Polymycin B; imidazoles, e.g., clotrimazole, econazole, miconazole, and ketoconazole; triazoles, e.g., fluconazole and itranazole; and amphotericins, e.g., Amphotericin B and liposomal Amphotericin B;

ischemia-reperfusion injury; autoimmune diabetes; retinal autoimmunity; chronic lymphocytic leukemia; HIV infections; lupus erythematosus; kidney and ureter disease; urogenital and gastrointestinal disorders; and prostate diseases.

In particular, compounds of formula I are useful in the treatment of (1) inflammatory diseases and conditions comprising: joint inflammation, rheumatoid arthritis, rheumatoid spondylitis, osteoarthritis, inflammatory bowel disease, ulcerative colitis, chronic glomerulonephritis, dermatitis, and Crohn's disease; (2) respiratory diseases and conditions comprising: asthma, acute respiratory distress syndrome, chronic pulmonary inflammatory disease, bronchitis, chronic obstructive airway disease, and silicosis; (3) infectious diseases and conditions comprising: sepsis, septic shock, endotoxic shock, gram negative, sepsis, toxic shock syndrome, fever and myalgias due to bacterial, viral or fungal infection, and influenza; (4) immune diseases and conditions comprising: autoimmune diabetes, systemic lupus erythematosis, graft vs. host reaction, allograft rejections, multiple sclerosis, psoriasis, and allergic rhinitis; and (5) other diseases and conditions comprising: bone resorption diseases; reperfusion injury; cachexia secondary to infection or malignancy; cachexia secondary to human acquired immune deficiency syndrome (AIDS), human immuno-deficiency virus (HIV) infection, or AIDS related complex (ARC); keloid formation; scar tissue formation; type 1 diabetes mellitus; and leukemia.

The present invention further relates to the combination of a preferred compound of Formula I mentioned above together with one or more members selected from the group consisting of the following: (a) leukotriene biosynthesis inhibitors: 5-lipoxygenase (5-LO) inhibitors and 5-lipoxygenase activating protein (FLAP) antagonists selected from the group consisting of zileuton; fenleuton; tepoxalin; Abbott-79175; Abbott-85761; N-(5-substituted) thiophene-2-alkylsulfonamides; 2,6-di-tert-butylphenol hydrazones; the class of methoxytetrahydropyrans which includes Zeneca ZD-2138; the compound SB-210661 and the class to which it belongs; the class of pyridinyl-substituted 2-cyanonaphthafene compounds to which L 739,010 belongs; the class of 2-cyanoquinoline compounds to which L-746,530 belongs; the classes of indole and quinoline compounds to which MK-591, MK-886, and BAY x 1005 belong; (b) receptor antagonists for leukotrienes LTB4, LTC4, LTD4, and LTE4 selected from the group consisting of the phenothiazin-3-one class of compounds to which L-651,392 belongs; the class of amidino compounds to which CGS-25019c belongs; the class of benzoxaolamines to which ontazolast belongs; the class of benzenecarboximidamides to which BIIL 284/260 belongs; and the classes of ompounds to which zafirlukast, ablukast, montelukast, pranlukast, verlukast (MK-679), RG-12525, Ro-245913, iralukast (CGP 45715A), and BAY x 7195 belong; (c) PDE IV inhibitors; (d) 5-Lipoxygenase (5-1-0) inhibitors; or 5-lipoxygenase activating protein (FLAP) antagonists; (e) dual inhibitors of 5-lipoxygenase (5-LO) and antagonists of platelet activating factor (PAF); (f) leukotriene antagonists (LTRAs) including antagonists of LTB4, LTC4, LTD4, and LTE4; (g) antihistaminic H, receptor antagonists including cetirizine, loratadine, desioratadine, fexofenadine, astemizole, azelastine, and chlorpheniramine; (h) gastroprotective H2 receptor antagonists; (i) $\alpha_1$- and $\alpha_2$-adrenoceptor agonist vasoconstrictor sympathomimetic agents administered orally or topically for decongestant use, including propyl hexedrine, phenylephrine, phenylpropanolamine, pseudoephedrine, naphazoline hydrochloride, oxymetazoline hydrochloride, tetrahydrozoline hydrochloride, xylometazoline hydrochloride, and ethylnorepinephrine hydrochloride; j) $\alpha_1$- and $\alpha_2$-adrenoceptor agonists in combination with inhibitors of 5-lipoxygenase (5-LO); (k) anticholinergic agents including ipratropium bromide; tiotropiurn bromide; oxitropium bromide; pirenzepine; and telenzepine; (l) $\beta_1$- to $\beta_4$ adrenoceptor agonists including etaproterenol, isoproterenol, isoprenaline, albuterol, salbutamol, formoterol, salmeterol, terbutaline, orciprenaline, bitolterol mesylate, and pirbuterol; (m) methylxanthanines including theophylline and aminophylline; (n) sodium cromoglycate; (o) muscarinic receptor (M1, M2, and M3) antagonists; (p) COX-1 inhibitors (NSAIDs); COX-2 selective inhibitors including rofecoxib; and nitric oxide NSAIDs; (q) insulin-like growth factor type 1 (IGF-1) mimetics; (r) ciclesonide; (s) inhaled glucocorticoids with reduced systemic side effects, including prednisone, prednisolone, flunisolide, triamcinolone acetonide, beclomethasone dipropionate, budesonide, fluticasone propionate, and mometasone furoate; (t) tryptase inhibitors; (u) platelet activating factor (PAF) antagonists; (v) monoclonal antibodies active against endogenous inflammatory entities; (w) IPL 576; (x) antitumor necrosis factor (TNFα) agents including Etanercept, Infliximab, and D2E7; (y) DMARDs including Leflunomide; (z) TCR peptides; (aa) interleukin converting enzyme (ICE) inhibitors; (bb) IMPDH inhibitors; (cc) adhesion molecule inhibitors including VLA-4 antagonists; (dd) cathepsins; (ee) MAP kinase Inhibitors; (ff) glucose-6 phosphate dehydrogenase inhibitors; (gg) kinin-131- and B2-receptor antagonists; (hh) gold in the form of an aurothio group together with various hydrophilic groups; (ii) immuno-suppressive agents, e.g., cyclosporine, azathioprine, and methotrexate; (jj) anti-gout agents, e.g., colchicine; (kk) xanthine oxidase inhibitors, e.g., allopurinol; (ll) uricosuric agents, e.g., probenecid, sulfinpyrazone, and benzbromarone; (mm) antineoplastic agents, especially antimitotic drugs including the vinca alkaloids such as vinblastine and vincristine; (nn) growth hormone secretagogues; (oo) inhibitors of matrix metalloproteases (MMPs), i.e., the stromelysins, the collagenases, and the gelatinases, as well as aggrecanase; especially collagenase-1 (MMP-1), collagenase-2 (MMP-8), collagenase-3 (MMP-13), stromelysin-1 (MMP-3), stromelysin-2 (MMP-10), and stromelysin-3 (MMP-11); (pp) transforming growth factor (TGFP); (qq) platelet-derived growth factor (PDGF); (rr) fibroblast growth factor, e.g., basic fibroblast growth factor (bFGF); (ss) granulocyte macrophage colony stimulating factor (GM-CSF); (tt) capsaicin; (uu) Tachykinin $NK_1$ and $NK_3$ receptor antagonists selected from the group consisting of NKP-608C; SB233412 (talnetant); and D-4418; and (vv) elastase inhibitors selected from the group consisting of UT-77 and ZD-0892.

The present invention also relates to a combination of one or more compounds of formula I together with one or more additional therapeutic agents to be co-administered to a patient to obtain some particularly desired therapeutic end result. The second, etc. therapeutic agent may also be one or more compounds as described above or one or more PDE IV inhibitors known in the art and described in detail herein. More typically, the second, etc. therapeutic agent will be selected from a different class of therapeutic agents. These selections are described in detail below.

As used herein, the terms co-administration", "co-administered", and "in combination with", referring to the preferred compounds as mentioned above and one or more other therapeutic agents, is intended to mean, and does refer to and include the following:

(a) simultaneous administration of such combination of compound(s) and therapeutic agent(s) to a patient in need of treatment, when such components are formulated together into a single dosage form which releases said components at substantially the same time to said patient;

(b) substantially simultaneous administration of such combination of compound(s) and therapeutic agent(s) to a patient in need of treatment, when such components are formulated apart from each other into separate dosage forms which are ingested at substantially the same time by said patient, whereupon said components are released at substantially the same time to said patient;

(c) sequential administration of such combination of compound(s) and therapeutic agent(s) to a patient in need of treatment, when such components are formulated apart from each other into separate dosage forms which are ingested at consecutive times by said patient with a significant time interval between each ingestion, whereupon said components are released at substantially different times to said patient; and (d) sequential administration of such combination of compound(s) and therapeutic agent(s) to a patient in need of treatment, when such components are formulated together into a single dosage form which releases said components in a controlled manner whereupon they are concurrently, consecutively, and/or overlappingly ingested at the same and/or different times by said patient.

One or more of the compounds of fomula I can also be used in combination with leukotriene biosynthesis inhibitors, i.e., 5-lipoxygenase inhibitors and/or 5-lipoxygenase activating protein antagonists, to form embodiments of the present invention. 5-Lipoxygenase (5-LO) is one of two groups of enzymes that metabolize arachidonic acid, the other group being the cyclooxygenases, COX-1 and COX-2.

The 5-lipoxygenase activating protein is an 18 kDa membrane-bound, arachidonate-binding protein which stimulates the conversion of cellular arachidonic acid by 5-lipoxygenase. The arachidonic acid is converted into 5-hydroperoxyeicosatetraenoic acid (5-HPETE), and this pathway eventually leads to the production of inflammatory leukotrienes; consequently, blocking the 5-lipoxygenase activating protein or the 5-lipoxygenase enzyme itself provides a desirable target for beneficially interfering with that pathway. One such 5-lipoxygenase inhibitor is zileuton. Among the classes of leukotriene synthesis inhibitors which are useful for forming therapeutic combinations with the compounds of formula I are the following:

(a) redox-active agents which include N-hydroxyureas; N-alkylhydroxamid acids; selenite; hydroxybenzofurans; hydroxylamines; and catechols; see Ford-Hutchinson et aL, "5-Lipoxygenase," Ann. Rev. Biochem. 63, 383-417, 1994; Weitzel and Wendel, "Selenoenzymes regulate the activity of leukocyte 5-lipoxygenase via the peroxide tone," J. Biol. Chem. 268, 6288-92, 1993; Björnstedt et al. "Selenite incubated with NADPH and mammalian thioredoxin reductase yields selenide, which inhibits lipoxygenase and changes the electron spin resonance spectrum of the active site iron," Biochemistry 35, 8511-6, 1996; and Stewart et al., "Structure-activity relationships of N-hydroxyurea 5-lipoxygenase inhibitors," J. Med. Chem. 40, 1955-68, 1997;

(b) alkylating agents and compounds which react with SH groups have been found to inhibit leukotriene synthesis in vitro; see Larsson et al., "Effects of 1-chloro-2,4,6trinitrobenzene on 5-lipoxygenase activity and cellular leukotriene synthesis," Biochem. Pharmacol. 55, 863-71, 1998; and (c) competitive inhibitors of 5-lipoxygenase, based on thiopyranoindole and methoxyalkyl thiazole structures which may act as non-redox inhibitors of 5-lipoxygenase; see Ford-Hutchinson et al., Ibid.; and Hamel et al., "Substituted (pyridylmethoxy)naphthalenes as potent and orally active 5-lipoxygenase inhibitors—synthesis, biological profile, and pharmacokinetics of L-739,010," J. Med. Chem. 40, 2866-75, 1997.

The observation that arachidonoyl hydroxyamate inhibits 5-lipoxygenase has led to the discovery of clinically useful selective 5-lipoxygenase inhibitors such as the N-hydroxyurea derivatives zileuton and Abbott-85761, represented below:

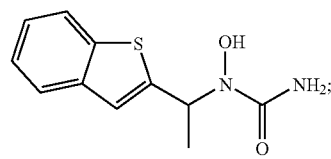

Zileuton

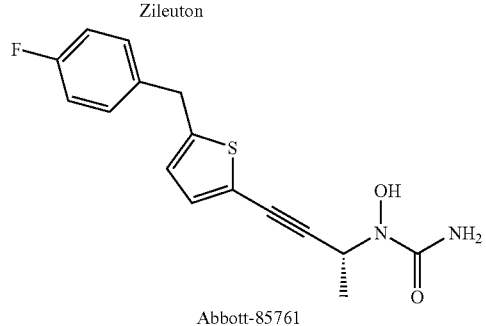

Abbott-85761

Another N-hydroxyurea compound is fenleuton (Abbott-76745):

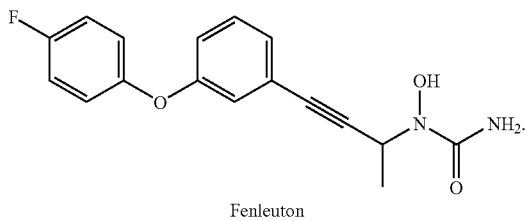

Fenleuton

Another N-hydroxyurea compound is Abbott-79175

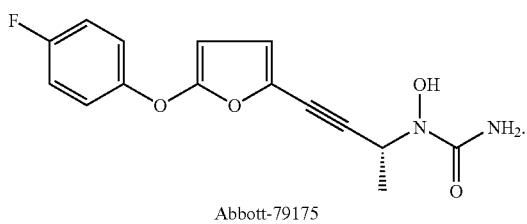

Abbott-79175

Abbott-79175 has a longer duration of action than zileuton; Brooks et al, J. Pharm. Exp. Therapeut 272 724, 1995.

Abbott-85761 is delivered to the lung by aerosol administration of a homogeneous, physically stable and nearly monodispersed formulation; Gupta et al., "Pulmonary delivery of the 5-lipoxygenase inhibitor, Abbott-85761, in beagle dogs," International Journal of Pharmaceutics 147, 207-218, 1997.

Fenleuton, Abbott-79175, Abbott-85761 or any of the above-described derivatives thereof or of tepoxalin, are combined with the preferred compounds described above to form embodiments of the present invention.

Since the elucidation of the 5-LO biosynthetic pathway, there has been an ongoing debate as to whether it is more advantageous to inhibit the 5-lipoxygenase enzyme or to antagonize peptido- or non-peptido leukotriene receptors. Inhibitors of 5-lipoxygenase are deemed to be superior to LT-receptor antagonists, since 5-lipoxygenase inhibitors block the action of the full spectrum of 5-LO products, whereas LT-antagonists produce narrower effects. Nevertheless, embodiments of the present invention include combinations of the preferred compounds with LT-antagonists as well as 5-LO inhibitors, as described below. Inhibitors of 5-lipoxygenase having chemical structures that differ from the classes of N-hydroxyureas and hydroxamic acids described above are also used in combination with the preferred compounds to form further embodiments of the present invention. An example of such a different class is the N-(5-substituted)-thiophene-2-alkylsulfonamides of following formula

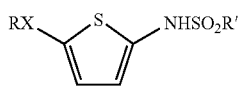

where X is O or S; R' is methyl, iso-propyl, n-butyl, n-octyl, or phenyl; and R is n-pentyl, cyclohexyl, phenyl, tetrahydro-1-naphthyl, 1- or 2-naphthyl, or phenyl mono- or di-substi-tuted by Cl, F, Br, $CH_3$, $OCH_3$, $SCH_3$, $SO_2CH_3$, $CF_3$, or iso-propyl. A preferred compound is

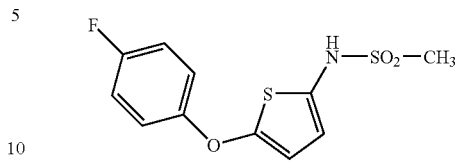

A further description of these compounds may be found in Beers et al., "N-(5-substituted) thiophene-2-alkylsulfonamides as potent inhibitors of 5-lipoxygenase," Bioorganic & Medicinal Chemistry 5(4), 779-786, 1997.

Another distinct class of 5-lipoxygenase inhibitors is that of the 2,6-di-tert-butylphenol hydrazones described in Cuadro et al., "Synthesis and biological evaluation of 2,6-di-tert.-butylphenol hydrazones as 5-lipoxygenase inhibitors," Bioorganic & Medicinal Chemistry 6, 173-180, 1998. Compounds of this type are represented by

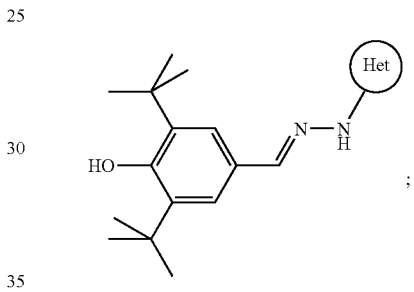

where "Het" is benzoxazol-2-yl; benzothiazol-2-yl; pyridin-2-yl; pyrazin-2-yl; pyrimidin-2-yl; 4-phenylpyrimidin-2-yl; 4,6-diphenylpyrimidin-2-yl; 4-methylpyrimidin-2-yl; 4,6-dimethylpyrimidin-2-yl; 4-butylpyrimidin-2-yl; 4,6-dibutylpyrimidin-2-yl; and 4-methyl-6-phenylpyrimidin-2-yl.

The N-(5-substituted)-thiophene-2-alkylsulfonamides or the 2,6-di-tert-butylphenol hydrazones or any of the above-described derivatives thereof, are combined with the preferred compounds mentioned above to form embodiments of the present invention.

A further distinct class of 5-lipoxygenase inhibitors is that of methoxytetrahydropyrans to which Zeneca ZD-2138 belongs

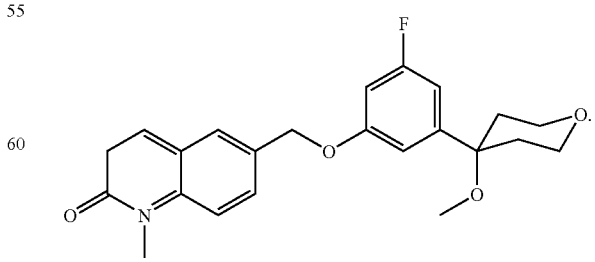

ZD-2138

ZD-2138 is highly selective and highly active orally in a number of species and has been evaluated in the treatment of asthma and rheumatoid arthritis by oral admininstration. Further details concerning ZD-2138 and derivatives thereof are disclosed in Crawley et al., J. Med. Chem., 35, 2600, 1992; and Crawley et al., J. Med. Chem. 36, 295, 1993.

Another distinct class of 5-lipoxygenase inhibitors is that to which the SmithKline Beecham compound SB-210661 belongs

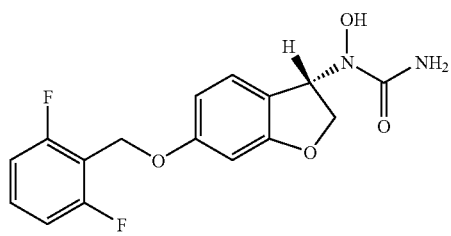

Two further distinct and related classes of 5-lipoxygenase inhibitors comprise a series of pyridinyl-substituted 2-cyanonaphthalene compounds and a series of 2-cyanoquinoline compounds discovered by Merck Frosst. These two classes of 5-lipoxygenase inhibitors are exemplified by L-739,010 and L-746,530, respectively:

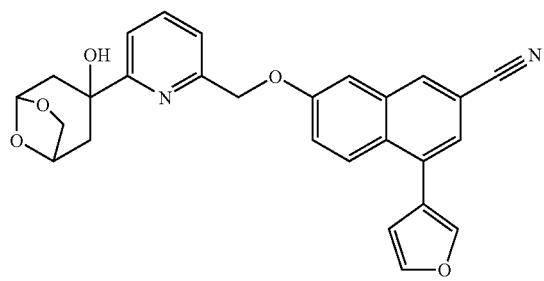

L-739,010

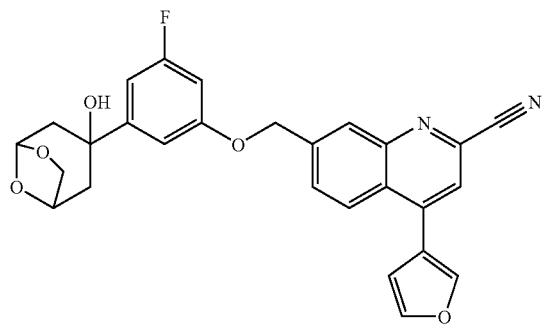

L-746,530

Details concerning L-739,010 and L-746,530 are disclosed in Dubé et al., "Quinolines as potent 5-lipoxygenase inhibitors: synthesis and biological profile of L-746,530," Bioorganic & Medicinal Chemistry 8, 1255-1260, 1998; and in WO 95/03309 (Friesen et al.).

The class of methoxytetrahydropyrans including Zeneca ZD-2138; or the lead compound SB-210661 and the class to which it belongs; or the series of pyridinyl-substituted 2-cyanonaphthalene compounds to which L-739,010 belongs, or the series of 2-cyanoquinoline compounds to which L-746,530 belongs; or any of the above-described derivatives of any of the above-mentioned classes, are combined with the preferred compounds mentioned above to form embodiments of the present invention.

In addition to the 5-lipoxygenase enzyme, the other endogenous agent which plays a significant role in the biosynthesis of the leukotrienes is the 5-lipoxygenase activating protein (FLAP). This role is an indirect one, in contrast to the direct role of the 5-lipoxygenase enzyme. Nevertheless, antagonists of the 5-lipoxygenase activating protein are employed to inhibit the cellular synthesis of leukotrienes, and as such are also used in combination with the preferred compounds mentioned above to form embodiments of the present invention.

Compounds which bind to the 5-lipoxygenase activating protein and thereby block utilization of the endogenous pool of archidonic acid which is present have been synthesized from indole and quinoline structures; see Ford-Hutchinson et al., Ibid.; Rouzer et al. "WK-886, a potent and specific leukotriene biosynthesis inhibitor blocks and reverses the membrane association of 5-lipoxygenase in ionophore-challenged leukocytes," J. Biol. Chem. 265, 1436-42, 1990; and Gorenne et al., "{(R)-2-quinolin-2-yl-methoxy)phenyl)-2-cyclopentyl acetic acid} (BAY x 1005), a potent leukotriene synthesis inhibitor: effects on anti-IgE challenge in human airways," J. Pharmacol. Exp. Ther. 268, 868-72, 1994.

MK-591, which has been designated quiflipon sodium, is represented below

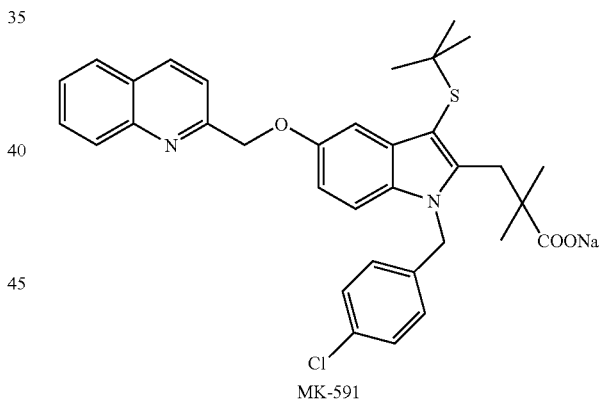

MK-591

The above-mentioned indole and quinoline classes of compounds and the specific compounds MK-591, MK-886, and BAY x 1005 to which they belong, or any of the above-described derivatives of any of the above-mentioned classes, are combined with the preferred compounds mentioned above to form embodiments of the present invention.

One or more of the compounds of formula can also be used in combination with receptor antagonists for leukotrienes $LTB_4$, $LTC_4$, $LTD_4$, and $LTE_4$. The most significant of these leukotrienes in terms of mediating inflammatory response, are $LTB_4$ and $LTD_4$. Classes of antagonists for the receptors of these leukotrienes are described in the paragraphs which follow.

4-Bromo-2,7-dimethoxy-3H-phenothiazin-3-ones, including L-651,392, are potent receptor antagonists for LTB$_4$ that are described in U.S. Pat. No. 4,939,145 (Guindon et al.) and U.S. Pat. No. 4,845,083 (Lau et al.)

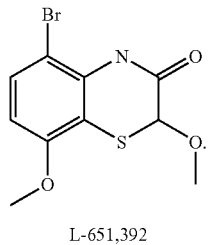

L-651,392

A class of amidino compounds that includes CGS-25019c is described in U.S. Pat. No. 5,451,700 (Morrissey and Suh); U.S. Pat. No. 5,488,160 (Morrissey); and U.S. Pat. No. 5,639,768 (Morrissey and Suh). These receptor antagonists for LTB$_4$ are typified by CGS-25019c, which is represented below:

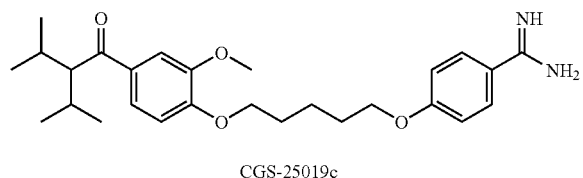

CGS-25019c

Ontazolast, a member of a class of benzoxaolamines that are receptor antagonists for LTB$_4$, is described in EP 535 521 (Anderskewitz et A):

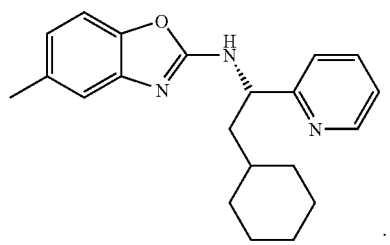

Ontozolast

The same group of workers has also discovered a class of benzenecarboximidamides which are receptor antagonists for LTB$_4$, described in WO 97/21670 (Anderskewitz et al.); and WO 98/11119 (Anderskewitz et I.); and which are typified by BIIL 284/260:

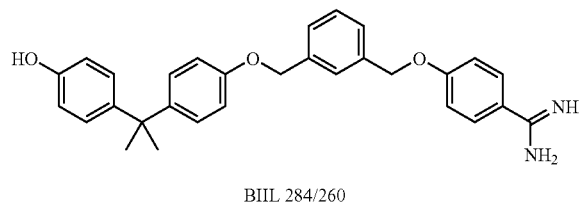

BIIL 284/260

Zafirlukast is a receptor antagonist for LTC$_4$, LTD$_4$, and LTE$_4$ which is sold commercially under the name Acco-late®. It belongs to a class of heterocyclic amide derivatives described in U.S. Pat. No. 4,859,692 (Bernstein et al.); U.S. Pat. No. 5,319,097 (Holohan and Edwards); U.S. Pat. No. 5,294,636 (Edwards and Sherwood); U.S. Pat. No. 5,482,963; U.S. Pat. No. 5,583,152 (Bernstein et al.); and U.S. Pat. No. 5,612,367 (Timko et al.):

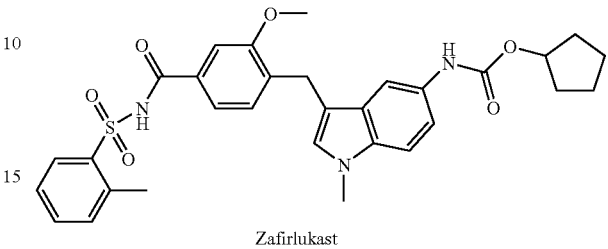

Zafirlukast

Ablukast is a receptor antagonist for LTD$_4$ that is designated Ro 23-3544/001:

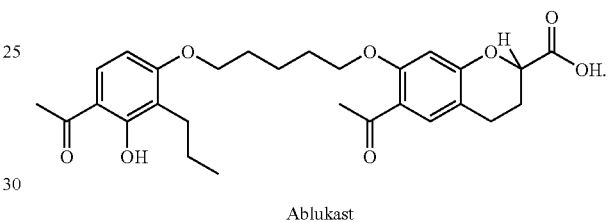

Ablukast

Montelukast is a receptor antagonist for LTD$_4$ which is sold commercially under the name Singulair® and is described in U.S. Pat. No. 5,565,473:

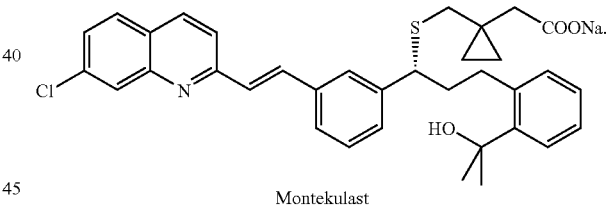

Montekulast

Other receptor antagonists for LTD$_4$ include pranlukast, verlukast (MK-679), RG-12525, Ro-245913, iralukast (CGP 45715A), and BAY x 7195.

The above-mentioned phenothiazin-3-one class of compounds, including L-651,392; the class of amidino compounds that includes CGS-25019c; the class of benzoxaolamines which includes Ontazolast; the class of benzenecarboximidamides which is typified by BIIL 284/260; the hetero-cyclic amide derivatives including Zafirlukast; Ablukast and Montelukast and the classes of compounds to which they belong; or any of the above-described derivatives of any of the above-mentioned classes, are combined with the compounds of formula I to form embodiments of the present invention.

One or more of the compounds of formula I can also be used together with other therapeutic agents as well as non-therapeutic agents to form combinations that are further embodiments of the present invention and that are useful in the treatment of a significant number of different diseases, disorders, and conditions described herein. Said embodiments comprise one or more preferred compounds together with one or more of the following:
(a) PDE IV inhibitors;
(b) 5-Lipoxygenase (5-LO) inhibitors; or 5-lipoxygenase activating protein (FLAP) antagonists;
(c) Dual inhibitors of 5-lipoxygenase (5-LO) and antagonists of platelet activating factor (PAF);
(d) Leukotriene antagonists (LTRAs) including antagonists of $LTB_4$, $LTC_4$, $LTD_4$, and $LTE_4$;
(e) Antihistaminic $H_1$ receptor antagonists including cetirizine, loratadine, desloratadine, fexofenadine, astemizole, azelastine, and chlorpheniramine;
(f) Gastroprotective $H_2$ receptor antagonists;
(g) $\alpha_1$- and $\alpha_2$-adrenoceptor agonist vasoconstrictor sympathomimetic agents administered orally or topically for decongestant use, including propylhexedrine, phenylephrine, phenylpropanolamine, pseudoephedrine, naphazoline hydrochloride, oxymetazoline hydrochloride, tetrahydrozoline hydrochloride, xylometazoline hydrochloride, and ethylnorepinephrine hydrochloride;
(h) $\alpha_1$- and $\alpha_2$-adrenoceptor agonists in combination with inhibitors of 5-lipoxygenase (5-LO);
(i) Anticholinergic agents including ipratropium bromide; tiotropium bromide; oxitropium bromide; pirenzepine; and telenzepine;
(j) $\beta_1$- to $\beta_4$-adrenoceptor agonists including metaproterenol, isoproterenol, isoprenaline, albuterol, salbutamol, formoterol, salmeterol, terbutaline, orciprenaline, bitolterol mesylate, and pirbuterol;
(k) Theophylline and aminophylline;
(l) Sodium cromoglycate;
(m) Muscarinic receptor (M1, M2, and M3) antagonists;
(n) COX-1 inhibitors (NSAIDs); COX-2 selective inhibitors including rofecoxib; and nitric oxide NSAIDs;
(o) Insulin-like growth factor type 1 (IGF-1) mimetics;
(p) Ciclesonide;
(q) Inhaled glucocorticoids with reduced systemic side effects, including prednisone, prednisolone, flunisolide, triamcinolone acetonide, beclomethasone dipropionate, budesonide, fluticasone propionate, and mometasone furoate;
(r) Tryptase inhibitors;
(s) Platelet activating factor (PAF) antagonists;
(t) Monoclonal antibodies active against endogenous inflammatory entities;
(u) IPL 576;
(v) Anti-tumor necrosis factor (TNFα) agents including Etanercept, Infliximab, and D2E7;
(w) DMARDs including Leflunomide;
(x) TCR peptides;
(y) Interleukin converting enzyme (ICE) inhibitors;
(z) IMPDH inhibitors;.
(aa) Adhesion molecule inhibitors including VLA-4 antagonists;
(bb) Cathepsins;
(cc) MAP kinase inhibitors;
(dd) Glucose-6 phosphate dehydrogenase inhibitors;
(ee) Kinin-$B_1$- and $B_2$-receptor antagonists;
(ff) Gold in the form of an aurothio group together with various hydrophilic groups;
(gg) Immunosuppressive agents, e.g., cyclosporine, azathioprine, and methotrexate;
(hh) Anti-gout agents, e.g., colchicine;
(ii) Xanthine oxidase inhibitors, e.g., allopurinol;
(jj) Uricosuric agents, e.g., probenecid, sulfinpyrazone, and benzbromarone;
(kk) Antineoplastic agents, especially antimitotic drugs including the vinca alkaloids such as vinblastine and vincristine;
(ll) Growth hormone secretagogues;
(mm) Inhibitors of matrix metalloproteases (MMPs), i.e., the stromelysins, the collagenases, and the gelatinases, as well as aggrecanase; especially collagenase-1 (MMP-1), collagenase-2 (MMP-8), collagenase-3 (MMP-13), stromelysin-1 (MMP-3), stromelysin-2 (MMP-10), and stromelysin-3 (MMP-11);
(nn) Transforming growth factor (TGFβ);
(oo) Platelet-derived growth factor (PDGF);
(pp) Fibroblast growth factor, e.g., basic fibroblast growth factor (bFGF);
(qq) Granulocyte macrophage colony stimulating factor (GM-CSF);
(rr) Capsaicin;
(ss) Tachykinin $NK_1$ and $NK_3$ receptor antagonists selected from the group consisting of NKP-608C; SB-233412 (talnetant); and D4418;
(tt) Elastase inhibitors selected from the group consisting of UT-77 and ZD-0892; and
(uu) Adenosine A2a receptor agonists.

The invention was based on the object of discovering new uses of compounds having valuable properties, especially those which may be used to prepare medicaments.

It has been found that the compounds of formula I and their salts combine very valuable pharmacological properties with good tolerability for the treatment of myocardial diseases.

The compounds of the formula I can be employed as medicament active ingredients in human and veterinary medicine. They can furthermore be employed as intermediates for the preparation of further medicament active ingredients.

Accordingly, the invention relates to the compounds of the formula I and to a process for the preparation of compounds of the formula I according to Claim 1 and salts and solvates thereof, in particular physiologically tolerated salts and solvates thereof, characterised in that a compound of the formula II

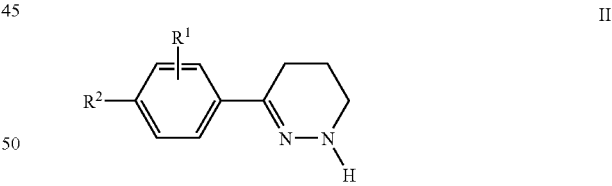

in which
$R^1$ and $R^2$ are as defined above,
is reacted with a compound of the formula III

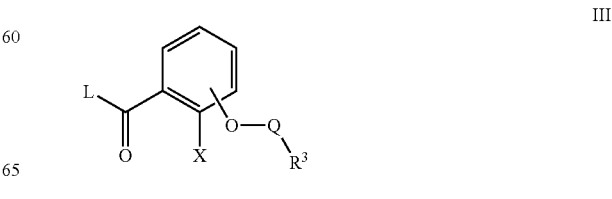

in which
X, R³ and Q are as defined above, and
L is Cl, Br, OH or a reactive esterified OH group, or in that a compound of the formula IV

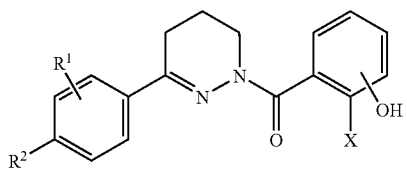

IV in which
R¹ and R² are as defined above,
is reacted with a compound of the formula V

L-Q-R³     V in which
Q and R³ are as defined in Claim 1, and
L is Cl, Br, OH or a reactive esterified OH group, and/or in that a basic compound of the formula I is converted into one of its salts by treatment with an acid.

The term "solvates of the compounds of the formula I" is taken to mean adductions of inert solvent molecules onto the compounds of the formula I which form owing to their mutual attractive force. Solvates are, for example, monohydrates or dihydrates or alcoholates.

Above and below, the radicals $R^1$, $R^2$, $R^3$, $R^4$, $A^1$, $A^2$, Hal, X, Q and L are as defined under the formulae I, II, III, IV and V, unless expressly stated otherwise.

$A^1$ and $A^2$ together may be cycloalkyl or cycloalkylene in cases where $A^1$ and $A^2$ are directly linked to a C- or a N-Atom in a $CA^1A^2$-, $NA^1A^2$- or $CONA^1A^2$-group. Therefore, the C- or N-atom of said groups linked to $A^1$ and $A^2$ are ring members of the resulting cycloalkyl- or cycloalkenyl-moiety. Additionally, one or more $CH_2$-groups, preferably only one $CH_2$-group, may be replaced by —S—, —O—, —NH—, —$NA^1$-, —$NCOA^1$- or —$NCOOA^1$-.

$A^1$ and $A^2$, independently of one another, are preferably alkyl, furthermore preferably alkyl which is substituted by from 1 to 5 fluorine and/or chlorine atoms, furthermore preferably together alternatively cycloalkyl.

In the above formulae, alkyl is preferably unbranched and has 1, 2, 3, 4, 5, 6, 7, 8, 9 or 10 carbon atoms, 1, 2, 3, 4, 5 or 6 carbon atoms, and is preferably methyl, ethyl, trifluoromethyl, pentafluoroethyl or propyl, furthermore preferably isopropyl, butyl, isobutyl, sec-butyl or tert-butyl, but also n-pentyl, neopentyl, isopentyl or n-hexyl. Particular preference is given to methyl, ethyl, trifluoromethyl, propyl, isopropyl, butyl, n-pentyl, n-hexyl or n-decyl.

Cycloalkyl preferably has 3-7 carbon atoms and is preferably cyclopropyl or cyclobutyl, furthermore preferably cyclopentyl or cyclohexyl, furthermore also cycloheptyl, particularly preferably cyclopentyl.

Alkenyl is preferably allyl, 2- or 3-butenyl, isobutenyl, sec-butenyl, further-more preferably 4-pentenyl, isopentenyl or 5-hexenyl.

Alkylene is preferably unbranched and is preferably methylene or ethylene, furthermore preferably propylene or butylene.

Alkylenecycloalkyl preferably has 5-10 carbon atoms and is preferably methylenecyclopropyl, methylenecyclobutyl, furthermore preferably methylenecyclopentyl, methylenecyclohexyl or methylenecycloheptyl, furthermore alternatively ethylenecyclopropyl, ethylenecyclobutyl, ethylenecyclopentyl, ethylenecyclohexyl or ethylenecycloheptyl, propylenecyclopentyl, propylenecyclohexyl, butylenecyclopentyl or butylenecyclohexyl.

Hal is preferably F, Cl or Br, but alternatively I, in particular F or Cl.

The radicals $R^1$ and $R^2$ may be identical or different, where $R^1$ can be in the ortho- or meta-position to $R^2$. They are, independently of one another, for example hydroxyl, —S—$CH_3$, —SO—$CH_3$, —$SO_2CH_3$, F, Cl, Br or I or together are methylenedioxy. However, they are preferably each methoxy, ethoxy, propoxy, cyclopentoxy, but also fluoro-, difluoro- or trifluoromethoxy or 1-fluoro-, 2-fluoro-, 1,2-difluoro-, 2,2-difluoro-, 1,2,2-trifluoro- or 2,2,2-trifluoroethoxy.

$R^1$ is particularly preferably methoxy, ethoxy, cyclopentoxy or isopropoxy.

$R^1$ is particularly preferably in the ortho-position to $R^2$.

$R^2$ is particularly preferably methoxy or ethoxy.

$R^3$ is preferably $A^1$, F, Cl, Br or I, hydroxyl, $NH_2$, O-alkyl, $NO_2$, alkylamino, cycloalkylamino or dialkylamino, where alkyl and cycloalkyl have one of the meanings indicated above, or

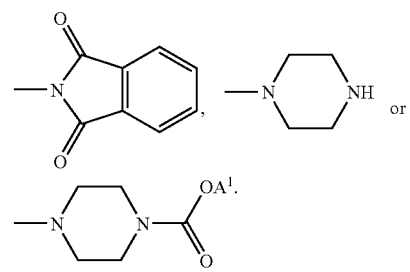

$R^3$ is particularly preferably $NH_2$, $NO_2$, methoxy, ethoxy, propoxy, isopropoxy, butoxy, pentoxy, hexyloxy or decyloxy, Cl or F, dimethylamino, diethylamino, methylamino, ethylamino,

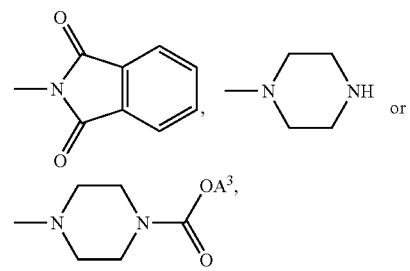

in which $A^3$ is alkyl having from 1 to 12 carbon atoms. $A^3$ is preferably n-alkyl having 6, 7, 8, 9, 10, 11 or 12 carbon atoms, in particular n-alkyl having 7 or 11 carbon atoms.

X is preferably H, F or Cl, especially H.

Q is preferably alkylene having from 1 to 10 carbon atoms, in which from 1 to 3 carbon atoms may be replaced by —O—, —NH— or —$NA^1$-, in particular methylene, ethylene, n-propylene, n-butylene, n-pentylene, n-hexylene or n-heptylene, and the following groups:

—CH$_2$CH$_2$OCH$_2$CH$_2$OCH$_2$CH$_2$—,
—CH$_2$CH$_2$OCH$_2$CH$_2$OCH$_2$CH$_2$—,
—CH$_2$CH$_2$CH$_2$OCH$_2$CH$_2$—,
—CH$_2$CH$_2$CH$_2$OCH$_2$CH$_2$OCH$_2$CH$_2$—,
—CH$_2$CH$_2$CH$_2$OCH$_2$CH$_2$CH$_2$OCH$_2$CH$_2$—,
—CH$_2$CH$_2$NHCH$_2$CH$_2$NHCH$_2$CH$_2$—,
—CH$_2$CH$_2$NHCH$_2$CH$_2$NHCH$_2$CH$_2$—,
—CH$_2$CH$_2$CH$_2$NHCH$_2$CH$_2$—,
—CH$_2$CH$_2$CH$_2$NHCH$_2$CH$_2$NHCH$_2$CH$_2$—,
—CH$_2$CH$_2$CH$_2$NHCH$_2$CH$_2$CH$_2$NHCH$_2$CH$_2$—,
—CH$_2$CH$_2$NA$^1$CH$_2$CH$_2$NA$^1$CH$_2$CH$_2$—,
—CH$_2$CH$_2$NA$^1$CH$_2$CH$_2$NA$^1$CH$_2$CH$_2$—,
—CH$_2$CH$_2$CH$_2$NA$^1$CH$_2$CH$_2$—,
—CH$_2$CH$_2$CH$_2$NA$^1$CH$_2$CH$_2$NA$^1$CH$_2$CH$_2$—,
—CH$_2$CH$_2$CH$_2$NA$^1$CH$_2$CH$_2$CH$_2$NA$^1$CH$_2$CH$_2$—, in which A$^1$ is as defined above.

The phenyl ring substituted by the —O—Q—R$^3$ group is preferably meta- or para-substituted, in particular para-substituted.

Throughout the invention, all radicals which occur more than once may be identical or different, i.e. are independent of one another.

Accordingly, the invention relates, in particular, to the compounds of the formula I in which at least one of the said radicals has one of the preferred meanings indicated above. Some preferred groups of compounds may be expressed by the following sub-formulae Ia to Ih, which conform to the formula I and in which the radicals not designated in greater detail have the meaning indicated for the formula I, but in which in Ia R$^1$ and R$^2$ are each, independently of one another, OA$^1$;

in Ib R$^1$ and R$^2$ are each, independently of one another, OA$^1$,
A$^1$ and A$^2$ are each, independently of one another, alkyl having 1-12 carbon atoms or cycloalkyl having 3-7 carbon atoms;

in Ic R$^1$ and R$^2$ are each, independently of one another, OA$^1$,
A$^1$ and A$^2$ are each, independently of one another, alkyl having 1-12 carbon atoms or cycloalkyl having 3-7 carbon atoms,
R$^3$ is A$^1$, F, Cl, hydroxyl, NH$_2$, OA$^1$, NO$_2$, alkylamino, cycloalkylamino, dialkylamino,

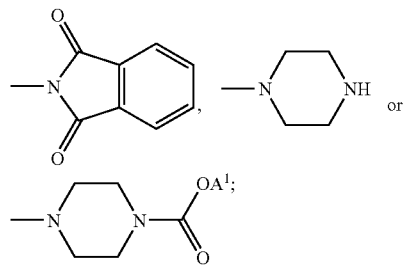

in Id R$^1$ and R$^2$ are each, independently of one another, OA$^1$,
A$^1$ and A$^2$ are each, independently of one another, alkyl having 1-12 carbon atoms or cycloalkyl having 3-7 carbon atoms,
R$^3$ is A$^1$, F, Cl, hydroxyl, NH$_2$, OA$^1$, NO$_2$, alkylamino, cycloalkylamino, dialkylamino,

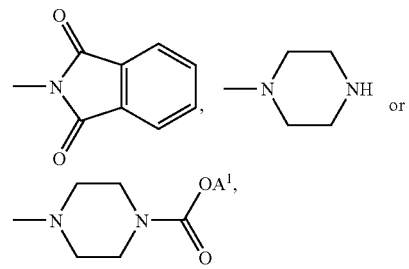

Q is alkylene having from 1 to 10 carbon atoms, in which from 1 to 3 carbon atoms may be replaced by —O—;

in Ie R$^1$ and R$^2$ are each, independently of one another, OA$^1$,
A$^1$ and A$^2$ are each, independently of one another, alkyl having 1-12 carbon atoms or cycloalkyl having 3-7 carbon atoms,
R$^3$ is NH$_2$, NO$_2$, methoxy, ethoxy, propoxy, isopropoxy, butoxy, pentoxy, hexyloxy or decyloxy, Cl or F, dimethylamino, diethylamino, methylamino, ethylamino,

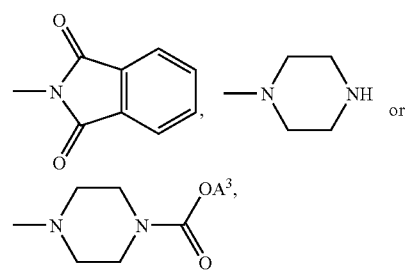

in which A$^3$ is alkyl having from 1 to 12 carbon atoms,
Q is alkylene having from 1 to 10 carbon atoms, in which from 1 to 3 carbon atoms may be replaced by —O—;

in If R$^1$ and R$^2$ are each, independently of one another, OA$^1$,
A$^1$ and A$^2$ are each, independently of one another, alkyl having 1-12 carbon atoms or cycloalkyl having 3-7 carbon atoms,
R$^3$ is NH$_2$, NO$_2$, methoxy, ethoxy, propoxy, isopropoxy, butoxy, pentoxy, hexyloxy or decyloxy, Cl or F, dimethylamino, diethylamino, methylamino, ethylamino,

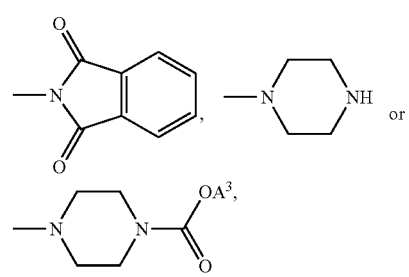

in which A$^3$ is alkyl having from 1 to 12 carbon atoms,
Q is methylene, ethylene, n-propylene, n-butylene, n-pentylene, n-hexylene or n-heptylene or the following groups:
—CH$_2$CH$_2$OCH$_2$CH$_2$OCH$_2$CH$_2$—,
—CH$_2$CH$_2$OCH$_2$CH$_2$OCH$_2$CH$_2$—,
—CH$_2$CH$_2$CH$_2$OCH$_2$CH$_2$—,
—CH$_2$CH$_2$CH$_2$OCH$_2$CH$_2$OCH$_2$CH$_2$—, —CH$_2$CH$_2$CH$_2$OCH$_2$CH$_2$CH$_2$OCH$_2$CH$_2$—,
—CH$_2$CH$_2$NHCH$_2$CH$_2$NHCH$_2$CH$_2$—,
—CH$_2$CH$_2$NHCH$_2$CH$_2$NHCH$_2$CH$_2$—,
—CH$_2$CH$_2$CH$_2$NHCH$_2$CH$_2$—,
—CH$_2$CH$_2$CH$_2$NHCH$_2$CH$_2$NHCH$_2$CH$_2$—,
—CH$_2$CH$_2$CH$_2$NHCH$_2$CH$_2$CH$_2$NHCH$_2$CH$_2$—,
—CH$_2$CH$_2$NA$^1$CH$_2$CH$_2$NA$^1$CH$_2$CH$_2$—,
—CH$_2$CH$_2$NA$^1$CH$_2$CH$_2$NA$^1$CH$_2$CH$_2$—,
—CH$_2$CH$_2$CH$_2$NA$^1$CH$_2$CH$_2$—,
—CH$_2$CH$_2$CH$_2$NA$^1$CH$_2$CH$_2$NA$^1$CH$_2$CH$_2$—,
—CH$_2$CH$_2$CH$_2$NA$^1$CH$_2$CH$_2$CH$_2$NA$^1$CH$_2$CH$_2$—,
in which A$^1$ is as defined above;
in Ig R$^1$ is ethoxy in the ortho-position to R$^2$,
R$^2$ is methoxy;
in Ih R$^1$ is ethoxy in the ortho-position to R$^2$,
R$^2$ is methoxy,
A$^1$ and A$^2$ are each, independently of one another, alkyl having 1-12 carbon atoms or cycloalkyl having 3-7 carbon atoms,
R$^3$ is A$^1$, F, Cl, hydroxyl, NH$_2$, OA$^1$, NO$_2$, alkylamino, cycloalkylamino, dialkylamino,

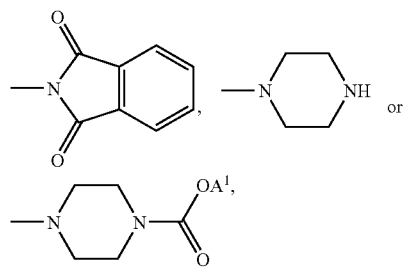

Q is alkylene having from 1 to 10 carbon atoms, in which from 1 to 3 carbon atoms may be replaced by —O—;
in Ii R$^1$ is cyclopentyloxy in the ortho-position to R$^2$,
R$^2$ is methoxy;
in Ij R$^1$ is cyclopentyloxy in the ortho-position to R$^2$,
R$^2$ is methoxy,
A$^1$ and A$^2$ are each, independently of one another, alkyl having 1-12 carbon atoms or cycloalkyl having 3-7 carbon atoms,
R$^3$ is A$^1$, F, Cl, hydroxyl, NH$_2$, OA$^1$, NO$_2$, alkylamino, cycloalkylamino, dialkylamino,

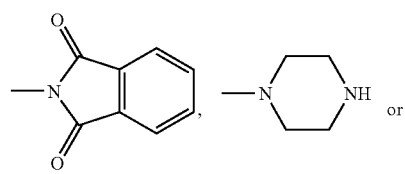

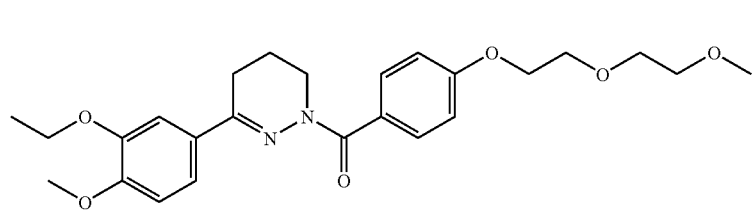

Q is alkylene having from 1 to 10 carbon atoms, in which from 1 to 3 carbon atoms may be replaced by —O—.

Particular preference is given, to the compounds of the formulae I1 to I74:

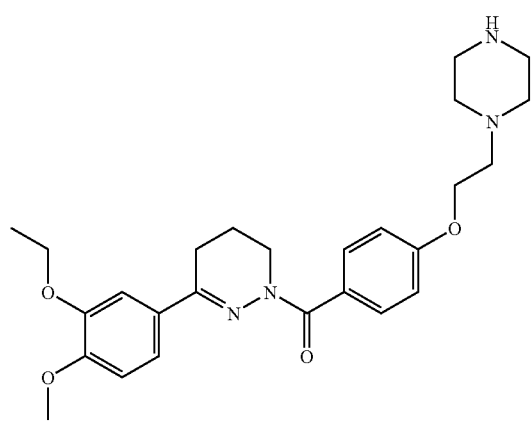

-continued
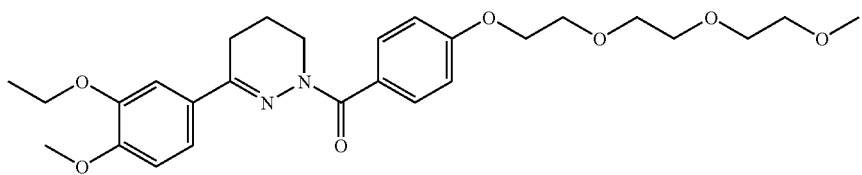
I3
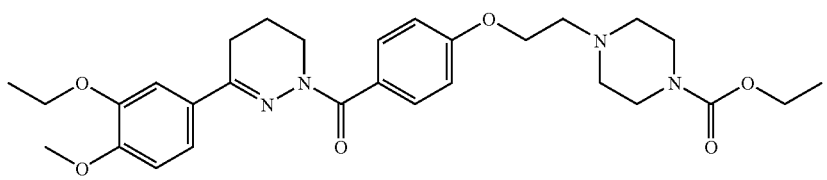
I4
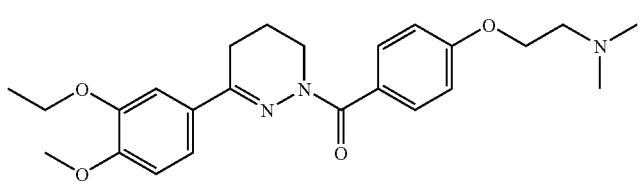
I5
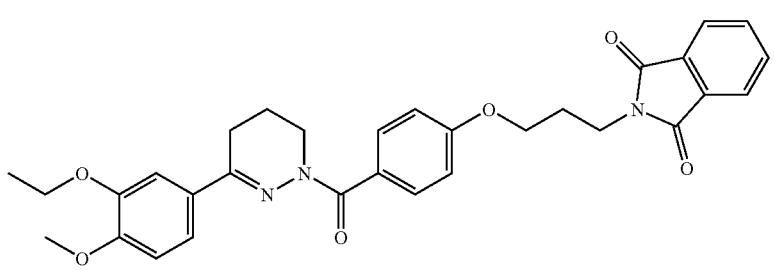
I6
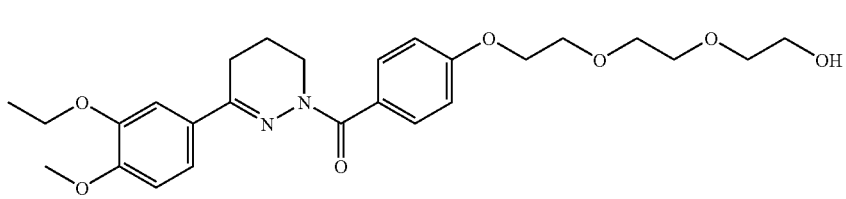
I7
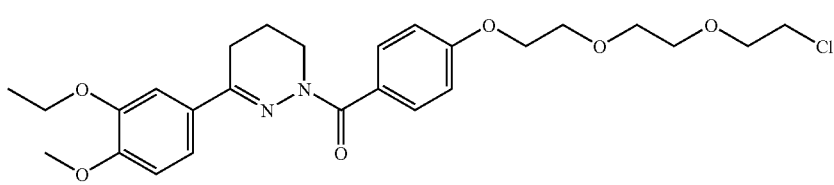
I8
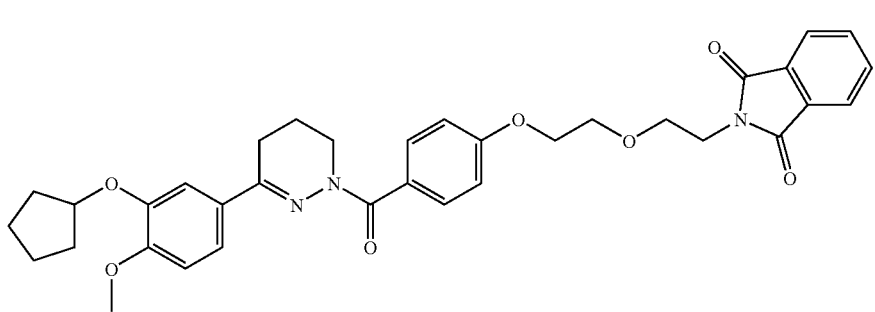
I9

-continued
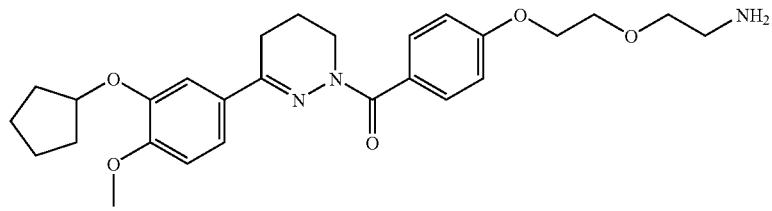
I10
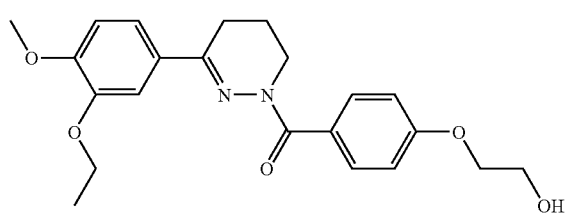
I11
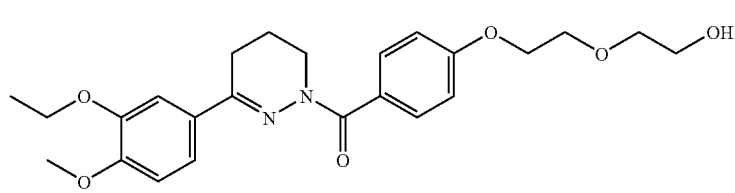
I12
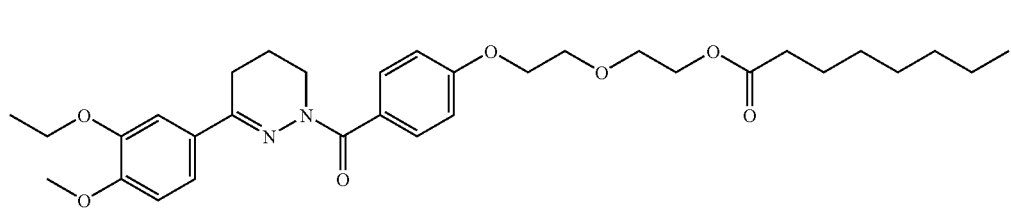
I13
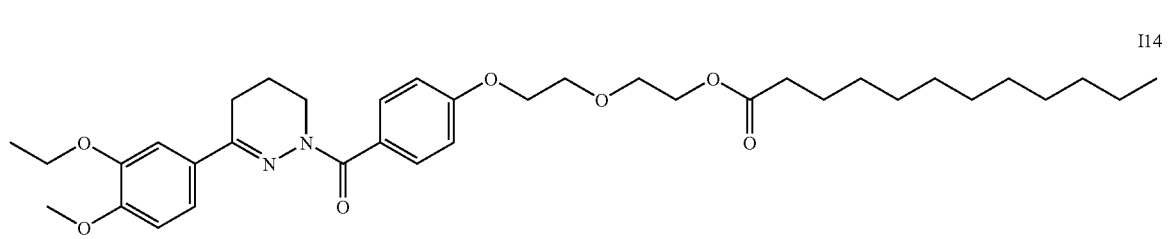
I14
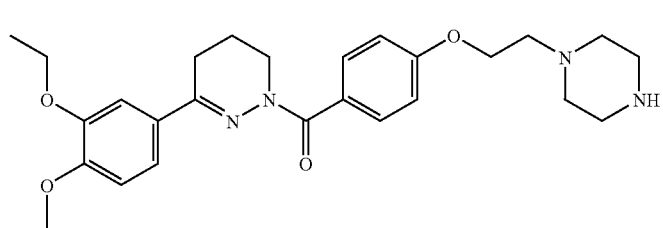
I15
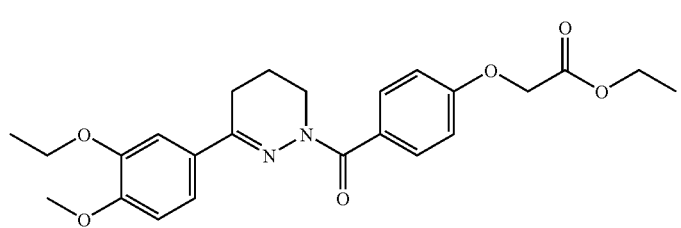
I16

-continued
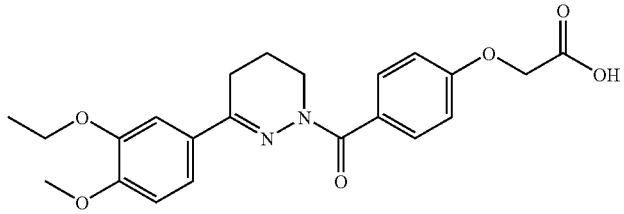
I17
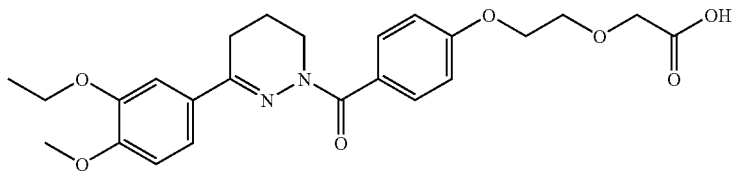
I18
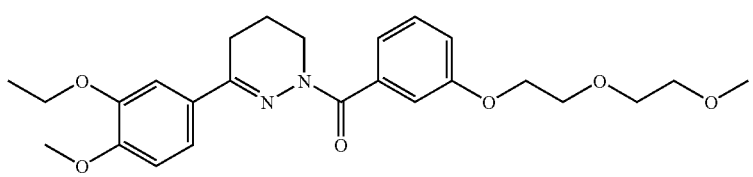
I19
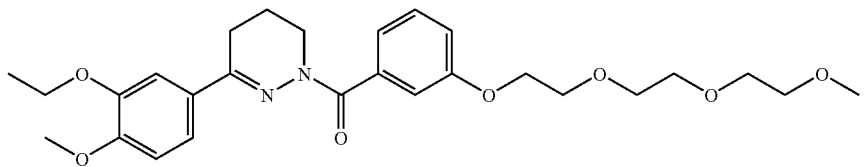
I20
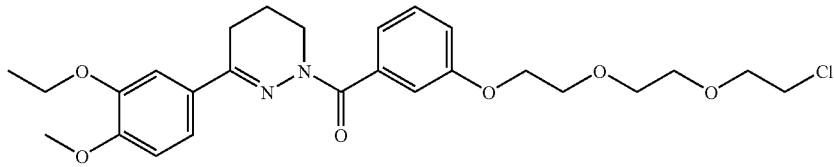
I21
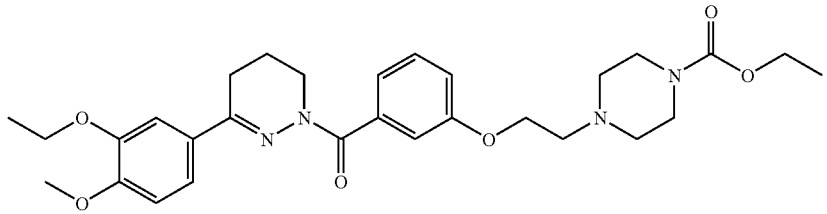
I22
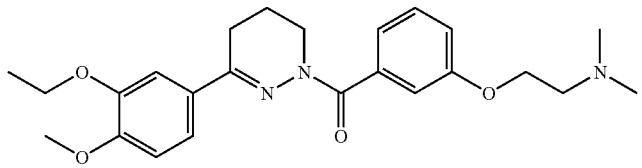
I23
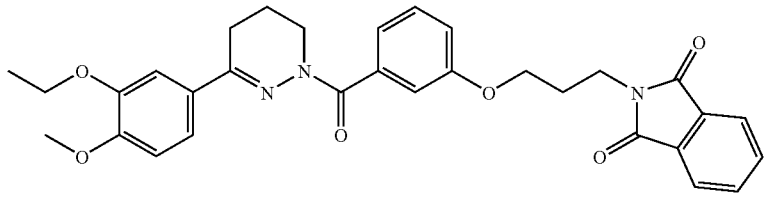
I24

-continued
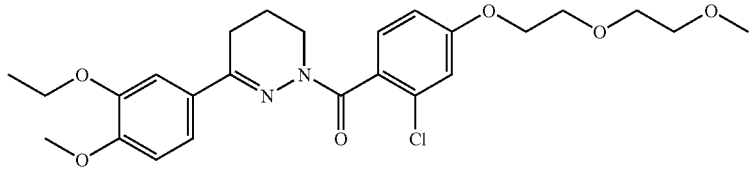
I25
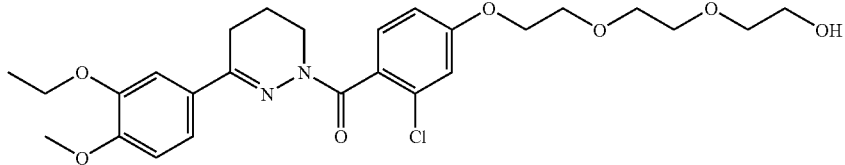
I26
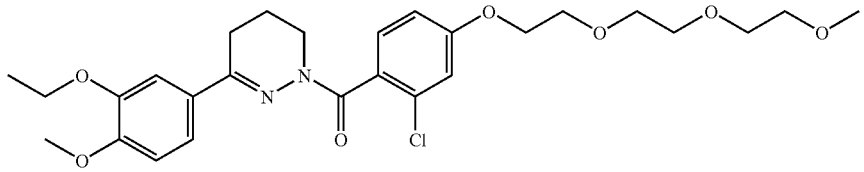
I27
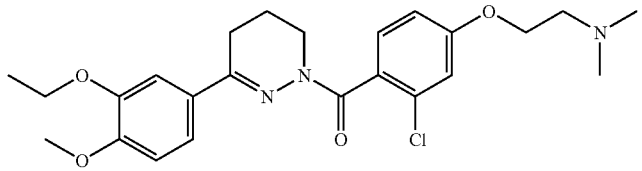
I28
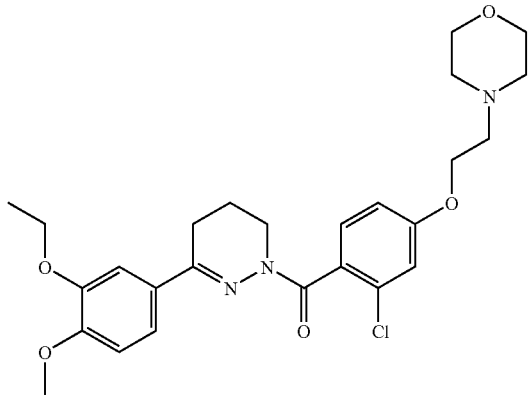
I29
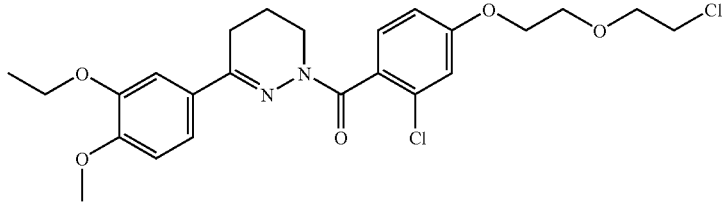
I30
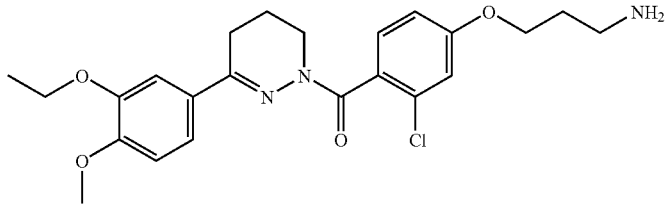
I31

-continued
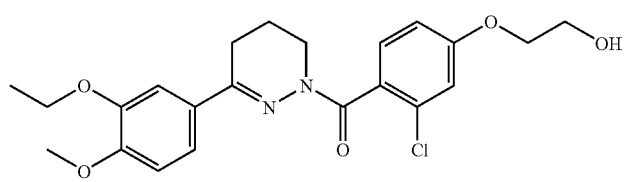
I32
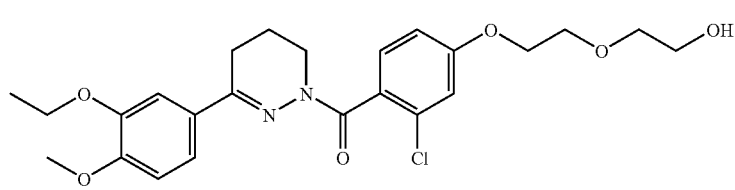
I33
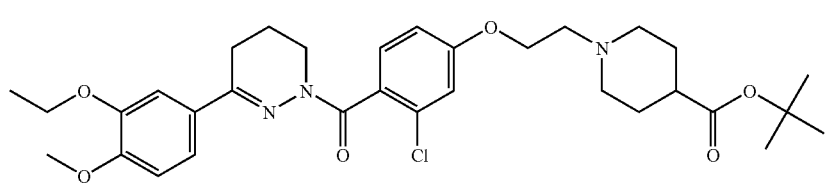
I34
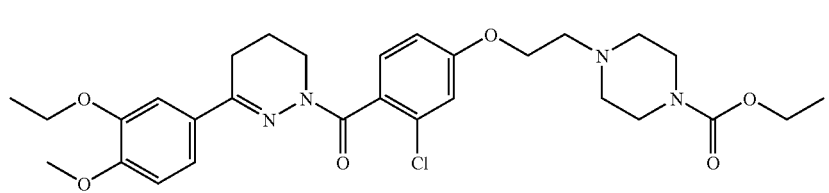
I35
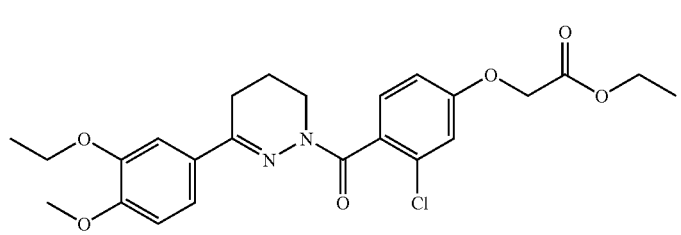
I36
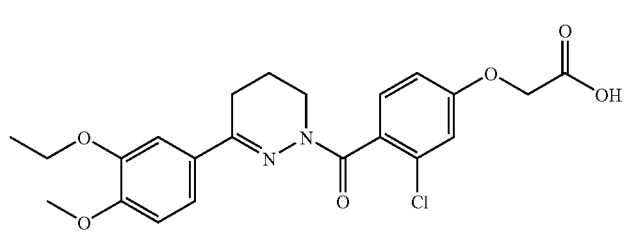
I37
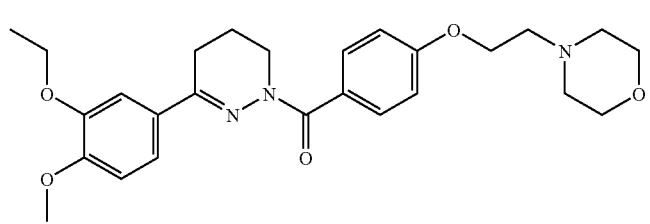
I38

-continued
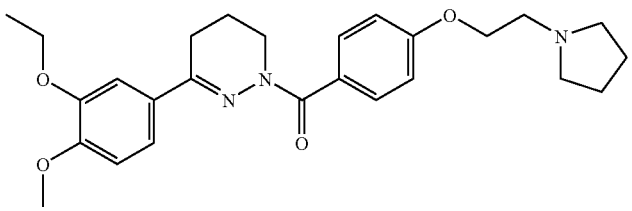
I39
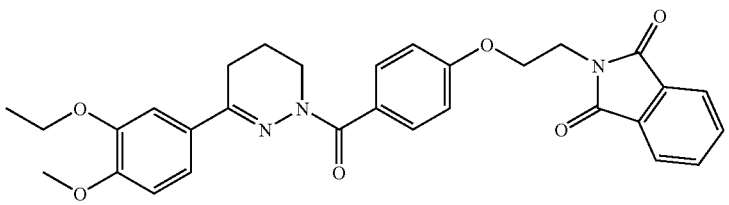
I40
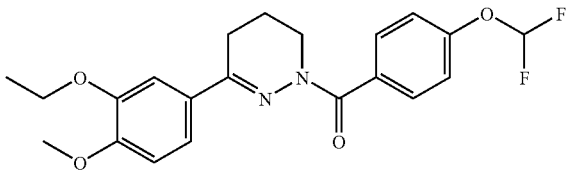
I41
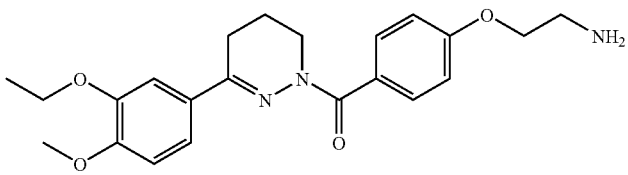
I42
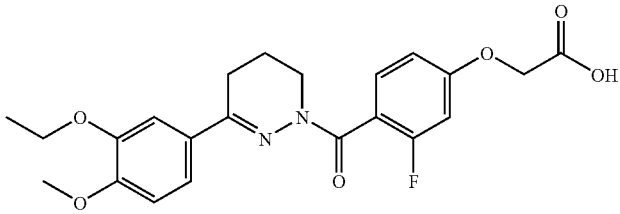
I43
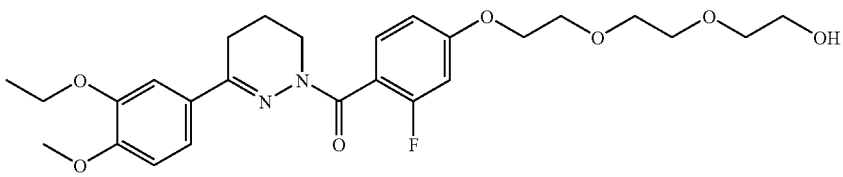
I44
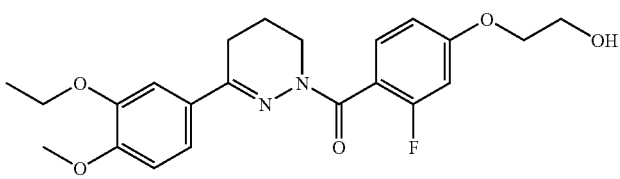
I45
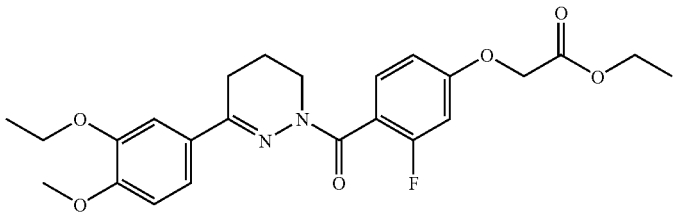
I46

-continued
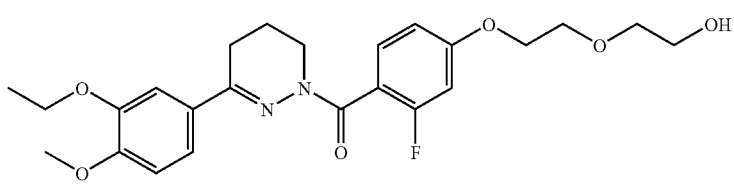
I47
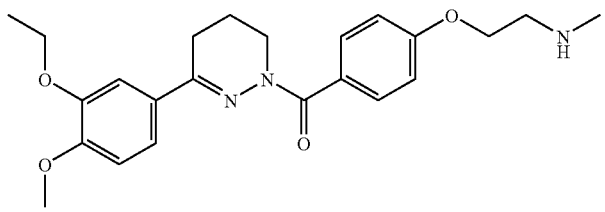
I48
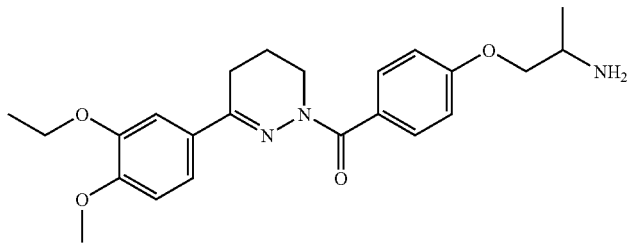
I49
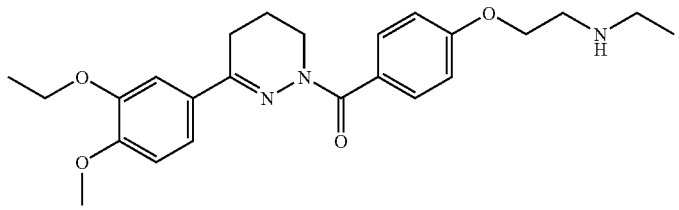
I50
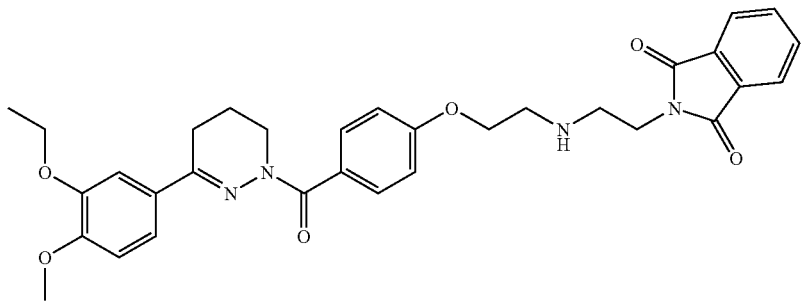
I51
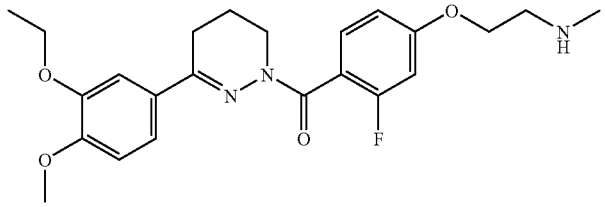
I52

-continued
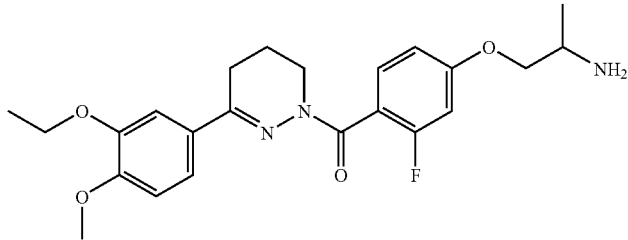
I53
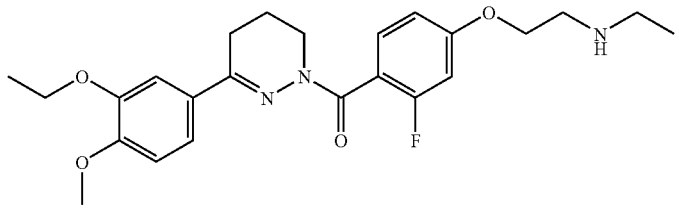
I54
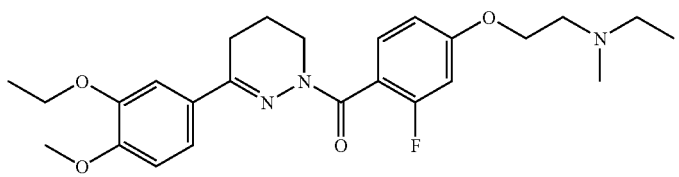
I55
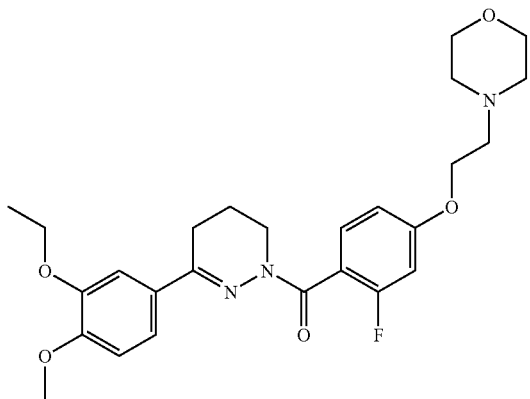
I56
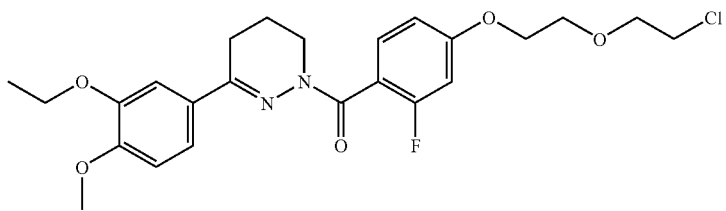
I57
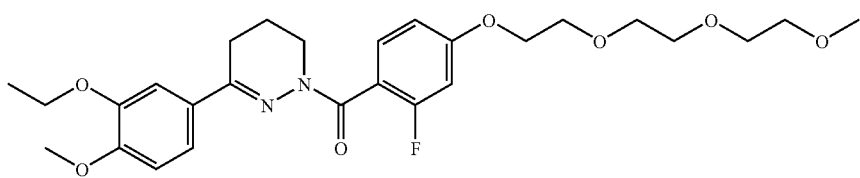
I58

-continued
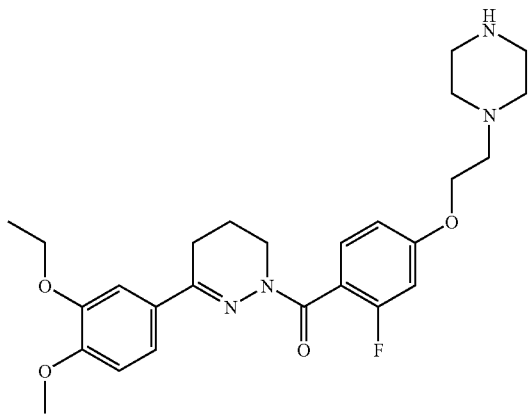
I59
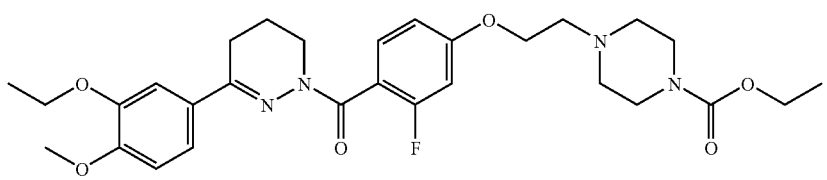
I60
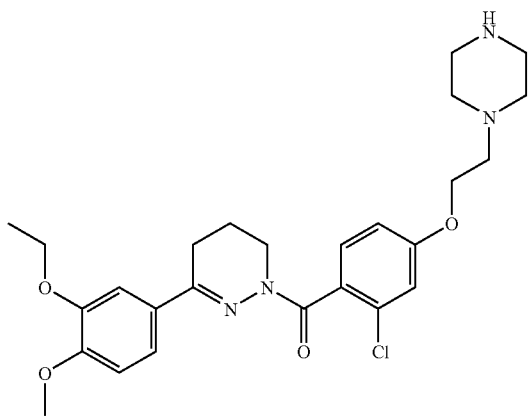
I61
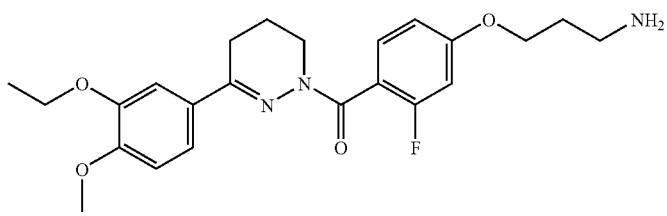
I62
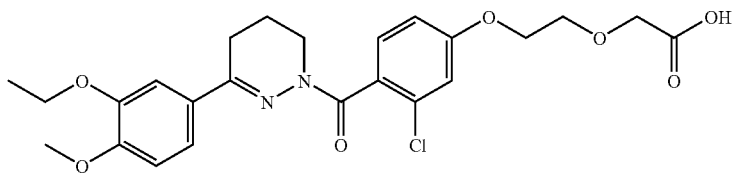
I63
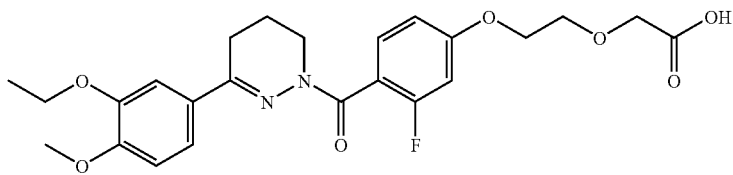
I64

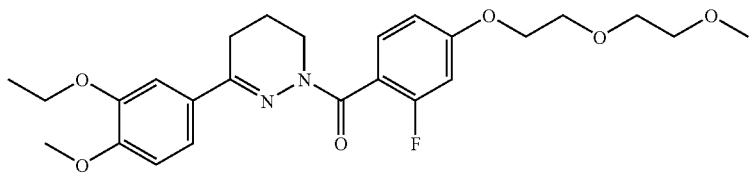
I65
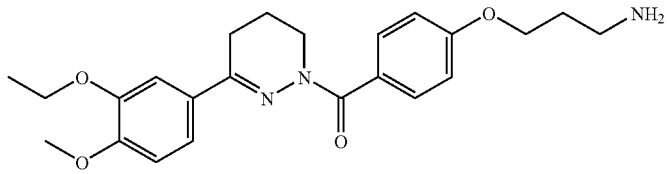
I66
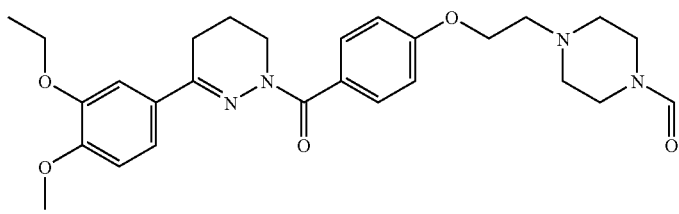
I67
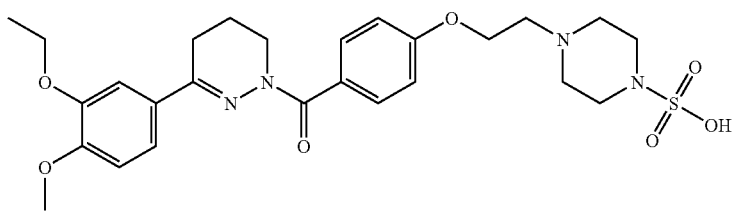
I68
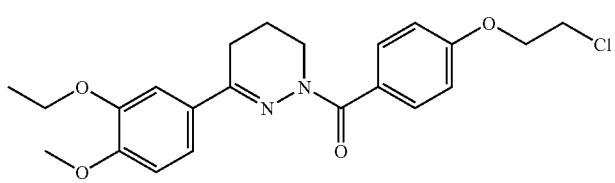
I69
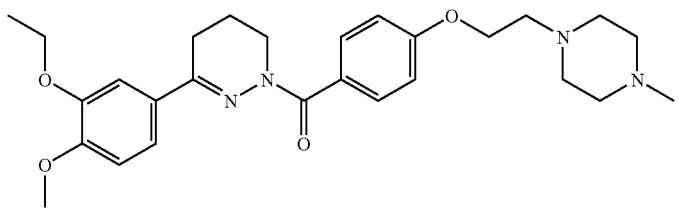
I70
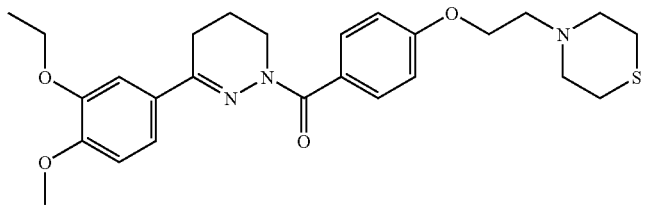
I71

-continued

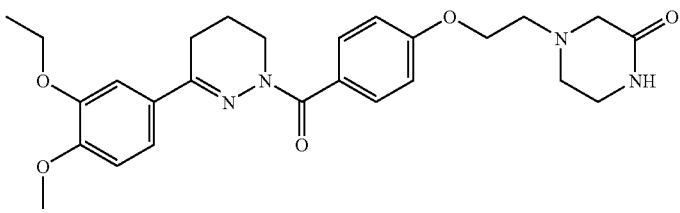

I72

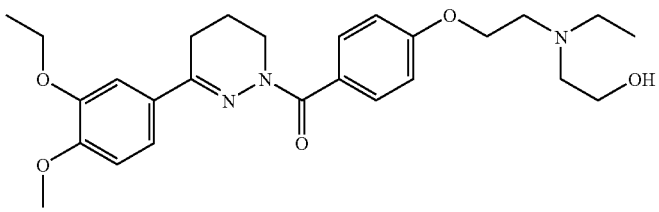

I73

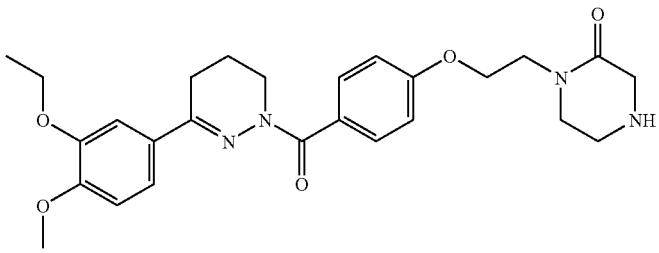

I74 and salts and solvates thereof.

The compounds of the formula I and also the starting materials for their preparation are, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants which are known per se, but are not mentioned here in greater detail.

If L is a reactive esterified OH group, this is preferably alkylsulfonyloxy having 1-6 carbon atoms (preferably methylsulfonyloxy) or arylsulfonyloxy having 6-10 carbon atoms (preferably phenyl- or p-tolylsulfonyloxy, furthermore also 2-naphthalenesulfonyloxy). Furthermore, the reactive esterified OH group L can also be obtained in situ, for example by reaction with polymeric or monomeric triphenylphosphine or other phosphines and di-tert-butyl azodicarboxylate or analogous azodicarboxylates.

If desired, the starting materials can also be formed in situ by not isolating them from the reaction mixture, but instead immediately converting them further into the compounds of the formula I.

On the other hand, it is possible to carry out the reaction stepwise.

The compounds of the formula I can preferably be obtained by reacting compounds of the formula II with compounds of the formula III.

Some of the starting materials of the formula II and III are known. If they are not known, they can be prepared by methods known per se.

In detail, the reaction of the compounds of the formula II with compounds of the formula III is carried out in the presence or absence of a solvent, preferably an inert solvent, at temperatures between about −20 and about 150°, preferably between 20 and 100°.

Examples of suitable solvents are hydrocarbons, such as hexane, petroleum ether, benzene, toluene or xylene; chlorinated hydrocarbons, such as trichloroethylene, 1,2-dichloroethane, tetrachloromethane, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether or ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); nitro compounds, such as nitromethane or nitrobenzene; esters, such as ethyl acetate, or mixtures of the said solvents.

Compounds of the formula I can furthermore be obtained by reacting compounds of the formula IV with compounds of the formula V. The starting compounds of the formulae IV and V are generally known. If they are not known, they can be prepared by methods known per se.

In the compounds of the formula III the radical —CO-L is a pre-activated carboxylic acid, preferably a carboxylic acid halide.

The reaction of the compounds of the formula IV with compounds of the formula V is carried out under the same conditions relating to the reaction time, temperature and solvent as have been described for the reaction of the compounds of the formula II with compounds of the formula III.

A compound within the scope of formula I may be such that its constituent atoms are capable of being arranged in space in two or more different ways, despite having identical connectivities. As a consequence, said compound exists in the form of stereoisomers. Where the stereoisomers are nonsuperimposable mirror images of each other, they are enantiomers which have chirality or handedness, because of the presence of one or more asymmetric carbon atoms in their constituent structure. Enantiomers are optically active and therefore distinguishable because they rotate the plane of polarized light by equal amounts, but in opposite directions.

All of these well known aspects of the stereochemistry of the compounds of formula I are contemplated to be a part of the present invention. Within the scope of the present invention there is thus included compounds of formula I that are stereoisomers, and where these are enantiomers, the individual enantiomers, racemic mixtures of said enantiomers, and artificial, i.e., manufactured mixtures containing proportions of said enantiomers that are different from the proportions of said enantiomers found in a racemic mixture. Where a compound of formula I comprises stereoisomers that are diastereomers, there is included within the scope of said compound the individual diastereomers as well as mixtures of any two or more of said diastereomers in any proportions thereof.

By way of illustration, in the case where there is a single asymmetric carbon atom in a compound of formula I, resulting in the (−)(R) and (+)(S) enantiomers thereof, there is included within the scope of said compound all pharmaceutically acceptable salt forms, prodrugs and metabolites thereof which are therapeutically active and useful in treating or preventing the diseases and conditions described further herein. Where a compound of formula I exists in the form of (−)(R) and (+)(S) enantiomers, there is also included within the scope of said compound the (+)(S) enantiomer alone, or the (−)(R) enantiomer alone, in the case where all, substantially all, or a predominant share of the therapeutic activity resides in only one of said enantiomers, and/or unwanted side effects reside in only one of said enantiomers. In the case where there is substantially no difference between the biological activities of both enantiomers, there is further included within the scope of said compound of formula I the (+)(S) enantiomer and the (−)(R) enantiomer present together as a racemic mixture or as a non-racemic mixture in any ratio of proportionate amounts thereof.

For example, the particular biological activities and/or physical and chemical properties of a pair or set of enantiomers of a compound of formula I where such exist, may suggest use of said enantiomers in certain ratios to constitute a final therapeutic product. By way of illustration, in the case where there is a pair of enantiomers, they may be employed in ratios such as 90% (R)-10% (S); 80% (R)-20% (S); 70% (R)-30% (S); 60% (R)-40% (S); 50% (R)-50% (S); 40% (R)-60% (S); 30% (R)-70% (S); 20% (R)-80% (S); and 10% (R)-90% (S). After evaluating the properties of the various enantiomers of a compound of formula I where such exist, the proportionate amount of one or more of said enantiomers with certain desired properties that will constitute the final therapeutic product can be determined in a straightforward manner.

The invention therefor also relates to the optically active forms (stereoisomers), the enantiomers, the racemates, the diastereomers and the salts and solvates of these compounds. The term solvates of the compounds is taken to mean adductions of inert solvent molecules onto the compounds which form owing to their mutual attractive force. Solvates are, for example, monohydrates or dihydrates or alcoholates.

The term pharmaceutically usable derivatives is taken to mean, for example, the salts of the compounds according to the invention and also so-called prodrug compounds.

The term prodrug derivatives is taken to mean, for example, compounds of the formula I which have been modified with, for example, alkyl or acyl groups, sugars or oligopeptides and which are rapidly cleaved in the organism to give the effective compounds according to the invention. These also include biodegradable polymer derivatives of the compounds according to the invention, as described, for example, in Int. J. Pharm. 115, 61-67 (1995).

The invention also relates to mixtures of the compounds of the formula I according to the invention, for example mixtures of two diastereomers, for example in the ratio 1:1, 1:2, 1:3, 1:4, 1:5, 1:10, 1:100 or 1:1000. These are particularly preferably mixtures of stereoisomeric compounds.

A base of the formula I can be converted into the associated acid-addition salt using an acid, for example by reaction of equivalent amounts of the base and the acid in a solvent, preferably an inert solvent such as ethanol, followed by evaporation. Suitable acids for this reaction are, in particular, those which give physiologically acceptable acids. Thus, it is possible to use inorganic acids, for example sulfuric acid, nitric acid, hydrohalic acids, such as hydrochloric acid or hydrobromic acid, phosphoric acids, such as orthophosphoric acid, or sulfamic acid, furthermore organic acids, in particular aliphatic, alicyclic, araliphatic, aromatic or heterocyclic monobasic or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and -disulfonic acids, or laurylsulfuric acid. Salts with physiologically unacceptable acids, for example picrates, can be used for the isolation and/or purification of the compounds of the formula I.

On the other hand, if desired, the free bases of the formula I can be liberated from their salts using bases (for example sodium hydroxide, potassium hydroxide, sodium carbonate or potassium carbonate).

The invention relates to compounds of the formula I and physiologically acceptable salts and solvates thereof as medicaments.

The invention also relates to the compounds of the formula I and physiologically acceptable salts and solvates thereof as phosphodiesterase IV inhibitors.

The invention furthermore relates to the use of the compounds of the formula I and/or physiologically acceptable salts and/or solvates thereof for the preparation of pharmaceutical preparations, in particular by non-chemical methods. In this case, they can be converted into a suitable dosage form together with at least one solid, liquid and/or semi-liquid excipient or assistant and, if desired, in combination with one or more further active ingredients.

The invention furthermore relates to pharmaceutical preparations comprising at least one compound of the formula I and/or one of its physiologically acceptable salts and/or solvates.

The preferred compounds of formula I show a selective inhibition of phosphodiesterase IV, which is associated with an intracellular increase in cAMP (N. Sommer et al., Nature Medicine, 1, 244-248 (1995)).

The inhibition of PDE IV can be demonstrated, for example, analogously to C. W. Davis in Biochim. Biophys. Acta 797, 354-362 (1984). The affinity of the compounds of the invention for phosphodiesterase IV is measured by determining their $IC_{50}$ values (the concentration of inhibitor required to achieve 50% inhibition of the enzyme activity).

Preferably, the invention provides for the use of the compounds mentioned above for preparing a medicament for treating myocardial diseases, where said myocardial diseases show inflammatory and immunological characteristics.

Most preferably, the invention provides for the use of the compounds of formula I for preparing a medicament for treating coronary artery disease, reversible or irreversible myocardial ischemia/reperfusion injury, acute or chronic heart failure and restenosis, including instent-restenosis and stent-in-stent-restenosis.

Moreover, the invention provides for the use of the compounds mentioned above for preparing a medicament for treating ventricular remodeling after infarction or congestive heart failure of different severity (according to NYHA class I to IV).

The preparations for the treatment of the mentioned diseases can be used as medicaments in human or veterinary medicine. Suitable excipients are organic or inorganic substances which are suitable for enteral (for example oral), parenteral, topical or nasal (for example in the form of nasal spray) administration and do no react with the novel compounds, for example water, vegetable oils, benzyl alcohols, alkylene glycols, polyethylene glycols, glycerol triacetate, gelatine, carbohydrates, such as lactose or starch, magnesium stearates, talc or vaseline. Suitable for oral administration are, in particular, tablets, pills, coated tablets, capsules, powders, granules, syrups, juices or drops, suitable for rectal administration are suppositories, suitable for parenteral administration are solutions, preferably oil-based or aqueous solutions, furthermore suspensions, emulsions or implants, and suitable for topical application are ointments, creams or powders. The novel compounds may also be lyophilised and the resultant lyophilisates used, for example, for the preparation of injection preparations. The preparations indicated may be sterilised and/or comprise assistants, such as lubricants, preservatives, stabilisers and/or wetting agents, emulsifiers, salts for modifying the osmotic pressure, buffer substances, colorants and flavours and/or one or more further active ingredients, for example one or more vitamins.

The description which follows concerns the manner in which the preferred compounds as defined above, together with other therapeutic agents or non-therapeutic agents where these are desired, are combined with what are for the most part conventional pharmaceutically acceptable carriers to form dosage forms suitable for the different routes of administration which are utilized for any given patient, as well as appropriate to the disease, disorder, or condition for which any given patient is being treated.

The pharmaceutical compositions of the present invention comprise any one or more of the above-described inhibitory compounds of the present invention, or a pharmaceutically acceptable salt thereof as also above-described, together with a pharmaceutically acceptable carrier in accordance with the properties and expected performance of such carriers which are well-known in the pertinent art.

The amount of active ingredient that may be combined with the carrier materials to produce a single dosage form will vary depending upon the host treated, and the particular mode of administration. It should be understood, however, that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of active ingredient may also depend upon the therapeutic or prophylactic agent, if any, with which the ingredient is co-administered.

The preferred compounds may be utilized in the form of acids, esters, or other chemical classes of compounds to which the compounds described belong. It is also within the scope of the present invention to utilize those compounds in the form of pharmaceutically acceptable salts derived from various organic and inorganic acids and bases. An active ingredient comprising a preferred compound is often utilized in the form of a salt thereof, especially where said salt form confers on said active ingredient improved pharmacokinetic properties as compared to the free form of said active ingredient or some other salt form of said active ingredient utilized previously. The pharmaceutically acceptable salt form of said active ingredient may also initially confer a desirable pharmacokinetic property on said active ingredient which it did not previously possess, and may even positively affect the pharmacodynamics of said active ingredient with respect to its therapeutic activity in the body.

The pharmacokinetic properties of said active ingredient which may be favorably affected include, e.g., the manner in which said active ingredient is transported across cell membranes, which in turn may directly and positively affect the absorption, distribution, biotransformation and excretion of said active ingredient. While the route of administration of the pharmaceutical composition is important, and various anatomical, physiological and pathological factors can critically affect bioavailability, the solubility of said active ingredient is usually dependent upon the character of the particular salt form thereof which it utilized. Further, as the artisan understands, an aqueous solution of said active ingredient will provide the most rapid absorption of said active ingredient into the body of a patient being treated, while lipid solutions and suspensions, as well as solid dosage forms, will result in less rapid absorption of said active ingredient. Oral ingestion of said active ingredient is the most preferred route of administration for reasons of safety, convenience, and economy, but absorption of such an oral dosage form can be adversely affected by physical characteristics such as polarity, emesis caused by irritation of the gastrointestinal mucosa, destruction by digestive enzymes and low pH, irregular absorption or propulsion in the presence of food or other drugs, and metabolism by enzymes of the mucosa, the intestinal flora, or the liver. Formulation of said active ingredient into different harmaceutically acceptable salt forms may be effective in overcoming or alleviating one or more of the above-recited problems encountered with absorption of oral dosage forms.

Among the pharmaceutical salts recited further above, those which are preferred include, but are not limited to acetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate, and tromethamine.

Multiple salts forms are included within the scope of the present invention where a preferred compound of the present invention contains more than one group capable of forming such pharmaceutically acceptable salts. Examples of typical multiple salt forms include, but are not limited to bitartrate, diacetate, difumarate, dimeglumine, diphosphate, disodium, and trihydrochloride.

The pharmaceutical compositions of the present invention comprise any one or more of the above-described inhibitory compounds as defined in claims 1, 2 or 3, or a pharmaceutically acceptable salt thereof as also above-described, together with a pharmaceutically acceptable carrier in accordance with the properties and expected performance of such carriers which are well-known in the pertinent art.

The term "carrier" as used herein includes acceptable diluents, excipients, adjuvants, vehicles, solubilization aids, viscosity modifiers, preservatives and other agents well known to the artisan for providing favorable properties in the final pharmaceutical composition. In order to illustrate such carriers, there follows a brief survey of pharmaceutically acceptable carriers that may be used in the pharmaceutical compositions of the present invention, and thereafter a more detailed description of the various types of ingredients. Typical carriers include but are by no means limited to, ion exchange compositions; alumina; aluminum stearate; lecithin; serum proteins, e.g., human serum albumin; phosphates; glycine; sorbic acid; potassium sorbate; partial glyceride mixtures of saturated vegetable fatty acids; hydrogenated palm oils; water; salts or electrolytes, e.g., prolamine sulfate, disodium hydrogen phosphate, potassium hydrogen phosphate, sodium chloride, and zinc salts; colloidal silica; magnesium trisilicate; polyvinyl pyrrolidone; cellulose-based substances; e.g., sodium carboxy-methylcellulose; polyethylene glycol; polyacrylates; waxes; polyethylenepolyoxypropylene-block polymers; and wool fat.

More particularly, the carriers used in the pharmaceutical compositions of the present invention comprise various classes and species of additives which are members independently selected from the groups consisting essentially of those recited in the following paragraphs.

Acidifying and alkalizing agents are added to obtain a desired or predetermined pH and comprise acidifying agents, e.g., acetic acid, glacial acetic acid, malic acid, and propionic acid. Stronger acids such as hydrochloric acid, nitric acid and sulfuric acid may be used but are less preferred. Alkalizing agents include, e.g., edetol, potassium carbonate, potassium hydroxide, sodium borate, sodium carbonate, and sodium hydroxide. Alkalizing agents which contain active amine groups, such as diethanolamine and trolamine, may also be used.

Aerosol propellants are required where the pharmaceutical composition is to be delivered as an aerosol under significant pressure. Such propellants include, e.g., acceptable fluorochlorohydrocarbons such as dichlorodifluoromethane, dichlorotetrafluoroethane, and trichloromonofluoromethane; nitrogen; or a volatile hydrocarbon such as butane, propane, isobutane or mixtures thereof.

Antimicrobial agents including antibacterial, antifungal and antiprotozoal agents are added where the pharmaceutical composition is topically applied to areas of the skin which are likely to have suffered adverse conditions or sustained abrasions or cuts which expose the skin to infection by bacteria, fungi or protozoa. Antimicrobial agents include such compounds as benzyl alcohol, chlorobutanol, phenylethyl alcohol, phenyl-mercuric acetate, potassium sorbate, and sorbic acid. Antifungal agents include such compounds as benzoic acid, butylparaben, ethylparaben, methylparaben, propylparaben, and sodium benzoate.

Antimicrobial preservatives are added to the pharmaceutical compositions of the present invention in order to protect them against the growth of potentially harmful microorganisms, which usually invade the aqueous phase, but in some cases can also grow in the oil phase of a composition. Thus, preservatives with both aqueous and lipid solubility are desirable. Suitable antimicrobial preservatives include, e.g., alkyl esters of p-hydroxybenzoic acid, propionate salts, phenoxyethanol, methylparaben sodium, propylparaben sodium, sodium dehydroacetate, benzalkonium chloride, benzethonium chloride, benzyl alcohol, hydantoin derivatives, quaternary ammonium compounds and cationic polymers, imidazolidinyl urea, diazolidinyl urea, and trisodium ethylenediamine tetracetate (EDTA). Preservatives, are preferably employed in amounts ranging from about 0.01% to about 2.0% by weight of the total composition.

Antioxidants are added to protect all of the ingredients of the pharmaceutical composition from damage or degradation by oxidizing agents present in the composition itself or the use environment, e.g., anoxomer, ascorbyl palmitate, butylated hydroxyanisole, butylated hydroxytoluene, hypophosphorous acid, potassium metabisulfite, propyloctyl and dodecyl gallate, sodium metabisulfite, sulfur dioxide, and tocopherols.

Buffering agents are used to maintain a desired pH of a composition once established, from the effects of outside agents and shifting equilibria of components of the composition. The buffering may be selected from among those familiar to the artisan skilled in the preparation of pharmaceutical compositions, e. g., calcium, acetate, potassium metaphosphate, potassium phosphate monobasic, and tartaric acid.

Chelating agents are used to help maintain the ionic strength of the pharmaceutical composition and bind to and effectively remove destructive compounds and metals, and include, e.g., edetate dipotassium, edetate disodium, and edetic acid.

Dermatologically active agents are added to the pharmaceutical compositions of the present invention where they are to be applied topically, and include, e.g., wound healing agents such as peptide derivatives, yeast, panthenol, hexylresorcinol, phenol, tetracycline hydrochloride, lamin and kinetin; retinoids for treating skin cancer, e.g., retinol, tretinoin, isotretinoin, etretinate, acitretin, and arotinoid; mild antibacterial agents for treating skin infections, e.g., resorcinol, salicylic acid, benzoyl peroxide, erythromycin-benzoyl peroxide, erythromycin, and clindamycin; antifungal agents for treating tinea corporis, tinea pedis, candidiasis and tinea versicolor, e.g., griseofulvin, azoles such as miconazole, econazole, itraconazole, fluconazole, and ketoconazole, and allylamines such as naftifine and terfinafine; antiviral agents for treating cutaneous herpes simplex, herpes zoster, and chickenpox, e.g., acyclovir, famciclovir, and valacyclovir; antihistamines for treating pruritis, atopic and contact dermatitis, e.g., diphenhydramine, terfenadine, asternizole, loratadine, cetirizi, ne, acrivastine, and temelastine; topical anesthetics for relieving pain, irritation and itching, e.g., benzocaine, lidocaine, dibucaine, and pramoxine hydrochloride; topical analgesics for relieving pain and inflammation, e.g., methyl salicylate, camphor, menthol, and resorcinol; topical antiseptics for preventing infection, e.g., benzalkonium chloride and povidone-iodine; and vitamins and derivatives thereof such as tocopherol, tocopherol acetate, retinoic acid and retinol.

Dispersing and suspending agents are used as aids for the preparation of stable formulations and include, e.g., poligeenan, povidone, and silicon dioxide.

Emollients are agents, preferably non-oily and water-soluble, which soften and soothe the skin, especially skin that has become dry because of excessive loss of water. Such agents are used with pharmaceutical compositions of the present invention which are intended for topical applications, and include, e.g., hydrocarbon oils and waxes, triglyceride esters, acetylated monoglycerides, methyl and other alkyl esters of $C_{10}$-$C_{20}$ fatty acids, $C_{10}$-$C_{20}$ fatty acids, $C_{10}$-$C_{20}$ fatty alcohols, lanolin and derivatives, polyhydric alcohol esters such as polyethylene glycol (200-600), polyoxyethylene sorbitan fatty acid esters, wax esters, phospholipids, and sterols; emulsifying agents used for preparing oil-in-water emulsions; excipients, e.g., laurocapram and polyethylene glycol monomethyl ether; humectants, e.g., sorbitol, glycerin and hyaluronic acid; ointment bases, e.g., petrolatum, polyethylene glycol, lanolin, and poloxamer; penetration enhancers, e.g., dimethyl isosorbide, diethyl-glycol monoethylether, 1-dodecylazacycloheptan-2-one, and dimethylsulfoxide (DMSO); preservatives, e.g., benzalkonium chloride, benzethonium chloride, alkyl esters of p hydroxybenzoic acid, hydantoin derivatives, cetylpyridinium chloride, propylparaben, quaternary ammonium compounds such as potassium benzoate, and thimerosal; sequestering agents comprising cyclodextrins; solvents, e.g., acetone, alcohol, amylene hydrate, butyl alcohol, corn oil, cottonseed oil, ethyl acetate, glycerin, hexylene glycol, isopropyl alcohol, isostearyl alcohol, methyl alcohol, methylene chloride, mineral oil, peanut oil, phosphoric acid, polyethylene glycol, polyoxypropylene 15 stearyl ether, propylene glycol, propylene glycol diacetate, sesame oil, and purified water; stabilizers, e.g., calcium saccharate and thymol; surfactants, e.g., lapyrium chloride; laureth 4, ie., $\alpha$-dodecyl-$\omega$-hydroxy-poly(oxy-1,2-ethanediyl) or polyethylene glycol monododecyl ether.

Emulsifying agents, including emulsifying and stiffening agents and emulsion adjuncts, are used for preparing oil-in-water emulsions when these form the basis of the pharmaceutical compositions of the present invention. Such emulsifying agents include, e.g., non-ionic emulsifiers such as $C_{10}$-$C_{20}$ fatty alcohols and said fatty alcohols condensed with from 2 to 20 moles of ethylene oxide or propylene oxide, ($C_6$-$C_{12}$)alkyl phenols condensed with from 2 to 20 moles of ethylene oxide, mono- and di-$C_{10}$-$C_{20}$ fatty acid esters of ethylene glycol, $C_{10}$-$C_{20}$ fatty acid monoglyceride, diethylene glycol, polyethylene glycols of MW 200-6000, polypropylene glycols of MW 200-3000, and particularly sorbitol, sorbitan, polyoxyethylene sorbitol, polyoxyethylene sorbitan, hydrophilic wax esters, cetostearyl alcohol, oleyl alcohol, lanolin alcohols, cholesterol, mono- and diglycerides, glyceryl monostearate, polyethylene glycol monostearate, mixed mono- and distearic esters of ethylene glycol and polyoxyethylene glycol, propylene glycol monostearate, and hydroxypropyl cellulose. Emulsifying agents which contain active amine groups may also be used and typically include anionic emulsifiers such as fatty acid soaps, e.g., sodium, potassium and triethanolamine soaps of $C_{10}$-$C_{20}$ fatty acids; alkali metal, ammonium or substituted ammonium ($C_{10}$-$C_{30}$)alkyl sulfates, ($C_{10}$-$C_{30}$)alkyl sulfonates, and ($C_{10}$-$C_{50}$)alkyl ethoxy ether sulfonates. Other suitable emulsifying agents include castor oil and hydrogenated castor oil; lecithin; and polymers of 2-propenoic acid together with polymers of acrylic acid, both cross-linked with allyl ethers of sucrose and/or pentaerythritol, having varying viscosities and identified by product names carbomer 910, 934, 934P, 940, 941, and 1342. Cationic emulsifiers having active amine groups may also be used, including those based on quaternary ammonium, morpholinium and pyridinium compounds. Similarly, amphoteric emulsifiers having active amine groups, such as cocobetaines, lauryl dimethylamine oxide and cocoylimidazoline, may be used. Useful emulsifying and stiffening agents also include cetyl alcohol and sodium stearate; and emulsion adjuncts such as oleic acid, stearic acid, and stearyl alcohol.

Excipients include, e.g., laurocapram and polyethylene glycol monomethyl ether.

Where the pharmaceutical composition of the present invention is to be applied topically, penetration enhancers may be used, which include, e.g., dimethyl isosorbide, diethyl-glycol-monoethylether, 1-dodecylazacycloheptan-2-one, and dimethylsulfoxide (DMSO). Such compositions will also typically include ointment bases, e.g., petrolatum, polyethylene glycol, lanolin, and poloxamer, which is a block copolymer of polyoxyethylene and polyoxypropylene, which may also serve as a surfactant or emulsifying agent.

Preservatives are used to protect pharmaceutical compositions of the present invention from degradative attack by ambient microorganisms, and include, e.g., benzalkonium chloride, benzethonium chloride, alkyl esters of p-hydroxybenzoic acid, hydantoin derivatives, cetylpyridinium chloride, monothioglycerol, phenol, phenoxyethanol, methylparagen, imidazolidinyl urea, sodium dehydroacetate, propylparaben, quaternary ammonium compounds, especially polymers such as polixetonium chloride, potassium benzoate, sodium formaldehyde sulfoxylate, sodium propionate, and thimerosal.

Sequestering agents are used to improve the stability of the pharmaceutical compositions of the present invention and include, e.g., the cyclodextrins which are a family of natural cyclic oligosaccharides capable of forming inclusion complexes with a variety of materials, and are of varying ring sizes, those having 6-, 7- and 8-glucose residues in a ring being commonly referred to as $\alpha$-cyclodextrins, $\beta$-cyclodextrins, and $\gamma$-cyclodextrins, respectively. Suitable cyclodextrins include, e.g., $\alpha$-cyclodextrin, $\beta$-cyclodextrin, $\gamma$-cyclodextrin, $\delta$-cyclodextrin and cationized cyclodextrins.

Solvents which may be used in preparing the pharmaceutical compositions of the present invention include, e.g., acetone, alcohol, amylene hydrate, butyl alcohol, corn oil, cottonseed oil, ethyl acetate, glycerin, hexylene glycol, isopropyl alcohol, isostearyl alcohol, methyl alcohol, methylene chloride, mineral oil, peanut oil, phosphoric acid, polyethylene glycol, polyoxypropylene 15 stearyl ether, propylene glycol, propylene glycol diacetate, sesame oil, and purified water.

Stabilizers which are suitable for use include, e.g., calcium saccharate and thymol.

Stiffening agents are typically used in formulations for topical applications in order to provide desired viscosity and handling characteristics and include, e.g., cetyl esters wax, myristyl alcohol, parafin, synthetic parafin, emulsifying wax, microcrystalline wax, white wax and yellow wax.

Sugars are often used to impart a variety of desired characteristics to the pharmaceutical compositions of the present invention and in order to improve the results obtained, and include, e.g., monosaccharides, disaccharides and polysaccharides such as glucose, xylose, fructose, reose, ribose, pentose, arabinose, allose, tallose, altrose, mannose, galactose, lactose, sucrose, erythrose, glyceraldehyde, or any combination thereof.

Surfactants are employed to provide stability for multi-component pharmaceutical compositions of the present invention, enhance existing properties of those compositions, and bestow desirable new characteristics on said compositions. Surfactants are used as wetting agents, antifoam agents, for reducing the surface tension of water, and as emulsifiers, dispersing agents and penetrants, and include, e.g., lapyrium chloride; laureth 4, i.e., α-dodecyl-ω-hydroxy-poly(oxy-1,2-ethanediyl) or polyethylene glycol monododecyl ether; laureth 9, i.e., a mixture of polyethylene glycol monododecyl ethers averaging about 9 ethylene oxide groups per molecule; monoethanolamine; nonoxynol 4, 9 and 10, i.e., polyethylene glycol mono(p-nonylphenyl) ether; nonoxynol 15, i. e., α-(p-nonylphenyl)-ω-hydroxy-penta-deca(oxyethylene); nonoxynol 30, i.e., α-(p-nonylphenyl)-ω-hydroxytriaconta(oxyethylene); poloxalene, i.e., nonionic polymer of the polyethylenepolypropylene glycol type, MW=approx. 3000; poloxamer, referred to in the discussion of ointment bases further above; polyoxyl 8, 40 and 50 stearate, i.e., poly(oxy-1,2-ethanediyl), α-hydro-ω-hydroxy-; octadecanoate; polyoxyl 10 oleyl ether, i.e., poly(oxy-1,2-ethanediyl), α-[(Z)-9-octadecenyl-ω-hydroxy-; polysorbate 20, i.e., sorbitan, monododecanoate, poly(oxy-1,2-ethanediyl); polysorbate 40, i.e., sorbitan, monohexadecanoate, poly(oxy-1,2-ethanediyl); polysorbate 60, i.e., sorbitan, monooctadecanoate, poly(oxy-1,2-ethanediyl); polysorbate 65, i.e., sorbitan, trioctadecanoate, poly(oxy-1,2-ethanediyl); polysorbate 80, i.e., sorbitan, mono-9-monodecenoate, poly(oxy-1,2-ethanediyl); polysorbate 85, i.e., sorbitan, tri-9-octadecenoate, poly(oxy-1,2-ethanediyl); sodium lauryl sulfate; sorbitan monolaurate; sorbitan monooleate; sorbitan monopalmitate; sorbitan monostearate; sorbitan sesquioleate; sorbitan trioleate; and sorbitan tristearate.

The pharmaceutical compositions of the present invention may be prepared using very straightforward methodology which is well understood by the artisan of ordinary skill. Where the pharmaceutical compositions of the present invention are simple aqueous and/or other solvent solutions, the various components of the overall composition are brought together in any practical order, which will be dictated largely by considerations of convenience. Those components having reduced water solubility, but sufficient solubility in the same co-solvent with water, may all be dissolved in said co-solvent, after which the co-solvent solution will be added to the water portion of the carrier whereupon the solutes therein will become dissolved in the water. To aid in this dispersion/solution process, a surfactant may be employed.

Where the pharmaceutical compositions of the present invention are to be in the form of emulsions, the components of the pharmaceutical composition will be brought together in accordance with the following general procedures. The continuous water phase is first heated to a temperature in the range of from about 60° to about 95° C., preferably from about 70° to about 85° C., the choice of which temperature to use being dependent upon the physical and chemical properties of the components which make up the oil-in-water emulsion. Once the continuous water phase has reached its selected temperature, the components of the final composition to be added at this stage are admixed with the water and dispersed therein under high-speed agitation. Next, the temperature of the water is restored to approximately its original level, after which the components of the composition which comprise the next stage are added to the composition mixture under moderate agitation and mixing continues for from about 5 to about 60 minutes, preferably about 10 to about 30 minutes, depending on the components of the first two stages. Thereafter, the composition mixture is passively or actively cooled to from about 20° to about 55° C. for addition of any components in the remaining stages, after which water is added in sufficient quantity to reach its original predetermined concentration in the overall composition.

According to the present invention, the pharmaceutical compositions may be in the form of a sterile injectable preparation, for example a sterile injectable aqueous or oleaginous suspension. This suspension may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as do natural pharmaceutically acceptable oils, such as olive oil or castor oil, especially in their polyoxyethylated versions. These oil solutions or suspensions may also contain a long-chain alcohol diluent or dispersant, such as Rh, HCIX or similar alcohol.

The pharmaceutical compositions of the present invention may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added. Alternatively, the pharmaceutical compositions of this invention may be administered in the form of suppositories for rectal administration. These can be prepared by mixing the agent with a suitable non-irritating excipient which is solid at room temperature but liquid at the rectal temperature and therefore will melt in the rectum to release the drug. Such materials include cocoa butter, beeswax and polyethylene glycols.

The pharmaceutical compositions of the present invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation, as described above, or in a suitable enema formulation. Topically active transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate, cetyl esters wax, cetearyl alcohol, 2-octyldodecanol, benzyl alcohol and water.

Pharmaceutical compositions within the scope of the present invention include those wherein the therapeutically effective amount of an active ingredient comprising a preferred compound required for treating or preventing diseases, disorders, and conditions mediated by or associated with modulation of PDE IV activity as described herein, is provided in a dosage form suitable for systemic administration. Such a pharmaceutical composition will contain said active ingredient in suitable liquid form for delivery by: (1) injection or infusion which is intraarterial, intra- or transdermal, subcutaneous, intramuscular, intraspinal, intrathecal, or intravenous, wherein said active ingredient: (a) is contained in solution as a solute; (b) is contained in the discontinuous phase of an emulsion, or the discontinuous phase of an inverse emulsion which inverts upon injection or infusion, said emulsions containing suitable emulsifying agents; or (c) is contained in a suspension as a suspended solid in colloidal or microparticulate form, said suspension containing suitable suspending agents; (2) injection or infusion into suitable body tissues or cavities as a depot, wherein said composition provides storage of said active ingredient and thereafter delayed-, sustained-, and/or controlled-release of said active ingredient for systemic distribution; (3) instillation, inhalation or insufflation into suitable body tissues or cavities of said pharmaceutical composition in suitable solid form, where said active ingredient: (a) is contained in a solid implant composition providing delayed-, sustained-, and/or controlled-release of said active ingredient; (b) is contained in a particulate composition to be inhaled into the lungs; or (c) is contained in a particulate composition to be blown into suitable body tissues or cavities, where said composition optionally provides delayed-, sustained-, and/or controlled-release of said active ingredient; or (4) ingestion of said pharmaceutical composition in suitable solid or liquid form for peroral delivery of said active ingredient, where said active ingredient is contained in a solid dosage form; or (b) is contained in a liquid dosage form.

Particular dosage forms of the above-described pharmaceutical compositions include (1) suppositories as a special type of implant, comprising bases which are solid at room temperature but melt at body temperature, slowly releasing the active ingredient with which they are impregnated into the surrounding tissue of the body, where the active ingredient becomes absorbed and transported to effect systemic administration; (2) solid peroral dosage forms selected from the group consisting of (a) delayed-release oral tablets, capsules, caplets, lozenges, troches, and multiparticulates; (b) enteric-coated tablets and capsules which prevent release and absorption in the stomach to facilitate delivery distal to the stomach of the patient being treated; (c) sustained-release oral tablets, capsules and microparticulates which provide systemic delivery of the active ingredient in a controlled manner up to a 24-hour period; (d) fast-dissolving tablets; (e) encapsulated solutions; (f) an oral paste; (g) a granular form incorporated in or to be incorporated in the food of a patient being treated; and (h) liquid peroral dosage forms selected from the group consisting of solutions, suspensions, emulsions, inverse emulsions, elixirs, extracts, tinctures, and concentrates.

Pharmaceutical compositions within the scope of the present invention include those wherein the therapeutically effective amount of an active ingredient comprising a compound of the present invention required for treating or preventing diseases, disorders, and conditions mediated by or associated with modulation of PDE IV activity as described herein is provided in a dosage form suitable for local administration to a patient being treated, wherein said pharmaceutical composition contains said active ingredient in suitable liquid form for delivering said active ingredient by: (1) injection or infusion into a local site which is intraarterial, intraarticular, intrachondrial, intracostal, intracystic, intra- or transdermal, intrafasicular, intraligamentous, intramedulary, intramuscular, intranasal, intraneural, intraocular, i.e., opthalmic administration, intraosteal, intrapelvic, intrapericardial, intraspinal, intrasternal, intrasynovial, intratarsal, or intrathecal; including components which provide delayed-release, controlled-release, and/or sustained-release of said active ingredient into said local site; where said active ingredient is contained: (a) in solution as a solute; (b) in the discontinuous phase of an emulsion, or the discontinuous phase of an inverse emulsion which inverts upon injection or infusion, said emulsions containing suitable emulsifying agents; or (c) in a suspension as a suspended solid in colloidal or microparticulate form, said suspension containing suitable suspending agents; or (2) injection or infusion as a depot for delivering said active ingredient to said local site; wherein said composition provides storage of said active ingredient and thereafter delayed-, sustained-, and/or controlled-release of said active ingredient into said local site, and wherein said composition also includes components which ensure that said active ingredient has predominantly local activity, with little systemic carryover activity; or wherein said pharmaceutical composition contains said active ingredient in suitable solid form for delivering said inhibitor by: (3) instillation, inhalation or insufflation to said local site, where said active ingredient is contained: (a) in a solid implant composition which is installed in said local site, said composition optionally providing delayed-, sustained-, and/or controlled-release of said active ingredient to said local site; (b) in a particulate composition which is inhaled into a local site comprising the lungs; or (c) in a particulate composition which is blown into a local site, where said composition includes components which will ensure that said active ingredient has predominantly local activity, with insignificant sys temic carryover activity, and optionally provides delayed-, sustained-, and/or controlled release of said active ingredient to said local site. For ophthalmic use, the pharmaceutical compositions may be formulated as micronized suspension in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of the present invention may also be administered by nasal aerosol or inhalation through the use of a nebulizer, a dry powder inhaler or a metered dose inhaler. Such compositions are prepared according to techniques well-known in the art of pharmaceutical formulation and may be prepared as solutions in saline, employing benzyl alcohol or other suitable preservatives, absorption promoters to enhance bioavailability, hydrofluorocarbons, and/or other conventional solubilizing or dispersing agents.

As already mentioned, the preferred compounds of the present invention may be administered systemically to a patient to be treated as a pharmaceutical composition in suitable liquid form by injection or infusion. There are a number of sites and organ systems in the body of the patient which will allow the properly formulated pharmaceutical composition, once injected or infused, to permeate the entire body and all of the organ system of the patient being treated.

An injection is a single dose of the pharmaceutical composition forced, usually by a syringe, into the tissue involved. The most common types of injections are intramuscular, intravenous, and subcutaneous. By contrast, an infusion is the gradual introduction of the pharmaceutical composition into the tissue involved. The most common type of infusion is intravenous. Other types of injection or infusion comprise intraarterial, intra- or transdermal (including subcutaneous), or intraspinal especially intrathecal. In these liquid pharmaceutical compositions, the active ingredient may be contained in solution as the solute. This is the most common and most preferred type of such composition, but requires an active ingredient in a salt form that has reasonably good aqueous solubility. Water (or saline) is by far the most preferred solvent for such compositions. Occasionally supersaturated solutions may be utilized, but these present stability problems that make them impractical for use on an everyday basis.

If it is not possible to obtain a form of some preferred compound that has the requisite degree of aqueous solubility, as may sometimes occur, it is, within the skill of the artisan to prepare an emulsion, which is a dispersion of small globules of one liquid, the discontinuous or internal phase, throughout a second liquid, the continuous or external phase, with which it is immiscible. The two liquids are maintained in an emulsified state by the use of emulsifiers which are pharmaceutically acceptable. Thus, if the active ingredient is a water-insoluble oil, it can be administered in, an emulsion of which it is the discontinuous phase. Also where the active ingredient is water-insoluble but can be dissolved in a solvent which is immiscible with water, an emulsion can be used. While the active ingredient would most commonly be used as the discontinuous or internal phase of what is referred to as an oil-in-water emulsion, it could also be used as the discontinuous or internal phase of an inverse emulsion, which is commonly referred to as a water-in-oil emulsion. Here the active ingredient is soluble in water and could be administered as a simple aqueous solution. However, inverse emulsions invert upon injection or infusion into an aqueous medium such as the blood, and offer the advantage of providing a more rapid and efficient dispersion of the active ingredient into that aqueous medium than can be obtained using an aqueous solution. Inverse emulsions are prepared by using suitable, pharmaceutically acceptable emulsifying agents well known in the art. Where the active ingredient has limited water solubility, it may also be administered as a suspended solid in colloidal or microparticulate form in a suspension prepared using suitable, pharmaceutically acceptable suspending agents. The suspended solids containing the active ingredient may also be formulated as delayed-, sustained-, and/or controlled-release compositions.

While systemic administration will most frequently be carried out by injection or infusion of a liquid, there are many situations in which it will be advantageous or even necessary to deliver the active ingredient as a solid. Systemic administration of solids is carried out by instillation, inhalation or insufflation of a pharmaceutical composition in suitable solid form containing the active ingredient. Instillation of the active ingredient may entail installing a solid implant composition into suitable body tissues or cavities. The implant may comprise a matrix of bio-compatible and bio-erodible materials in which particles of a solid active ingredient are dispersed, or in which, possibly, globules or isolated cells of a liquid active ingredient are entrapped. Desirably, the matrix will be broken down and completely absorbed by the body. The composition of the matrix is also preferably selected to provide controlled-, sustained-, and/or delayed release of the active ingredient over extended periods of time, even as much as several months.

The term "implant" most often denotes a solid pharmaceutical composition containing the active ingredient, while the term "depot" usually implies a liquid pharmaceutical composition containing the active ingredient, which is deposited in any suitable body tissues or cavities to form a reservoir or pool which slowly migrates to surrounding tissues and organs and eventually becomes systemically distributed. However, these distinctions are not always rigidly adhered to in the art, and consequently, it is contemplated that there is included within the scope of the present invention liquid implants and solid depots, and even mixed solid and liquid forms for each. Suppositories may be regarded as a type of implant, since they comprise bases which are solid at room temperature but melt at a patient's body temperature, slowly releasing the active ingredient with which they are impregnated into the surrounding tissue of the patient's body, where the active ingredient becomes absorbed and transported to effect systemic administration.

Systemic administration can also be accomplished by inhalation or insufflation of a powder, i.e., particulate composition containing the active ingredient. For example, the active ingredient in powder form may be inhaled into the lungs using conventional devices for aerosolizing particulate formulations. The active ingredient as a particulate formulation may also be administered by insufflation, i.e., blown or otherwise dispersed into suitable body tissues or cavities by simple dusting or using conventional devices for aerosolizing particulate formulations. These particulate compositions may also be formulated to provide delayed-, sustained-, and/or controlled-release of the active ingredient in accordance with well understood principles and known materials.

Other means of systemic administration which may utilize the active ingredients of the present invention in either liquid or solid form include transdermal, intranasal, and opthalmic routes. In particular, transdermal patches prepared in accordance with well known drug delivery technology may be prepared and applied to the skin of a patient to be treated, whereafter the active-agent by reason of its formulated solubility characteristics migrates across the epidermis and info the dermal layers of the patient's skin where it is taken up as part of the general circulation of the patient, ultimately providing systemic distribution of the active ingredient over a desired, extended period of time. Also included are implants which are placed beneath the epidermal layer of the skin, i. e. between the epidermis and the dermis of the skin of the patient being treated. Such an implant will be formulated in accordance with well known principles and materials commonly used in this delivery technology, and may be prepared in such a way as to provide controlled-, sustained-, and/or delayed-release of the active ingredient into the systemic circulation of the patient. Such subepidermal (subcuticular) implants provide the same facility of installation and delivery efficiency as transdermal patches, but without the limitation of being subject to degradation, damage or accidental removal as a consequence of being exposed on the top layer of the patient's skin.

In the above description of pharmaceutical compositions containing a preferred compound, the equivalent expressions: "administration", "administration of", "administering", and "administering a" have been used with respect to said pharmaceutical compositions. As thus employed, these expressions are intended to mean providing to a patient in need of treatment a pharmaceutical composition of the present invention by any of the routes of administration herein described, wherein the active ingredient is a preferred compound or a prodrug, derivative, or metabolite thereof which is useful in treating a disease, disorder, or condition mediated by or associated with modulation of PDE IV activity in said patient. Accordingly, there is included within the scope of the present invention any other compound which, upon administration to a patient, is capable of directly or indirectly providing a preferred compound. Such compounds are recognized as prodrugs, and a number of established procedures are available for preparing such prodrug forms of the preferred compounds.

The dosage and dose rate of the compounds effective for treating or preventing, a disease, disorder, or condition mediated by or associated with modulation of PDE IV activity, will depend on a variety of factors, such as the nature of the inhibitor, the size of the patient, the goal of the treatment, the nature of the pathology to be treated, the specific pharmaceutical composition used, and the observations and conclusions of the treating physician.

For example, where the dosage form is oral, e.g., a tablet or capsule, suitable dosage levels of the preferred compounds will be between about 0.1 µg/kg and about 50.0 mg/kg of body weight per day, preferably between about 5.0 µg/kg and about 5.0 mg/kg of body weight per day, more preferably between about 10.0 µg/kg and about 1.0 mg/kg of body weight per day, and most preferably between about 20.0 µg/kg and about 0.5 mg/kg of body weight per day of the active ingredient.

Where the dosage form is topically administered to the bronchia and lungs, e.g., by means of a powder inhaler or nebulizer, suitable dosage levels of the compounds will be between about 0.001 µg/kg and about 10.0 mg/kg of body weight per day, preferably between about 0.5 µg/kg and about 0.5 mg/kg of body weight per day, more preferably between about 1.0 µg/kg and about 0.1 mg/kg of body weight per day, and most preferably between about 2.0 µg/kg and about 0.05 mg/kg of body weight per day of the active ingredient.

Using representative body weights of 10 kg and 100 kg in order to illustrate the range of daily oral dosages which might be used as described above, suitable dosage levels of the preferred compounds will be between about 1.0-10.0 µg and 500.0-5000.0 mg per day, preferably between about 50.0-500.0 µg and 50.0-500.0 mg per day, more preferably between about 100.0-1000.0 µg and 10.0-100.0 mg per day, and most preferably between about 200.0-2000.0 µg and about 5.0-50.0 mg per day of the active ingredient comprising a preferred compound. These ranges of dosage amounts represent total dosage amounts of the active ingredient per day for a given patient. The number of times per day that a dose is administered will depend upon such pharmacological and pharmacokinetic factors as the half-life of the active ingredient, which reflects its rate of catabolism and clearance, as well as the minimal and optimal blood plasma or other body fluid levels of said active ingredient attained in the patient which are required for therapeutic efficacy.

Numerous other factors must also be considered in deciding upon the number of doses per day and the amount of active ingredient per dose that will be administered. Not the least important of such other factors is the individual responsse of the patient being treated. Thus, for example, where the active ingredient is used to treat or prevent asthma, and is administered topically via aerosol inhalation into the lungs, from one to four doses consisting of acuations of a dispensing device, i.e., "puffs" of an inhaler, will be administered. each day, each dose containing from about 50.0 µg to about 10.0 mg of active ingredient.

The invention also relates to a set (kit) consisting of separate packs of
(a) an effective amount of a compound of the formula I and/or its pharmaceutically usable derivatives, solvates and stereoisomers, including mixtures thereof in all ratios, and
(b) an effective amount of a further medicament active ingredient.

The set comprises suitable containers, such as boxes, individual bottles, bags or ampoules. The set may, for example, comprise separate ampoules each containing an effective amount of a compound of the formula I and/or its pharmaceutically usable derivatives, solvates and stereoisomers, including mixtures thereof in all ratios, and an effective amount of a further medicament active ingredient in dissolved or lyophilised form.

The compounds of the formula I and the physiologically acceptable salts and solvates thereof can be employed preferably for combating diseases which are caused by an excessively low cAMP (cycloadenosine monophosphate) level and/or can be influenced by an increase in the cAMP level. The increased cAMP level causes inhibition or prevention of inflammation and causes muscle relaxation. In particular, the PDE IV inhibitors according to the invention can be used in the treatment of allergic diseases, asthma, chronic bronchitis, atopic dermatitis, psoriasis and other skin diseases, inflammatory disorders, autoimmune diseases, such as, for example, rheumatoid arthritis, multiple sclerosis, Crohn's disease, diabetes mellitus or ulcerative colitis, osteoporosis, transplant rejection reactions, cachexia, tumour growth or tumour metastases, sepsis, memory disorders, atherosclerosis and AIDS.

In general, the substances according to the invention are preferably administered in doses corresponding to the compound rolipram of between 1 and 500 mg, in particular between 5 and 100 mg per dosage unit. The daily dose is preferably between about 0.02 and 10 mg/kg of body weight. However, the specific dose for each patient depends on a wide variety of factors, for example on the efficacy of the specific compound employed, on the age, body weight, general state of health, sex, on the diet, on the time and method of administration, on the excretion rate, medicament combination and severity of the particular illness to which the therapy applies. Oral administration is preferred.

EXAMPLE I

Effect of the Compounds of Formula I on T-Cell Proliferation

Peripheral blood mononuclear cells (PBMC) are isolated from the blood of healthy donors by the Lymphoprep gradient method. 200000 PBMC/well are cultured in RPMI1640 culture medium containing 5% heat inactivated human serum (AB pool) for 5 days at 37° C. and 10% $CO_2$ in 96 well flat bottom microtiter plates. The T cells within the PBMC preparation are selectively stimulated with an monoclonal antibody to CD3. Cultures are set up as triplicates including a control group receiving no treatment. The compounds of formula I are dissolved in DMSO at $10^{-2}$ M and diluted in culture medium. Control cultures are treated with DMSO equivalent to the inhibitor concentration. 18 hrs before the end of the assay, $^3$H-thymidine is added to the cultures. The incorporation of radioactivity into the cells is then measured in a beta-counter.

The data of at least three independent experiments are calculated as percent inhibition of the control (mean±SEM) without inhibitor. From this data the IC-50 value is determined.

Results:

The compounds of formula I afford a marked reduction of T-cell proliferation.

EXAMPLE II

Effect of the Compounds of Formula I on Cytokine Production in Human Peripheral Blood Monocytic Cells Peripheral blood mononuclear cells (PBMC) are isolated from the blood of healthy donors by the Lymphoprep gradient method. 200000 PBMC/well are cultured in RPMI1640 culture medium containing 5% heat inactivated human serum (AB pool). at 37° C. and 10% $CO_2$ in 96 well flat bottom microtiter plates. Cultures are set up as triplicates including a control group. Solutions of the compounds of formula I are prepared in DMSO at $10^{-2}$ M and diluted in culture medium. Control cultures are treated with concentrations of DMSO equivalent to the inhibitor concentrations. The culture supernatants of three independent experiments are pooled and cytokine activity in the supernatant is measured with commercially available ELISA test kits.

The data are calculated as percent inhibition/stimulation of the control without the compound and the $IC_{50}$ value or $EC_{50}$ value in case of stimulation is determined thereof.

Result

The compounds of formula I afford a marked reduction in the release of IL-2, IFN-γ, TNF-α and IL-12. The immunosuppressant cytokine IL-10, however, is stimulated.

EXAMPLE III

Effect of the Compounds of Formula I on Experimental Myocardial Infarction in Rats The compounds of formula I, administered intraperitoneally with 1, 3, and 10 mg/kg, 1 hour before reversible occlusion of the left coronary artery in rats cause a significant dose dependent reduction of infarct size. In correspondence with this protection, a reduction of plasma TNF-α levels is observed, as measured by ELISA.

EXAMPLE IV

Effect of the Compounds of Formula I on Experimental Myocardial Infarction in Rabbits There is a cardioprotective effect by PDE IV inhibition in anaesthetised rabbits subjected to 30 minutes of coronary artery occlusion (side branch of the ramus circumflexus of the left coronary artery) followed by 120 minutes of reperfusion. Compounds of formula I applied prior to the coronary occlusion, reduce infarct size as compared with placebo treatment. The areas at risk are comparable between verum and placebo groups. The cardioprotective effect cannot be attributed to favorable hemodynamic effects, since heart rate and mean aortic pressure remain constant throughout the experimental protocol.

Above and below, all temperatures are given in ° C. In the following examples, "conventional work-up" means that water is added if necessary, the pH is adjusted, if necessary, to between 2 and 10, depending on the constitution of the end product, the mixture is extracted with ethyl acetate or dichloromethane, the phases are separated, the organic phase is dried over sodium sulfate and evaporated, and the product is purified by chromatography on silica gel and/or by crystallisation.

EXAMPLE 1

Step A:

A solution of 2.10 l of iodoethane in 6.0 l of diethyl ether was added dropwise to a mixture of 4.00 kg of isovanilin and 10.50 kg of potassium carbonate in 32.5 l of acetonitrile. The mixture was stirred overnight and subjected to conventional work-up, giving 3.

Step B:

1.10 kg of sodium cyanide are introduced into a solution of 3.00 kg of 3, 3.15 l of morpholine and 3.42 kg of toluene-4-sulfonic acid in 18 l of THF. The mixture was stirred overnight and subjected to conventional work-up, giving 6.

Step C:

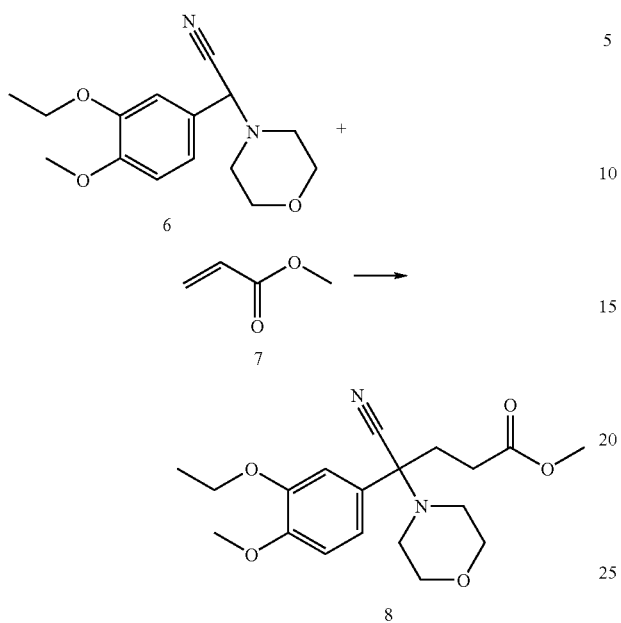

A solution of 0.064 kg of sodium in 1.30 l of methanol was added to 3.840 kg of 6. A mixture of 1.385 l of methyl acrylate in 13.0 l of tetrahydro-furan was subsequently added dropwise, and the mixture was stirred overnight. Conventional work-up gave 8.

Step D:

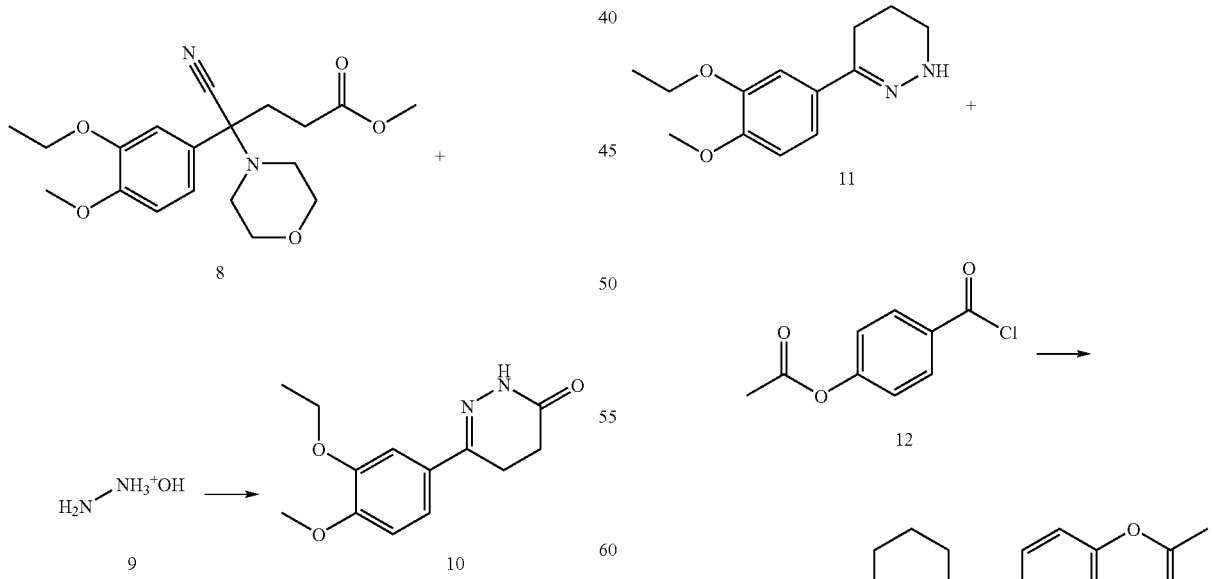

4.80 kg of 8 are dissolved in 14.0 l of ethanol, and 850.0 ml of hydrazinium hydroxide are added. The mixture was stirred overnight and subjected to conventional work-up, giving 10.

Step E:

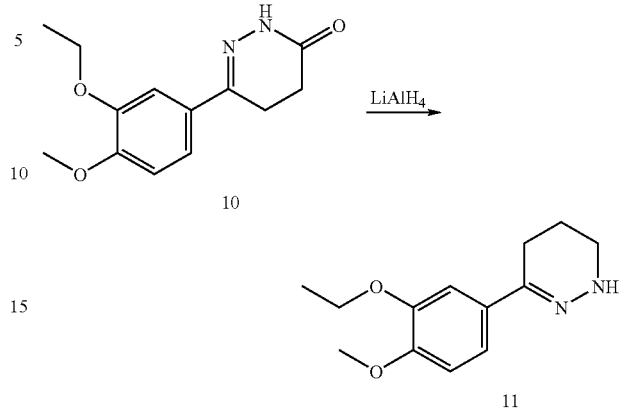

2 l of THF are allowed to reaction into a suspension of 40.00 g of lithium aluminium hydride in 100 ml of toluene over the course of 10 minutes. When the exothermicity had subsided, 250.00 g of 10 in 2 l of THF are added dropwise with stirring and ice-cooling at 0-5° C. The mixture was stirred for 18 hours at RT, and 100 ml of water are added dropwise with stirring and cooling. When the hydrolysis was complete, a solution of 500 g of sodium carbonate decahydrate and 200 ml of water at 80° C. was allowed to run in rapidly. After brief stirring, the batch was filtered with suction, and the filtrate was subjected to conventional work-up, giving 11 (m.p: 101-103° C.).

Step F:

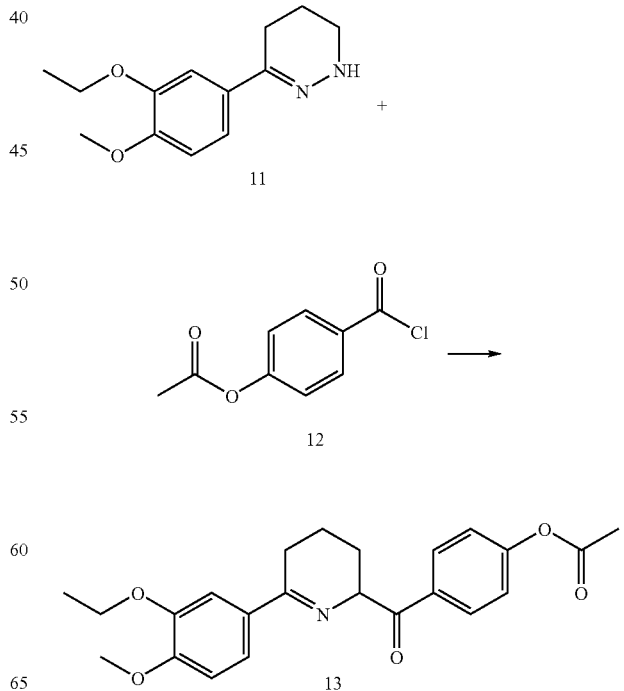

165.00 g of 11 and 80.71 ml of pyridine are dissolved in dichloromethane. 156.90 g of 12, dissolved in 100 ml of dichloromethane, are added dropwise at 10-15° C., and the batch was stirred overnight at 15-20° C. Conventional work-up gave 13 in crystalline form.

Step G:

106.00 mg of 14, 0.055 ml of triethylene glycol monomethyl ether and 250.00 mg of triphenylphosphine (polymeric) are introduced into CH$_2$Cl$_2$, and 141.00 mg of di-tert-butyl azodicarboxylate are introduced at RT with stirring. The mixture was stirred overnight at RT and subjected to conventional work-up, giving 16.

EXAMPLE 2

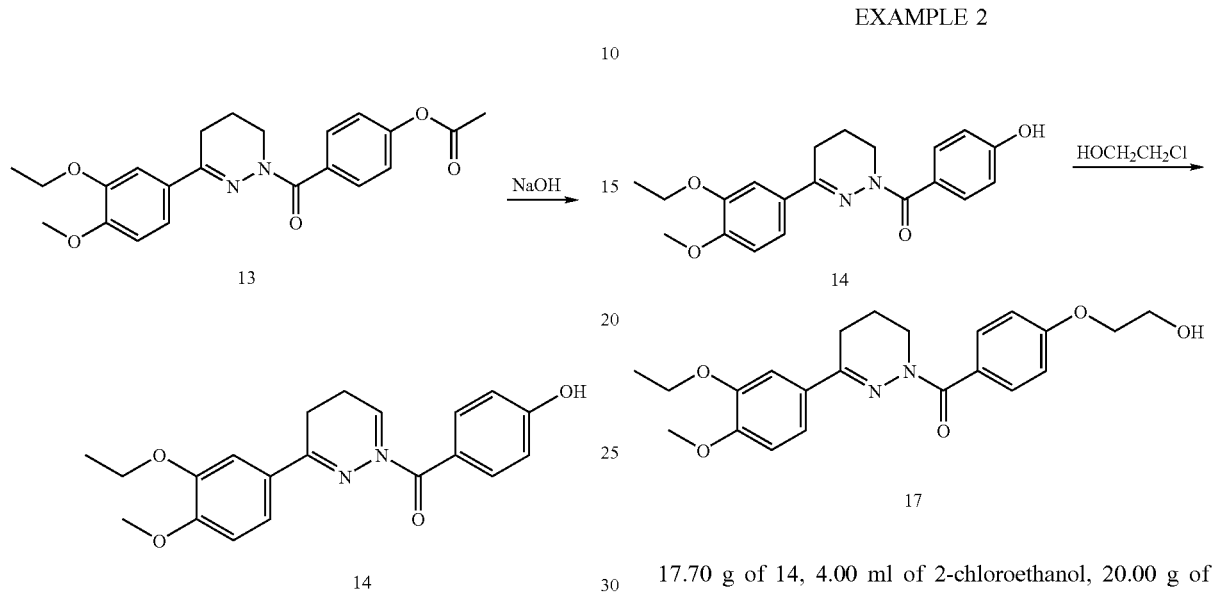

195.00 g of 13 are introduced into 1.2 l of ethanol at 19° C., and 1.2 l of a 2M sodium hydroxide solution are added. The mixture was stirred overnight at RT. Conventional work-up gave 14 as a crystalline solid.

Step H:

17.70 g of 14, 4.00 ml of 2-chloroethanol, 20.00 g of potassium carbonate and 20.00 ml of dimethylformamide are combined and stirred overnight at 120° C. Water was added to the mixture, and precipitated material was filtered off with suction. Crystallisation of the residue from ethanol gave 17.

The following compounds are obtained analogously using the corresponding precursors:

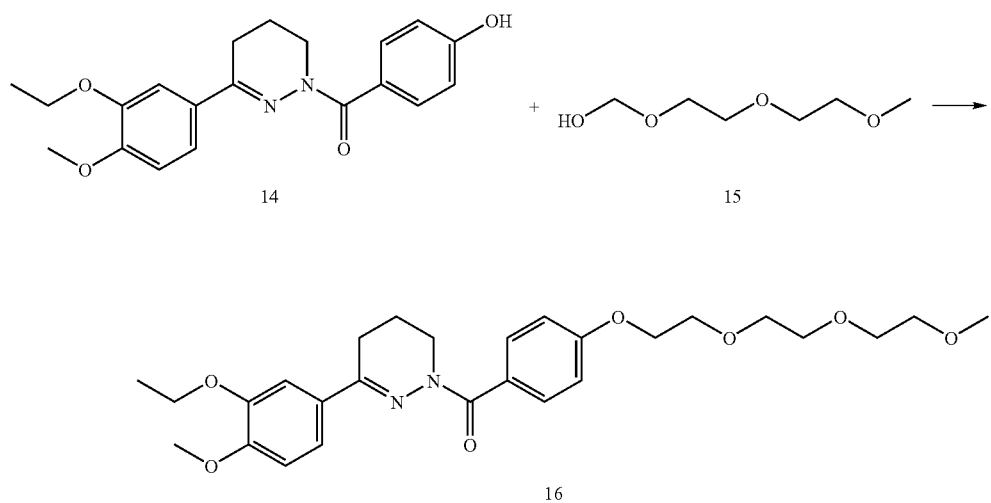

EXAMPLES 3-110

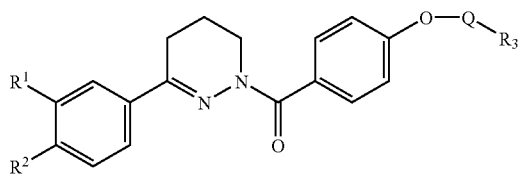

| | $R^1$ | $R^2$ | Q | $R^3$ |
|---|---|---|---|---|
| (3) | $OC_2H_5$ | $OCH_3$ | —$CH_2CH_2$— | OH |
| (4) | $OC_2H_5$ | $OCH_3$ | —$CH_2CH_2OCH_2CH_2$— | OH (m.p.: 139° C.) |
| (5) | $OC_2H_5$ | $OCH_3$ | —$CH_2CH_2OCH_2CH_2OCH_2CH_2$— | OH |
| (6) | $OC_2H_5$ | $OCH_3$ | —$CH_2CH_2$— | $OCH_3$ |
| (7) | $OC_2H_5$ | $OCH_3$ | —$CH_2CH_2OCH_2CH_2$— | $OCH_3$ |
| (8) | $OC_2H_5$ | $OCH_3$ | —$CH_2CH_2OCH_2CH_2OCH_2CH_2$— | $OCH_3$ |
| (9) | $OC_2H_5$ | $OCH_3$ | —$CH_2CH_2$— | $NH_2$ |
| (10) | $OC_2H_5$ | $OCH_3$ | —$CH_2CH_2OCH_2CH_2$— | $NH_2$ |
| (11) | $OC_2H_5$ | $OCH_3$ | —$CH_2CH_2OCH_2CH_2OCH_2CH_2$— | $NH_2$ |
| (12) | $OC_2H_5$ | $OCH_3$ | —$CH_2CH_2$— | Cl |
| (13) | $OC_2H_5$ | $OCH_3$ | —$CH_2CH_2OCH_2CH_2$— | Cl |
| (14) | $OC_2H_5$ | $OCH_3$ | —$CH_2CH_2OCH_2CH_2OCH_2CH_2$— | Cl (m.p.: 53° C.) |
| (15) | $OC_2H_5$ | $OCH_3$ | —$CH_2CH_2$— | $N(CH_3)_2$ (m.p.: 95° C.) |
| (16) | $OC_2H_5$ | $OCH_3$ | —$CH_2CH_2OCH_2CH_2$— | $N(CH_3)_2$ |
| (17) | $OC_2H_5$ | $OCH_3$ | —$CH_2CH_2OCH_2CH_2OCH_2CH_2$— | $N(CH_3)_2$ |
| (18) | $OC_2H_5$ | $OCH_3$ | —$CH_2$— | COOH |
| (19) | $OC_2H_5$ | $OCH_3$ | —$CH_2CH_2OCH_2$— | COOH |
| (20) | $OC_2H_5$ | $OCH_3$ | —$CH_2CH_2OCH_2CH_2OCH_2$— | COOH |
| (21) | $OC_2H_5$ | $OCH_3$ | —$CH_2$— | $COOC_2H_5$ |
| (22) | $OC_2H_5$ | $OCH_3$ | —$CH_2CH_2OCH_2$— | $COOC_2H_5$ |
| (23) | $OC_2H_5$ | $OCH_3$ | —$CH_2CH_2OCH_2CH_2OCH_2$— | $COOC_2H_5$ |
| (24) | $OC_2H_5$ | $OCH_3$ | —$CH_2CH_2$— | $OCO(CH_2)_6CH_3$ |
| (25) | $OC_2H_5$ | $OCH_3$ | —$CH_2CH_2OCH_2CH_2$— | $OCO(CH_2)_6CH_3$ |
| (26) | $OC_2H_5$ | $OCH_3$ | —$CH_2CH_2OCH_2CH_2OCH_2CH_2$— | $OCO(CH_2)_6CH_3$ |
| (27) | $OC_2H_5$ | $OCH_3$ | —$CH_2CH_2$— | $OCO(CH_2)_{10}CH_3$ |
| (28) | $OC_2H_5$ | $OCH_3$ | —$CH_2CH_2OCH_2CH_2$— | $OCO(CH_2)_{10}CH_3$ |
| (29) | $OC_2H_5$ | $OCH_3$ | —$CH_2CH_2OCH_2CH_2OCH_2CH_2$— | $OCO(CH_2)_{10}CH_3$ |
| (30) | $OC_2H_5$ | $OCH_3$ | —$CH_2CH_2$— | —N⟨piperazine⟩NH |
| (31) | $OC_2H_5$ | $OCH_3$ | —$CH_2CH_2OCH_2CH_2$— | —N⟨piperazine⟩NH |
| (32) | $OC_2H_5$ | $OCH_3$ | —$CH_2CH_2OCH_2CH_2OCH_2CH_2$— | —N⟨piperazine⟩NH |
| (33) | $OC_2H_5$ | $OCH_3$ | —$CH_2CH_2$— | —N⟨piperazine⟩N-C(O)O$C_2H_5$ |
| (34) | $OC_2H_5$ | $OCH_3$ | —$CH_2CH_2OCH_2CH_2$— | —N⟨piperazine⟩N-C(O)O$C_2H_5$ |
| (35) | $OC_2H_5$ | $OCH_3$ | —$CH_2CH_2OCH_2CH_2OCH_2CH_2$— | —N⟨piperazine⟩N-C(O)O$C_2H_5$ |

-continued

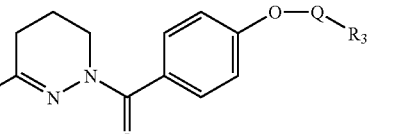

| | $R^1$ | $R^2$ | Q | $R^3$ |
|---|---|---|---|---|
| (36) | $OC_2H_5$ | $OCH_3$ | $-CH_2CH_2-$ | 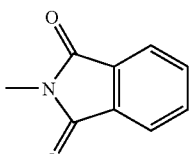 |
| (37) | $OC_2H_5$ | $OCH_3$ | $-CH_2CH_2OCH_2CH_2-$ | 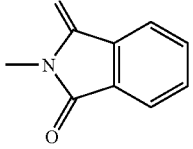 |
| (38) | $OC_2H_5$ | $OCH_3$ | $-CH_2CH_2OCH_2CH_2OCH_2CH_2-$ | 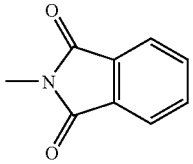 |
| (39) | $OC_2H_5$ | $OCH_3$ | $-CH_2CH_2-$ | OH |
| (40) | $OC_2H_5$ | $OCH_3$ | $-CH_2CH_2OCH_2CH_2-$ | OH |
| (41) | $OC_2H_5$ | $OCH_3$ | $-CH_2CH_2OCH_2CH_2OCH_2CH_2-$ | OH |
| (42) | $OC_2H_5$ | $OCH_3$ | $-CH_2CH_2-$ | $OCH_3$ |
| (43) | $OC_2H_5$ | $OCH_3$ | $-CH_2CH_2OCH_2CH_2-$ | $OCH_3$ |
| (44) | $OC_2H_5$ | $OCH_3$ | $-CH_2CH_2OCH_2CH_2OCH_2CH_2-$ | $OCH_3$ |
| (45) | $OC_2H_5$ | $OCH_3$ | $-CH_2CH_2-$ | $NH_2$ |
| (46) | $OC_2H_5$ | $OCH_3$ | $-CH_2CH_2OCH_2CH_2-$ | $NH_2$ |
| (47) | $OC_2H_5$ | $OCH_3$ | $-CH_2CH_2OCH_2CH_2OCH_2CH_2-$ | $NH_2$ |
| (48) | $OC_2H_5$ | $OCH_3$ | $-CH_2CH_2-$ | Cl |
| (49) | $OC_2H_5$ | $OCH_3$ | $-CH_2CH_2OCH_2CH_2-$ | Cl |
| (50) | $OC_2H_5$ | $OCH_3$ | $-CH_2CH_2OCH_2CH_2OCH_2CH_2-$ | Cl |
| (51) | $OC_2H_5$ | $OCH_3$ | $-CH_2CH_2-$ | $N(CH_3)_2$ |
| (52) | $OC_2H_5$ | $OCH_3$ | $-CH_2CH_2OCH_2CH_2-$ | $N(CH_3)_2$ |
| (53) | $OC_2H_5$ | $OCH_3$ | $-CH_2CH_2OCH_2CH_2OCH_2CH_2-$ | $N(CH_3)_2$ |
| (54) | $OC_2H_5$ | $OCH_3$ | $-CH_2-$ | COOH |
| (55) | $OC_2H_5$ | $OCH_3$ | $-CH_2CH_2OCH_2-$ | COOH |
| (56) | $OC_2H_5$ | $OCH_3$ | $-CH_2CH_2OCH_2CH_2OCH_2-$ | COOH |
| (57) | $OC_2H_5$ | $OCH_3$ | $-CH_2-$ | $COOC_2H_5$ |
| (58) | $OC_2H_5$ | $OCH_3$ | $-CH_2CH_2OCH_2-$ | $COOC_2H_5$ |
| (59) | $OC_2H_5$ | $OCH_3$ | $-CH_2CH_2OCH_2CH_2OCH_2-$ | $COOC_2H_5$ |
| (60) | $OC_2H_5$ | $OCH_3$ | $-CH_2CH_2-$ | $OCO(CH_2)_6CH_3$ |
| (61) | $OC_2H_5$ | $OCH_3$ | $-CH_2CH_2OCH_2CH_2-$ | $OCO(CH_2)_6CH_3$ |
| (62) | $OC_2H_5$ | $OCH_3$ | $-CH_2CH_2OCH_2CH_2OCH_2CH_2-$ | $OCO(CH_2)_6CH_3$ |
| (63) | $OC_2H_5$ | $OCH_3$ | $-CH_2CH_2-$ | $OCO(CH_2)_{10}CH_3$ |
| (64) | $OC_2H_5$ | $OCH_3$ | $-CH_2CH_2OCH_2CH_2-$ | $OCO(CH_2)_{10}CH_3$ |
| (65) | $OC_2H_5$ | $OCH_3$ | $-CH_2CH_2OCH_2CH_2OCH_2CH_2-$ | $OCO(CH_2)_{10}CH_3$ |
| (66) | $OC_2H_5$ | $OCH_3$ | $-CH_2CH_2-$ | 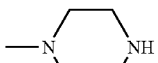 |
| (67) | $OCH_3$ | $OCH_3$ | $-CH_2CH_2OCH_2CH_2-$ | 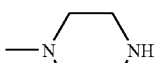 |
| (68) | $OCH_3$ | $OCH_3$ | $-CH_2CH_2OCH_2CH_2OCH_2CH_2-$ | 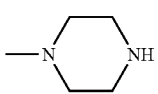 |

-continued

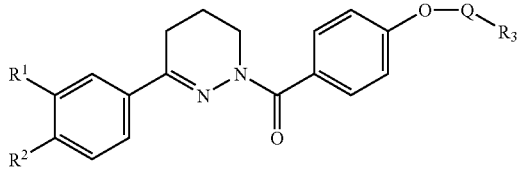

| R¹ | R² | Q | R³ |
|---|---|---|---|
| (69) OCH₃ | OCH₃ | —CH₂CH₂— |  |
| (70) OCH₃ | OCH₃ | —CH₂CH₂OCH₂CH₂— | 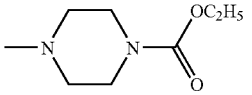 |
| (71) OCH₃ | OCH₃ | —CH₂CH₂OCH₂CH₂OCH₂CH₂— | 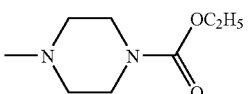 |
| (72) OCH₃ | OCH₃ | —CH₂CH₂— | 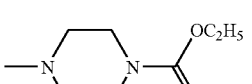 |
| (73) OCH₃ | OCH₃ | —CH₂CH₂OCH₂CH₂— | 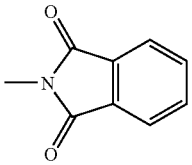 |
| (74) OCH₃ | OCH₃ | —CH₂CH₂OCH₂CH₂OCH₂CH₂— | 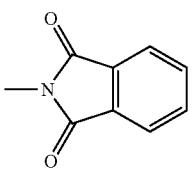 |
| (75) OC₂H₅ | OC₂H₅ | —CH₂CH₂— | OH |
| (76) OC₂H₅ | OC₂H₅ | —CH₂CH₂OCH₂CH₂— | OH |
| (77) OC₂H₅ | OC₂H₅ | —CH₂CH₂OCH₂CH₂OCH₂CH₂— | OH |
| (78) OC₂H₅ | OC₂H₅ | —CH₂CH₂— | OCH₃ |
| (79) OC₂H₅ | OC₂H₅ | —CH₂CH₂OCH₂CH₂— | OCH₃ |
| (80) OC₂H₅ | OC₂H₅ | —CH₂CH₂OCH₂CH₂OCH₂CH₂— | OCH₃ |
| (81) OC₂H₅ | OC₂H₅ | —CH₂CH₂— | NH₂ |
| (82) OC₂H₅ | OC₂H₅ | —CH₂CH₂OCH₂CH₂— | NH₂ |
| (83) OC₂H₅ | OC₂H₅ | —CH₂CH₂OCH₂CH₂OCH₂CH₂— | NH₂ |
| (84) OC₂H₅ | OC₂H₅ | —CH₂CH₂— | Cl |
| (85) OC₂H₅ | OC₂H₅ | —CH₂CH₂OCH₂CH₂— | Cl |
| (86) OC₂H₅ | OC₂H₅ | —CH₂CH₂OCH₂CH₂OCH₂CH₂— | Cl |
| (87) OC₂H₅ | OC₂H₅ | —CH₂CH₂— | N(CH₃)₂ |
| (88) OC₂H₅ | OC₂H₅ | —CH₂CH₂OCH₂CH₂— | N(CH₃)₂ |
| (89) OC₂H₅ | OC₂H₅ | —CH₂CH₂OCH₂CH₂OCH₂CH₂— | N(CH₃)₂ |
| (90) OC₂H₅ | OC₂H₅ | —CH₂— | COOH |
| (91) OC₂H₅ | OC₂H₅ | —CH₂CH₂OCH₂— | COOH |
| (92) OC₂H₅ | OC₂H₅ | —CH₂CH₂OCH₂CH₂OCH₂— | COOH |
| (93) OC₂H₅ | OC₂H₅ | —CH₂— | COOC₂H₅ |
| (94) OC₂H₅ | OC₂H₅ | —CH₂CH₂OCH₂— | COOC₂H₅ |
| (95) OC₂H₅ | OC₂H₅ | —CH₂CH₂OCH₂CH₂OCH₂— | COOC₂H₅ |
| (96) OC₂H₅ | OC₂H₅ | —CH₂CH₂— | OCO(CH₂)₆CH₃ |
| (97) OC₂H₅ | OC₂H₅ | —CH₂CH₂OCH₂CH₂— | OCO(CH₂)₆CH₃ |
| (98) OC₂H₅ | OC₂H₅ | —CH₂CH₂OCH₂CH₂OCH₂CH₂— | OCO(CH₂)₆CH₃ |
| (99) OC₂H₅ | OC₂H₅ | —CH₂CH₂— | OCO(CH₂)₁₀CH₃ |
| (100) OC₂H₅ | OC₂H₅ | —CH₂CH₂OCH₂CH₂— | OCO(CH₂)₁₀CH₃ |
| (101) OC₂H₅ | OC₂H₅ | —CH₂CH₂OCH₂CH₂OCH₂CH₂— | OCO(CH₂)₁₀CH₃ |

-continued
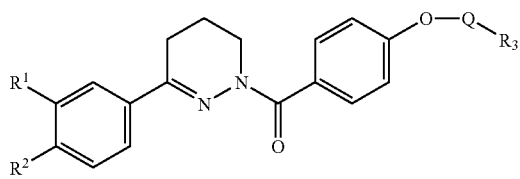
| | R¹ | R² | Q | R³ |
|---|---|---|---|---|
| (102) | OC₂H₅ | OC₂H₅ | —CH₂CH₂— | 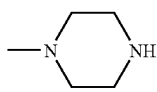 |
| (103) | OC₂H₅ | OC₂H₅ | —CH₂CH₂OCH₂CH₂— | 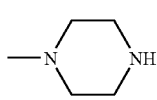 |
| (104) | OC₂H₅ | OC₂H₅ | —CH₂CH₂OCH₂CH₂OCH₂CH₂— | 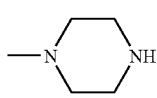 |
| (105) | OC₂H₅ | OC₂H₅ | —CH₂CH₂— | 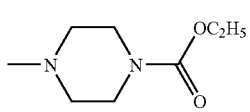 |
| (106) | OC₂H₅ | OC₂H₅ | —CH₂CH₂OCH₂CH₂— | 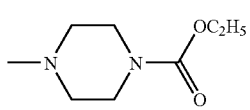 |
| (107) | OC₂H₅ | OC₂H₅ | —CH₂CH₂OCH₂CH₂OCH₂CH₂— | 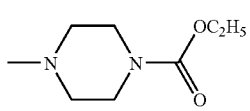 |
| (108) | OC₂H₅ | OC₂H₅ | —CH₂CH₂— | 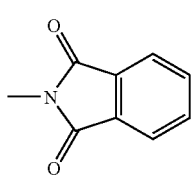 |
| (109) | OC₂H₅ | OC₂H₅ | —CH₂CH₂OCH₂CH₂— | 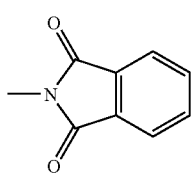 |
| (110) | OC₂H₅ | OC₂H₅ | —CH₂CH₂OCH₂CH₂OCH₂CH₂— | 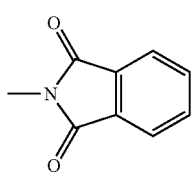 |

EXAMPLES 111-146

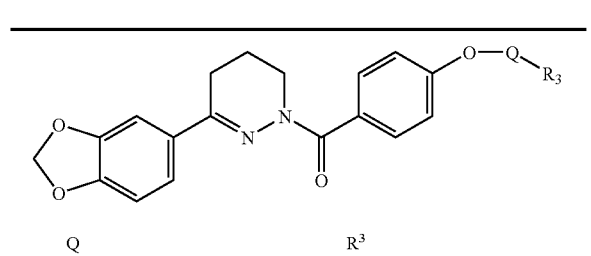

| | Q | R³ |
|---|---|---|
| (111) | —CH₂CH₂— | OH |
| (112) | —CH₂CH₂OCH₂CH₂— | OH |
| (113) | —CH₂CH₂OCH₂CH₂OCH₂CH₂— | OH |
| (114) | —CH₂CH₂— | OCH₃ |
| (115) | —CH₂CH₂OCH₂CH₂— | OCH₃ |
| (116) | —CH₂CH₂OCH₂CH₂OCH₂CH₂— | OCH₃ |
| (117) | —CH₂CH₂— | NH₂ |
| (118) | —CH₂CH₂OCH₂CH₂— | NH₂ |
| (119) | —CH₂CH₂OCH₂CH₂OCH₂CH₂— | NH₂ |
| (120) | —CH₂CH₂— | Cl |
| (121) | —CH₂CH₂OCH₂CH₂— | Cl |
| (122) | —CH₂CH₂OCH₂CH₂OCH₂CH₂— | Cl |
| (123) | —CH₂CH₂— | N(CH₃)₂ |
| (124) | —CH₂CH₂OCH₂CH₂— | N(CH₃)₂ |
| (125) | —CH₂CH₂OCH₂CH₂OCH₂CH₂— | N(CH₃)₂ |
| (126) | —CH₂— | COOH |
| (127) | —CH₂CH₂OCH₂— | COOH |
| (128) | —CH₂CH₂OCH₂CH₂OCH₂— | COOH |
| (129) | —CH₂— | COOC₂H₅ |
| (130) | —CH₂CH₂OCH₂— | COOC₂H₅ |
| (131) | —CH₂CH₂OCH₂CH₂OCH₂— | COOC₂H₅ |
| (132) | —CH₂CH₂— | OCO(CH₂)₆CH₃ |
| (133) | —CH₂CH₂OCH₂CH₂— | OCO(CH₂)₆CH₃ |
| (134) | —CH₂CH₂OCH₂CH₂OCH₂CH₂— | OCO(CH₂)₆CH₃ |
| (135) | —CH₂CH₂— | OCO(CH₂)₁₀CH₃ |
| (136) | —CH₂CH₂OCH₂CH₂— | OCO(CH₂)₁₀CH₃ |
| (137) | —CH₂CH₂OCH₂CH₂OCH₂CH₂— | OCO(CH₂)₁₀CH₃ |

(138) —CH₂CH₂—

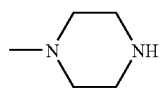

(139) —CH₂CH₂OCH₂CH₂—

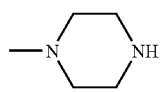

(140) —CH₂CH₂OCH₂CH₂OCH₂CH₂—

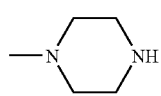

(141) —CH₂CH₂—

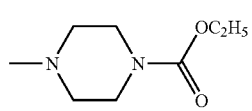

-continued

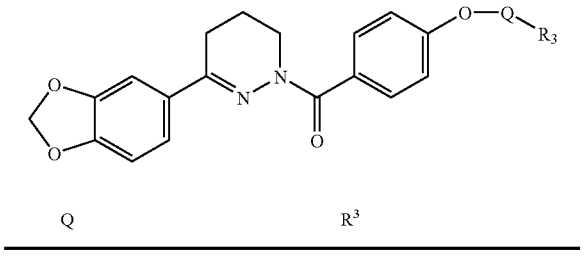

| | Q | R³ |
|---|---|---|

(142) —CH₂CH₂OCH₂CH₂—

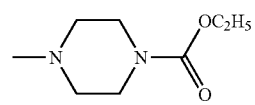

(143) —CH₂CH₂OCH₂CH₂OCH₂CH₂—

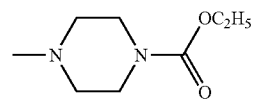

(144) —CH₂CH₂—

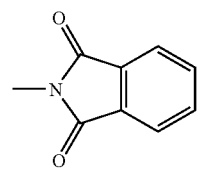

(145) —CH₂CH₂OCH₂CH₂—

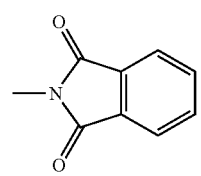

(146) —CH₂CH₂OCH₂CH₂OCH₂CH₂—

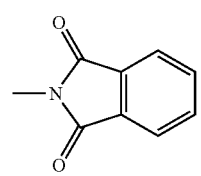

EXAMPLES 147-254

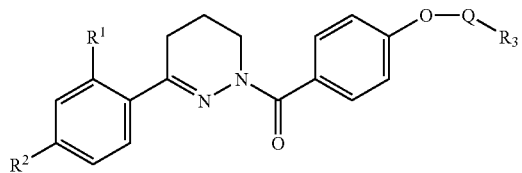

| | R¹ | R² | Q | R³ |
|---|---|---|---|---|
| (147) | OC₂H₅ | OCH₃ | —CH₂CH₂— | OH |
| (148) | OC₂H₅ | OCH₃ | —CH₂CH₂OCH₂CH₂— | OH |
| (149) | OC₂H₅ | OCH₃ | —CH₂CH₂OCH₂CH₂OCH₂CH₂— | OH |
| (150) | OC₂H₅ | OCH₃ | —CH₂CH₂— | OCH₃ |
| (151) | OC₂H₅ | OCH₃ | —CH₂CH₂OCH₂CH₂— | OCH₃ |
| (152) | OC₂H₅ | OCH₃ | —CH₂CH₂OCH₂CH₂OCH₂CH₂— | OCH₃ |
| (153) | OC₂H₅ | OCH₃ | —CH₂CH₂— | NH₂ |
| (154) | OC₂H₅ | OCH₃ | —CH₂CH₂OCH₂CH₂— | NH₂ |
| (155) | OC₂H₅ | OCH₃ | —CH₂CH₂OCH₂CH₂OCH₂CH₂— | NH₂ |
| (156) | OC₂H₅ | OCH₃ | —CH₂CH₂— | Cl |
| (157) | OC₂H₅ | OCH₃ | —CH₂CH₂OCH₂CH₂— | Cl |
| (158) | OC₂H₅ | OCH₃ | —CH₂CH₂OCH₂CH₂OCH₂CH₂— | Cl |
| (159) | OC₂H₅ | OCH₃ | —CH₂CH₂— | N(CH₃)₂ |
| (160) | OC₂H₅ | OCH₃ | —CH₂CH₂OCH₂CH₂— | N(CH₃)₂ |
| (161) | OC₂H₅ | OCH₃ | —CH₂CH₂OCH₂CH₂OCH₂CH₂— | N(CH₃)₂ |
| (162) | OC₂H₅ | OCH₃ | —CH₂CH₂— | COOH |
| (163) | OC₂H₅ | OCH₃ | —CH₂CH₂OCH₂CH₂— | COOH |
| (164) | OC₂H₅ | OCH₃ | —CH₂CH₂OCH₂CH₂OCH₂CH₂— | COOH |
| (165) | OC₂H₅ | OCH₃ | —CH₂— | COOC₂H₅ |
| (166) | OC₂H₅ | OCH₃ | —CH₂CH₂OCH₂— | COOC₂H₅ |
| (167) | OC₂H₅ | OCH₃ | —CH₂CH₂OCH₂CH₂OCH₂— | COOC₂H₅ |
| (168) | OC₂H₅ | OCH₃ | —CH₂— | OCO(CH₂)₆CH₃ |
| (169) | OC₂H₅ | OCH₃ | —CH₂CH₂OCH₂— | OCO(CH₂)₆CH₃ |
| (170) | OC₂H₅ | OCH₃ | —CH₂CH₂OCH₂CH₂OCH₂— | OCO(CH₂)₆CH₃ |
| (171) | OC₂H₅ | OCH₃ | —CH₂CH₂— | OCO(CH₂)₁₀CH₃ |
| (172) | OC₂H₅ | OCH₃ | —CH₂CH₂OCH₂CH₂— | OCO(CH₂)₁₀CH₃ |
| (173) | OC₂H₅ | OCH₃ | —CH₂CH₂OCH₂CH₂OCH₂CH₂— | OCO(CH₂)₁₀CH₃ |
| (174) | OC₂H₅ | OCH₃ | —CH₂CH₂— | —N⟨piperazine⟩NH |
| (175) | OC₂H₅ | OCH₃ | —CH₂CH₂OCH₂CH₂— | —N⟨piperazine⟩NH |
| (176) | OC₂H₅ | OCH₃ | —CH₂CH₂OCH₂CH₂OCH₂CH₂— | —N⟨piperazine⟩NH |
| (177) | OC₂H₅ | OCH₃ | —CH₂CH₂— | —N⟨piperazine⟩N-C(O)OC₂H₅ |
| (178) | OC₂H₅ | OCH₃ | —CH₂CH₂OCH₂CH₂— | —N⟨piperazine⟩N-C(O)OC₂H₅ |
| (179) | OC₂H₅ | OCH₃ | —CH₂CH₂OCH₂CH₂OCH₂CH₂— | —N⟨piperazine⟩N-C(O)OC₂H₅ |

-continued

[Structure: 3-(2-R¹,4-R²-phenyl)-4,5-dihydropyridazin-1-yl connected via C(=O) to 4-(O-Q-R³)phenyl]

| | R¹ | R² | Q | R³ |
|---|---|---|---|---|
| (180) | OC₂H₅ | OCH₃ | —CH₂CH₂— | N-phthalimidyl |
| (181) | OC₂H₅ | OCH₃ | —CH₂CH₂OCH₂CH₂— | N-phthalimidyl |
| (182) | OC₂H₅ | OCH₃ | —CH₂CH₂OCH₂CH₂OCH₂CH₂— | N-phthalimidyl |
| (183) | OCH₃ | OCH₃ | —CH₂CH₂— | OH |
| (184) | OCH₃ | OCH₃ | —CH₂CH₂OCH₂CH₂— | OH |
| (185) | OCH₃ | OCH₃ | —CH₂CH₂OCH₂CH₂OCH₂CH₂— | OH |
| (186) | OCH₃ | OCH₃ | —CH₂CH₂— | OCH₃ |
| (187) | OCH₃ | OCH₃ | —CH₂CH₂OCH₂CH₂— | OCH₃ |
| (188) | OCH₃ | OCH₃ | —CH₂CH₂OCH₂CH₂OCH₂CH₂— | OCH₃ |
| (189) | OCH₃ | OCH₃ | —CH₂CH₂— | NH₂ |
| (190) | OCH₃ | OCH₃ | —CH₂CH₂OCH₂CH₂— | NH₂ |
| (191) | OCH₃ | OCH₃ | —CH₂CH₂OCH₂CH₂OCH₂CH₂— | NH₂ |
| (192) | OCH₃ | OCH₃ | —CH₂CH₂— | Cl |
| (193) | OCH₃ | OCH₃ | —CH₂CH₂OCH₂CH₂— | Cl |
| (194) | OCH₃ | OCH₃ | —CH₂CH₂OCH₂CH₂OCH₂CH₂— | Cl |
| (195) | OCH₃ | OCH₃ | —CH₂CH₂— | N(CH₃)₂ |
| (196) | OCH₃ | OCH₃ | —CH₂CH₂OCH₂CH₂— | N(CH₃)₂ |
| (197) | OCH₃ | OCH₃ | —CH₂CH₂OCH₂CH₂OCH₂CH₂— | N(CH₃)₂ |
| (198) | OCH₃ | OCH₃ | —CH₂— | COOH |
| (199) | OCH₃ | OCH₃ | —CH₂CH₂OCH₂— | COOH |
| (200) | OCH₃ | OCH₃ | —CH₂CH₂OCH₂CH₂OCH₂— | COOH |
| (201) | OCH₃ | OCH₃ | —CH₂— | COOC₂H₅ |
| (202) | OCH₃ | OCH₃ | —CH₂CH₂OCH₂— | COOC₂H₅ |
| (203) | OCH₃ | OCH₃ | —CH₂CH₂OCH₂CH₂OCH₂— | COOC₂H₅ |
| (204) | OCH₃ | OCH₃ | —CH₂CH₂— | OCO(CH₂)₆CH₃ |
| (205) | OCH₃ | OCH₃ | —CH₂CH₂OCH₂CH₂— | OCO(CH₂)₆CH₃ |
| (206) | OCH₃ | OCH₃ | —CH₂CH₂OCH₂CH₂OCH₂CH₂— | OCO(CH₂)₆CH₃ |
| (207) | OCH₃ | OCH₃ | —CH₂CH₂— | OCO(CH₂)₁₀CH₃ |
| (208) | OCH₃ | OCH₃ | —CH₂CH₂OCH₂CH₂— | OCO(CH₂)₁₀CH₃ |
| (209) | OCH₃ | OCH₃ | —CH₂CH₂OCH₂CH₂OCH₂CH₂— | OCO(CH₂)₁₀CH₃ |
| (210) | OCH₃ | OCH₃ | —CH₂CH₂— | piperazin-1-yl (NH) |
| (211) | OCH₃ | OCH₃ | —CH₂CH₂OCH₂CH₂— | piperazin-1-yl (NH) |

-continued

[Structure: 2-(R¹)-4-(R²)-phenyl substituted tetrahydropyridazine linked via N-C(=O) to 4-(O-Q-R³)phenyl]

| | R¹ | R² | Q | R³ |
|---|---|---|---|---|
| (212) | OCH₃ | OCH₃ | —CH₂CH₂OCH₂CH₂OCH₂CH₂— | piperazine-NH |
| (213) | OCH₃ | OCH₃ | —CH₂CH₂— | 4-(ethoxycarbonyl)piperazin-1-yl |
| (214) | OCH₃ | OCH₃ | —CH₂CH₂OCH₂CH₂— | 4-(ethoxycarbonyl)piperazin-1-yl |
| (215) | OCH₃ | OCH₃ | —CH₂CH₂OCH₂CH₂OCH₂CH₂— | 4-(ethoxycarbonyl)piperazin-1-yl |
| (216) | OCH₃ | OCH₃ | —CH₂CH₂— | phthalimido |
| (217) | OCH₃ | OCH₃ | —CH₂CH₂OCH₂CH₂— | phthalimido |
| (218) | OCH₃ | OCH₃ | —CH₂CH₂OCH₂CH₂OCH₂CH₂— | phthalimido |
| (219) | OC₂H₅ | OC₂H₅ | —CH₂CH₂— | OH |
| (220) | OC₂H₅ | OC₂H₅ | —CH₂CH₂OCH₂CH₂— | OH |
| (221) | OC₂H₅ | OC₂H₅ | —CH₂CH₂OCH₂CH₂OCH₂CH₂— | OH |
| (222) | OC₂H₅ | OC₂H₅ | —CH₂CH₂— | OCH₃ |
| (223) | OC₂H₅ | OC₂H₅ | —CH₂CH₂OCH₂CH₂— | OCH₃ |
| (224) | OC₂H₅ | OC₂H₅ | —CH₂CH₂OCH₂CH₂OCH₂CH₂— | OCH₃ |
| (225) | OC₂H₅ | OC₂H₅ | —CH₂CH₂— | NH₂ |
| (226) | OC₂H₅ | OC₂H₅ | —CH₂CH₂OCH₂CH₂— | NH₂ |
| (227) | OC₂H₅ | OC₂H₅ | —CH₂CH₂OCH₂CH₂OCH₂CH₂— | NH₂ |
| (228) | OC₂H₅ | OC₂H₅ | —CH₂CH₂— | Cl |
| (229) | OC₂H₅ | OC₂H₅ | —CH₂CH₂OCH₂CH₂— | Cl |
| (230) | OC₂H₅ | OC₂H₅ | —CH₂CH₂OCH₂CH₂OCH₂CH₂— | Cl |
| (231) | OC₂H₅ | OC₂H₅ | —CH₂CH₂— | N(CH₃)₂ |
| (232) | OC₂H₅ | OC₂H₅ | —CH₂CH₂OCH₂CH₂— | N(CH₃)₂ |
| (233) | OC₂H₅ | OC₂H₅ | —CH₂CH₂OCH₂CH₂OCH₂CH₂— | N(CH₃)₂ |
| (234) | OC₂H₅ | OC₂H₅ | —CH₂— | COOH |
| (235) | OC₂H₅ | OC₂H₅ | —CH₂CH₂OCH₂— | COOH |
| (236) | OC₂H₅ | OC₂H₅ | —CH₂CH₂OCH₂CH₂OCH₂— | COOH |
| (237) | OC₂H₅ | OC₂H₅ | —CH₂— | COOC₂H₅ |
| (238) | OC₂H₅ | OC₂H₅ | —CH₂CH₂OCH₂— | COOC₂H₅ |

-continued

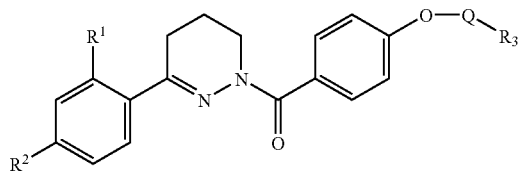

| | $R^1$ | $R^2$ | Q | $R^3$ |
|---|---|---|---|---|
| (239) | $OC_2H_5$ | $OC_2H_5$ | —$CH_2CH_2OCH_2CH_2OCH_2$— | $COOC_2H_5$ |
| (240) | $OC_2H_5$ | $OC_2H_5$ | —$CH_2CH_2$— | $OCO(CH_2)_6CH_3$ |
| (241) | $OC_2H_5$ | $OC_2H_5$ | —$CH_2CH_2OCH_2CH_2$— | $OCO(CH_2)_6CH_3$ |
| (242) | $OC_2H_5$ | $OC_2H_5$ | —$CH_2CH_2OCH_2CH_2OCH_2$— | $OCO(CH_2)_6CH_3$ |
| (243) | $OC_2H_5$ | $OC_2H_5$ | —$CH_2CH_2$— | $OCO(CH_2)_{10}CH_3$ |
| (244) | $OC_2H_5$ | $OC_2H_5$ | —$CH_2CH_2OCH_2CH_2$— | $OCO(CH_2)_{10}CH_3$ |
| (245) | $OC_2H_5$ | $OC_2H_5$ | —$CH_2CH_2OCH_2CH_2OCH_2$— | $OCO(CH_2)_{10}CH_3$ |
| (246) | $OC_2H_5$ | $OC_2H_5$ | —$CH_2CH_2$— | piperazine |
| (247) | $OC_2H_5$ | $OC_2H_5$ | —$CH_2CH_2OCH_2CH_2$— | piperazine |
| (248) | $OC_2H_5$ | $OC_2H_5$ | —$CH_2CH_2OCH_2CH_2OCH_2$— | piperazine |
| (249) | $OC_2H_5$ | $OC_2H_5$ | —$CH_2CH_2$— | N-ethoxycarbonylpiperazine |
| (250) | $OC_2H_5$ | $OC_2H_5$ | —$CH_2CH_2OCH_2CH_2$— | N-ethoxycarbonylpiperazine |
| (251) | $OC_2H_5$ | $OC_2H_5$ | —$CH_2CH_2OCH_2CH_2OCH_2$— | N-ethoxycarbonylpiperazine |
| (252) | $OC_2H_5$ | $OC_2H_5$ | —$CH_2CH_2$— | phthalimido |
| (253) | $OC_2H_5$ | $OC_2H_5$ | —$CH_2CH_2OCH_2CH_2$— | phthalimido |
| (254) | $OC_2H_5$ | $OC_2H_5$ | —$CH_2CH_2OCH_2CH_2OCH_2$— | phthalimido |

EXAMPLES 255-362

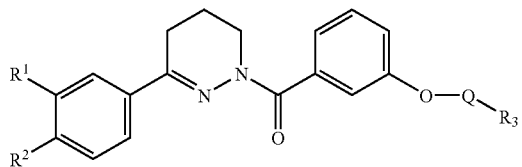

| R¹ | R² | Q | R³ |
|---|---|---|---|
| (255) OC$_2$H$_5$ | OCH$_3$ | —CH$_2$CH$_2$— | OH |
| (256) OC$_2$H$_5$ | OCH$_3$ | —CH$_2$CH$_2$OCH$_2$CH$_2$— | OH (m.p.: 139° C.) |
| (257) OC$_2$H$_5$ | OCH$_3$ | —CH$_2$CH$_2$OCH$_2$CH$_2$OCH$_2$CH$_2$— | OH |
| (258) OC$_2$H$_5$ | OCH$_3$ | —CH$_2$CH$_2$— | OCH$_3$ |
| (259) OC$_2$H$_5$ | OCH$_3$ | —CH$_2$CH$_2$OCH$_2$CH$_2$— | OCH$_3$ |
| (260) OC$_2$H$_5$ | OCH$_3$ | —CH$_2$CH$_2$OCH$_2$CH$_2$OCH$_2$CH$_2$— | OCH$_3$ |
| (261) OC$_2$H$_5$ | OCH$_3$ | —CH$_2$CH$_2$— | NH$_2$ |
| (262) OC$_2$H$_5$ | OCH$_3$ | —CH$_2$CH$_2$OCH$_2$CH$_2$— | NH$_2$ |
| (263) OC$_2$H$_5$ | OCH$_3$ | —CH$_2$CH$_2$OCH$_2$CH$_2$OCH$_2$CH$_2$— | NH$_2$ |
| (264) OC$_2$H$_5$ | OCH$_3$ | —CH$_2$CH$_2$— | Cl |
| (265) OC$_2$H$_5$ | OCH$_3$ | —CH$_2$CH$_2$OCH$_2$CH$_2$— | Cl |
| (266) OC$_2$H$_5$ | OCH$_3$ | —CH$_2$CH$_2$OCH$_2$CH$_2$OCH$_2$CH$_2$— | Cl (m.p.: 53° C.) |
| (267) OC$_2$H$_5$ | OCH$_3$ | —CH$_2$CH$_2$— | N(CH$_3$)$_2$ (m.p.: 95° C.) |
| (268) OC$_2$H$_5$ | OCH$_3$ | —CH$_2$CH$_2$OCH$_2$CH$_2$— | N(CH$_3$)$_2$ |
| (269) OC$_2$H$_5$ | OCH$_3$ | —CH$_2$CH$_2$OCH$_2$CH$_2$OCH$_2$CH$_2$— | N(CH$_3$)$_2$ |
| (270) OC$_2$H$_5$ | OCH$_3$ | —CH$_2$— | COOH |
| (271) OC$_2$H$_5$ | OCH$_3$ | —CH$_2$CH$_2$OCH$_2$— | COOH |
| (272) OC$_2$H$_5$ | OCH$_3$ | —CH$_2$CH$_2$OCH$_2$CH$_2$OCH$_2$— | COOH |
| (273) OC$_2$H$_5$ | OCH$_3$ | —CH$_2$— | COOC$_2$H$_5$ |
| (274) OC$_2$H$_5$ | OCH$_3$ | —CH$_2$CH$_2$OCH$_2$— | COOC$_2$H$_5$ |
| (275) OC$_2$H$_5$ | OCH$_3$ | —CH$_2$CH$_2$OCH$_2$CH$_2$OCH$_2$— | COOC$_2$H$_5$ |
| (276) OC$_2$H$_5$ | OCH$_3$ | —CH$_2$CH$_2$— | OCO(CH$_2$)$_6$CH$_3$ |
| (277) OC$_2$H$_5$ | OCH$_3$ | —CH$_2$CH$_2$OCH$_2$CH$_2$— | OCO(CH$_2$)$_6$CH$_3$ |
| (278) OC$_2$H$_5$ | OCH$_3$ | —CH$_2$CH$_2$OCH$_2$CH$_2$OCH$_2$CH$_2$— | OCO(CH$_2$)$_6$CH$_3$ |
| (279) OC$_2$H$_5$ | OCH$_3$ | —CH$_2$CH$_2$— | OCO(CH$_2$)$_{10}$CH$_3$ |
| (280) OC$_2$H$_5$ | OCH$_3$ | —CH$_2$CH$_2$OCH$_2$CH$_2$— | OCO(CH$_2$)$_{10}$CH$_3$ |
| (281) OC$_2$H$_5$ | OCH$_3$ | —CH$_2$CH$_2$OCH$_2$CH$_2$OCH$_2$CH$_2$— | OCO(CH$_2$)$_{10}$CH$_3$ |
| (282) OC$_2$H$_5$ | OCH$_3$ | —CH$_2$CH$_2$— | —N(piperazine)NH |
| (283) OC$_2$H$_5$ | OCH$_3$ | —CH$_2$CH$_2$OCH$_2$CH$_2$— | —N(piperazine)NH |
| (284) OC$_2$H$_5$ | OCH$_3$ | —CH$_2$CH$_2$OCH$_2$CH$_2$OCH$_2$CH$_2$— | —N(piperazine)NH |
| (285) OC$_2$H$_5$ | OCH$_3$ | —CH$_2$CH$_2$— | —N(piperazine)N-C(O)OC$_2$H$_5$ |
| (286) OC$_2$H$_5$ | OCH$_3$ | —CH$_2$CH$_2$OCH$_2$CH$_2$— | —N(piperazine)N-C(O)OC$_2$H$_5$ |
| (287) OC$_2$H$_5$ | OCH$_3$ | —CH$_2$CH$_2$OCH$_2$CH$_2$OCH$_2$CH$_2$— | —N(piperazine)N-C(O)OC$_2$H$_5$ |

-continued

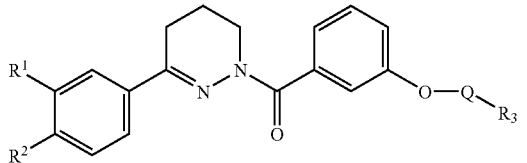

| | R¹ | R² | Q | R³ |
|---|---|---|---|---|
| (288) | OC₂H₅ | OCH₃ | —CH₂CH₂— | 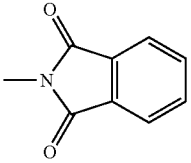 |
| (289) | OC₂H₅ | OCH₃ | —CH₂CH₂OCH₂CH₂— | 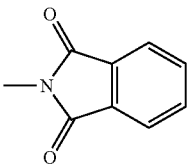 |
| (290) | OC₂H₅ | OCH₃ | —CH₂CH₂OCH₂CH₂OCH₂CH₂— | 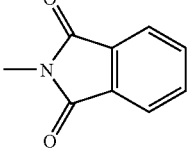 |
| (291) | OCH₃ | OCH₃ | —CH₂CH₂— | OH |
| (292) | OCH₃ | OCH₃ | —CH₂CH₂OCH₂CH₂— | OH |
| (293) | OCH₃ | OCH₃ | —CH₂CH₂OCH₂CH₂OCH₂CH₂— | OH |
| (294) | OCH₃ | OCH₃ | —CH₂CH₂— | OCH₃ |
| (295) | OCH₃ | OCH₃ | —CH₂CH₂OCH₂CH₂— | OCH₃ |
| (296) | OCH₃ | OCH₃ | —CH₂CH₂OCH₂CH₂OCH₂CH₂— | OCH₃ |
| (297) | OCH₃ | OCH₃ | —CH₂CH₂— | NH₂ |
| (298) | OCH₃ | OCH₃ | —CH₂CH₂OCH₂CH₂— | NH₂ |
| (299) | OCH₃ | OCH₃ | —CH₂CH₂OCH₂CH₂OCH₂CH₂— | NH₂ |
| (300) | OCH₃ | OCH₃ | —CH₂CH₂— | Cl |
| (301) | OCH₃ | OCH₃ | —CH₂CH₂OCH₂CH₂— | Cl |
| (302) | OCH₃ | OCH₃ | —CH₂CH₂OCH₂CH₂OCH₂CH₂— | Cl |
| (303) | OCH₃ | OCH₃ | —CH₂CH₂— | N(CH₃)₂ |
| (304) | OCH₃ | OCH₃ | —CH₂CH₂OCH₂CH₂— | N(CH₃)₂ |
| (305) | OCH₃ | OCH₃ | —CH₂CH₂OCH₂CH₂OCH₂CH₂— | N(CH₃)₂ |
| (306) | OCH₃ | OCH₃ | —CH₂— | COOH |
| (307) | OCH₃ | OCH₃ | —CH₂CH₂OCH₂— | COOH |
| (308) | OCH₃ | OCH₃ | —CH₂CH₂OCH₂CH₂OCH₂— | COOH |
| (309) | OCH₃ | OCH₃ | —CH₂— | COOC₂H₅ |
| (310) | OCH₃ | OCH₃ | —CH₂CH₂OCH₂— | COOC₂H₅ |
| (311) | OCH₃ | OCH₃ | —CH₂CH₂OCH₂CH₂OCH₂— | COOC₂H₅ |
| (312) | OCH₃ | OCH₃ | —CH₂CH₂— | OCO(CH₂)₆CH₃ |
| (313) | OCH₃ | OCH₃ | —CH₂CH₂OCH₂CH₂— | OCO(CH₂)₆CH₃ |
| (314) | OCH₃ | OCH₃ | —CH₂CH₂OCH₂CH₂OCH₂CH₂— | OCO(CH₂)₆CH₃ |
| (315) | OCH₃ | OCH₃ | —CH₂CH₂— | OCO(CH₂)₁₀CH₃ |
| (316) | OCH₃ | OCH₃ | —CH₂CH₂OCH₂CH₂— | OCO(CH₂)₁₀CH₃ |
| (317) | OCH₃ | OCH₃ | —CH₂CH₂OCH₂CH₂OCH₂CH₂— | OCO(CH₂)₁₀CH₃ |
| (318) | OCH₃ | OCH₃ | —CH₂CH₂— |  |
| (319) | OCH₃ | OCH₃ | —CH₂CH₂OCH₂CH₂— | 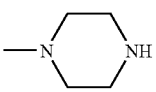 |

-continued

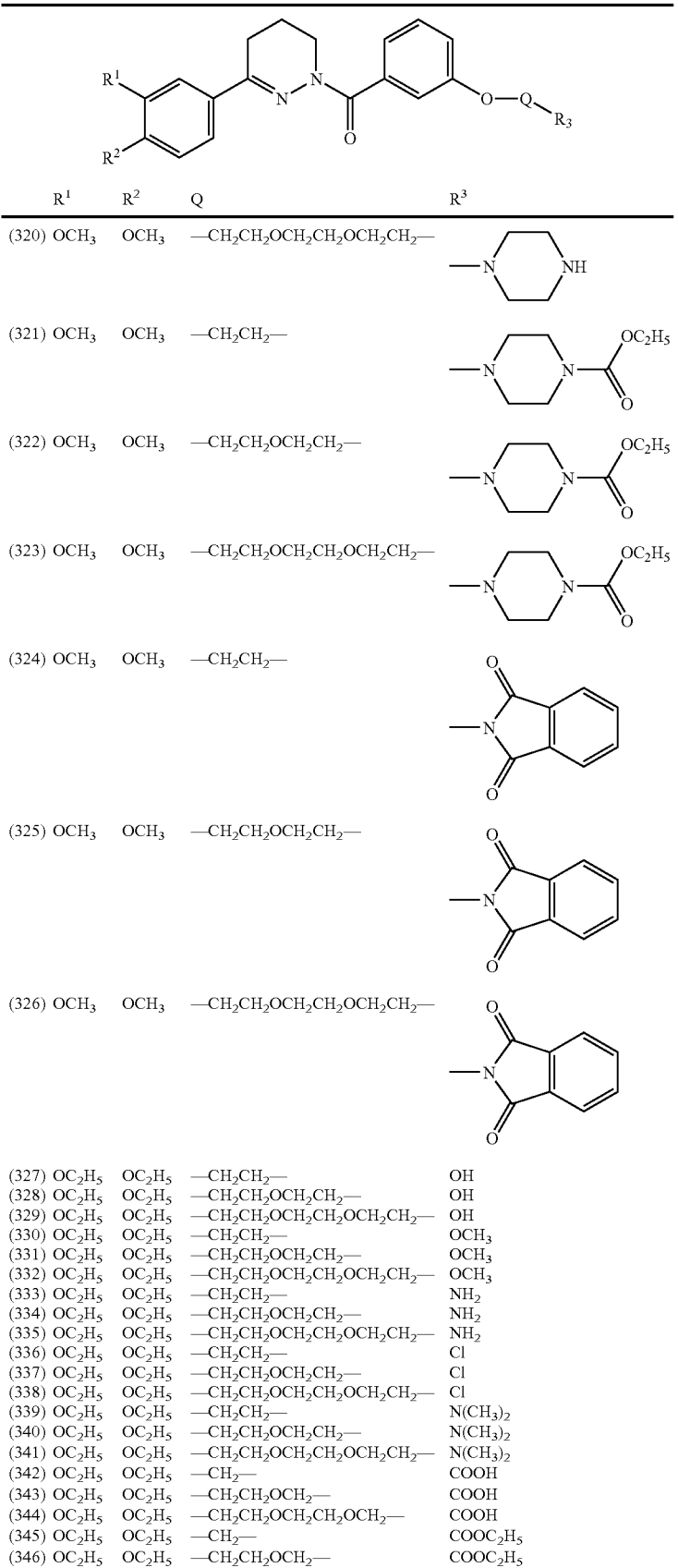

| | R¹ | R² | Q | R³ |
|---|---|---|---|---|
| (320) | OCH₃ | OCH₃ | —CH₂CH₂OCH₂CH₂OCH₂CH₂— | piperazine-NH |
| (321) | OCH₃ | OCH₃ | —CH₂CH₂— | piperazine-C(O)OC₂H₅ |
| (322) | OCH₃ | OCH₃ | —CH₂CH₂OCH₂CH₂— | piperazine-C(O)OC₂H₅ |
| (323) | OCH₃ | OCH₃ | —CH₂CH₂OCH₂CH₂OCH₂CH₂— | piperazine-C(O)OC₂H₅ |
| (324) | OCH₃ | OCH₃ | —CH₂CH₂— | phthalimide |
| (325) | OCH₃ | OCH₃ | —CH₂CH₂OCH₂CH₂— | phthalimide |
| (326) | OCH₃ | OCH₃ | —CH₂CH₂OCH₂CH₂OCH₂CH₂— | phthalimide |
| (327) | OC₂H₅ | OC₂H₅ | —CH₂CH₂— | OH |
| (328) | OC₂H₅ | OC₂H₅ | —CH₂CH₂OCH₂CH₂— | OH |
| (329) | OC₂H₅ | OC₂H₅ | —CH₂CH₂OCH₂CH₂OCH₂CH₂— | OH |
| (330) | OC₂H₅ | OC₂H₅ | —CH₂CH₂— | OCH₃ |
| (331) | OC₂H₅ | OC₂H₅ | —CH₂CH₂OCH₂CH₂— | OCH₃ |
| (332) | OC₂H₅ | OC₂H₅ | —CH₂CH₂OCH₂CH₂OCH₂CH₂— | OCH₃ |
| (333) | OC₂H₅ | OC₂H₅ | —CH₂CH₂— | NH₂ |
| (334) | OC₂H₅ | OC₂H₅ | —CH₂CH₂OCH₂CH₂— | NH₂ |
| (335) | OC₂H₅ | OC₂H₅ | —CH₂CH₂OCH₂CH₂OCH₂CH₂— | NH₂ |
| (336) | OC₂H₅ | OC₂H₅ | —CH₂CH₂— | Cl |
| (337) | OC₂H₅ | OC₂H₅ | —CH₂CH₂OCH₂CH₂— | Cl |
| (338) | OC₂H₅ | OC₂H₅ | —CH₂CH₂OCH₂CH₂OCH₂CH₂— | Cl |
| (339) | OC₂H₅ | OC₂H₅ | —CH₂CH₂— | N(CH₃)₂ |
| (340) | OC₂H₅ | OC₂H₅ | —CH₂CH₂OCH₂CH₂— | N(CH₃)₂ |
| (341) | OC₂H₅ | OC₂H₅ | —CH₂CH₂OCH₂CH₂OCH₂CH₂— | N(CH₃)₂ |
| (342) | OC₂H₅ | OC₂H₅ | —CH₂— | COOH |
| (343) | OC₂H₅ | OC₂H₅ | —CH₂CH₂OCH₂— | COOH |
| (344) | OC₂H₅ | OC₂H₅ | —CH₂CH₂OCH₂CH₂OCH₂— | COOH |
| (345) | OC₂H₅ | OC₂H₅ | —CH₂— | COOC₂H₅ |
| (346) | OC₂H₅ | OC₂H₅ | —CH₂CH₂OCH₂— | COOC₂H₅ |

-continued

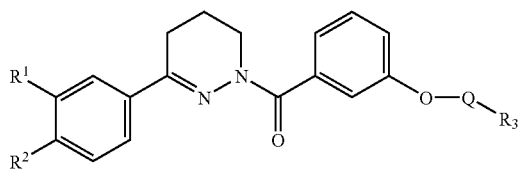

| | R¹ | R² | Q | R³ |
|---|---|---|---|---|
| (347) | OC₂H₅ | OC₂H₅ | —CH₂CH₂OCH₂CH₂OCH₂— | COOC₂H₅ |
| (348) | OC₂H₅ | OC₂H₅ | —CH₂CH₂— | OCO(CH₂)₆CH₃ |
| (349) | OC₂H₅ | OC₂H₅ | —CH₂CH₂OCH₂CH₂— | OCO(CH₂)₆CH₃ |
| (350) | OC₂H₅ | OC₂H₅ | —CH₂CH₂OCH₂CH₂OCH₂CH₂— | OCO(CH₂)₆CH₃ |
| (351) | OC₂H₅ | OC₂H₅ | —CH₂CH₂— | OCO(CH₂)₁₀CH₃ |
| (352) | OC₂H₅ | OC₂H₅ | —CH₂CH₂OCH₂CH₂— | OCO(CH₂)₁₀CH₃ |
| (353) | OC₂H₅ | OC₂H₅ | —CH₂CH₂OCH₂CH₂OCH₂CH₂— | OCO(CH₂)₁₀CH₃ |
| (354) | OC₂H₅ | OC₂H₅ | —CH₂CH₂— | —N(piperazine)NH |
| (355) | OC₂H₅ | OC₂H₅ | —CH₂CH₂OCH₂CH₂— | —N(piperazine)NH |
| (356) | OC₂H₅ | OC₂H₅ | —CH₂CH₂OCH₂CH₂OCH₂CH₂— | —N(piperazine)NH |
| (357) | OC₂H₅ | OC₂H₅ | —CH₂CH₂— | —N(piperazine)N-COOC₂H₅ |
| (358) | OC₂H₅ | OC₂H₅ | —CH₂CH₂OCH₂CH₂— | —N(piperazine)N-COOC₂H₅ |
| (359) | OC₂H₅ | OC₂H₅ | —CH₂CH₂OCH₂CH₂OCH₂CH₂— | —N(piperazine)N-COOC₂H₅ |
| (360) | OC₂H₅ | OC₂H₅ | —CH₂CH₂— | phthalimide |
| (361) | OC₂H₅ | OC₂H₅ | —CH₂CH₂OCH₂CH₂— | phthalimide |
| (362) | OC₂H₅ | OC₂H₅ | —CH₂CH₂OCH₂CH₂OCH₂CH₂— | phthalimide |

EXAMPLES 363-398

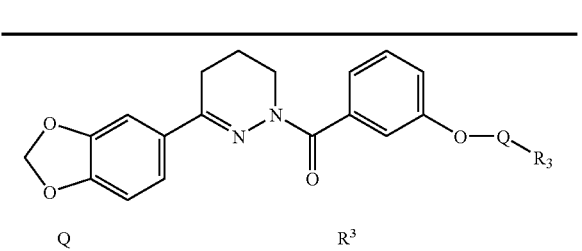

| | Q | R³ |
|---|---|---|
| (363) | —CH₂CH₂— | OH |
| (364) | —CH₂CH₂OCH₂CH₂— | OH |
| (365) | —CH₂CH₂OCH₂CH₂OCH₂CH₂— | OH |
| (366) | —CH₂CH₂— | OCH₃ |
| (367) | —CH₂CH₂OCH₂CH₂— | OCH₃ |
| (368) | —CH₂CH₂OCH₂CH₂OCH₂CH₂— | OCH₃ |
| (369) | —CH₂CH₂— | NH₂ |
| (370) | —CH₂CH₂OCH₂CH₂— | NH₂ |
| (371) | —CH₂CH₂OCH₂CH₂OCH₂CH₂— | NH₂ |
| (372) | —CH₂CH₂— | Cl |
| (373) | —CH₂CH₂OCH₂CH₂— | Cl |
| (374) | —CH₂CH₂OCH₂CH₂OCH₂CH₂— | Cl |
| (375) | —CH₂CH₂— | N(CH₃)₂ |
| (376) | —CH₂CH₂OCH₂CH₂— | N(CH₃)₂ |
| (377) | —CH₂CH₂OCH₂CH₂OCH₂CH₂— | N(CH₃)₂ |
| (378) | —CH₂— | COOH |
| (379) | —CH₂CH₂OCH₂— | COOH |
| (380) | —CH₂CH₂OCH₂CH₂OCH₂— | COOH |
| (381) | —CH₂— | COOC₂H₅ |
| (382) | —CH₂CH₂OCH₂— | COOC₂H₅ |
| (383) | —CH₂CH₂OCH₂CH₂OCH₂— | COOC₂H₅ |
| (384) | —CH₂CH₂— | OCO(CH₂)₆CH₃ |
| (385) | —CH₂CH₂OCH₂CH₂— | OCO(CH₂)₆CH₃ |
| (386) | —CH₂CH₂OCH₂CH₂OCH₂CH₂— | OCO(CH₂)₆CH₃ |
| (387) | —CH₂CH₂— | OCO(CH₂)₁₀CH₃ |
| (388) | —CH₂CH₂OCH₂CH₂— | OCO(CH₂)₁₀CH₃ |
| (389) | —CH₂CH₂OCH₂CH₂OCH₂CH₂— | OCO(CH₂)₁₀CH₃ |

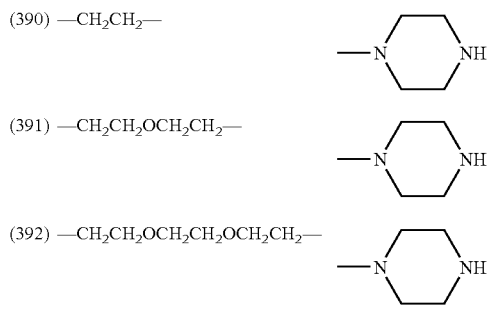

(390) —CH₂CH₂—

(391) —CH₂CH₂OCH₂CH₂—

(392) —CH₂CH₂OCH₂CH₂OCH₂CH₂—

-continued

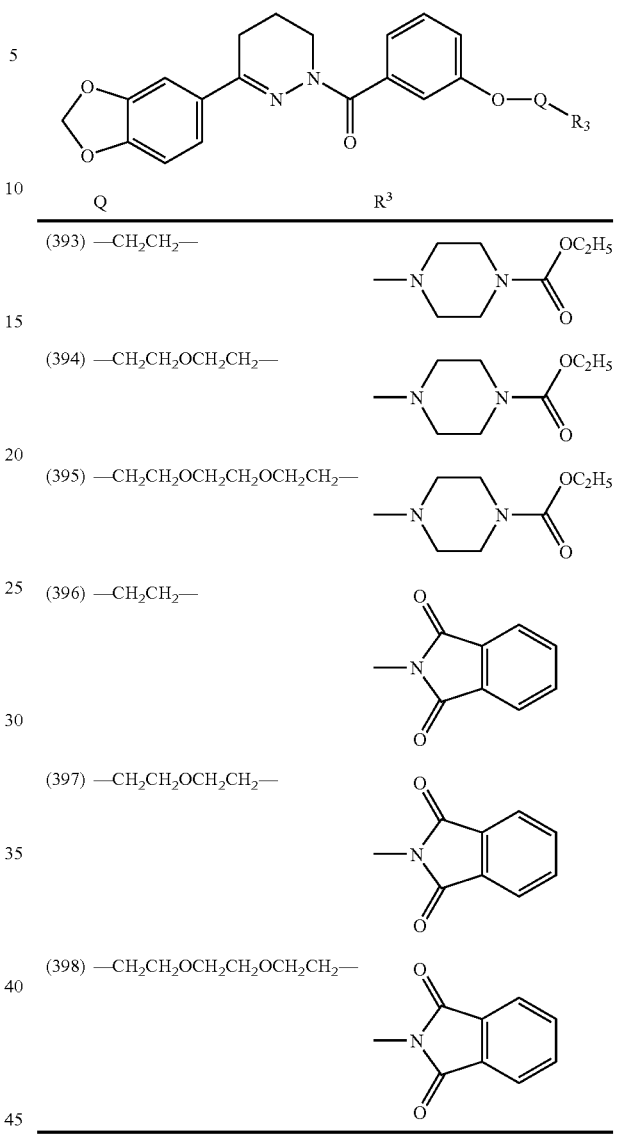

| | Q | R³ |
|---|---|---|
| (393) | —CH₂CH₂— | (piperazine-N-COOC₂H₅) |
| (394) | —CH₂CH₂OCH₂CH₂— | (piperazine-N-COOC₂H₅) |
| (395) | —CH₂CH₂OCH₂CH₂OCH₂CH₂— | (piperazine-N-COOC₂H₅) |
| (396) | —CH₂CH₂— | (phthalimido) |
| (397) | —CH₂CH₂OCH₂CH₂— | (phthalimido) |
| (398) | —CH₂CH₂OCH₂CH₂OCH₂CH₂— | (phthalimido) |

EXAMPLES 399-506

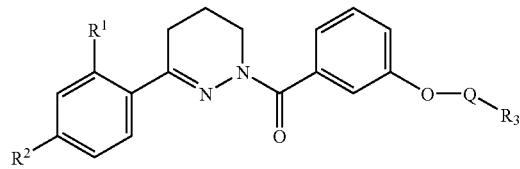

| | R¹ | R² | Q | R³ |
|---|---|---|---|---|
| (399) | OC₂H₅ | OCH₃ | —CH₂CH₂— | OH |
| (400) | OC₂H₅ | OCH₃ | —CH₂CH₂OCH₂CH₂— | OH |
| (401) | OC₂H₅ | OCH₃ | —CH₂CH₂OCH₂CH₂OCH₂CH₂— | OH |
| (402) | OC₂H₅ | OCH₃ | —CH₂CH₂— | OCH₃ |
| (403) | OC₂H₅ | OCH₃ | —CH₂CH₂OCH₂CH₂— | OCH₃ |
| (404) | OC₂H₅ | OCH₃ | —CH₂CH₂OCH₂CH₂OCH₂CH₂— | OCH₃ |

-continued

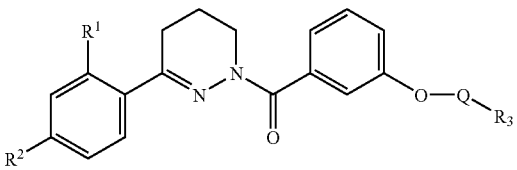

| | R¹ | R² | Q | R³ |
|---|---|---|---|---|
| (405) | OC₂H₅ | OCH₃ | —CH₂CH₂— | NH₂ |
| (406) | OC₂H₅ | OCH₃ | —CH₂CH₂OCH₂CH₂— | NH₂ |
| (407) | OC₂H₅ | OCH₃ | —CH₂CH₂OCH₂CH₂OCH₂CH₂— | NH₂ |
| (408) | OC₂H₅ | OCH₃ | —CH₂CH₂— | Cl |
| (409) | OC₂H₅ | OCH₃ | —CH₂CH₂OCH₂CH₂— | Cl |
| (410) | OC₂H₅ | OCH₃ | —CH₂CH₂OCH₂CH₂OCH₂CH₂— | Cl |
| (411) | OC₂H₅ | OCH₃ | —CH₂CH₂— | N(CH₃)₂ |
| (412) | OC₂H₅ | OCH₃ | —CH₂CH₂OCH₂CH₂— | N(CH₃)₂ |
| (413) | OC₂H₅ | OCH₃ | —CH₂CH₂OCH₂CH₂OCH₂CH₂— | N(CH₃)₂ |
| (414) | OC₂H₅ | OCH₃ | —CH₂— | COOH |
| (415) | OC₂H₅ | OCH₃ | —CH₂CH₂OCH₂— | COOH |
| (416) | OC₂H₅ | OCH₃ | —CH₂CH₂OCH₂CH₂OCH— | COOH |
| (417) | OC₂H₅ | OCH₃ | —CH₂— | COOC₂H₅ |
| (418) | OC₂H₅ | OCH₃ | —CH₂CH₂OCH₂— | COOC₂H₅ |
| (419) | OC₂H₅ | OCH₃ | —CH₂CH₂OCH₂CH₂OCH— | COOC₂H₅ |
| (420) | OC₂H₅ | OCH₃ | —CH₂CH₂— | OCO(CH₂)₆CH₃ |
| (421) | OC₂H₅ | OCH₃ | —CH₂CH₂OCH₂CH₂— | OCO(CH₂)₆CH₃ |
| (422) | OC₂H₅ | OCH₃ | —CH₂CH₂OCH₂CH₂OCH₂CH₂— | OCO(CH₂)₆CH₃ |
| (423) | OC₂H₅ | OCH₃ | —CH₂CH₂— | OCO(CH₂)₁₀CH₃ |
| (424) | OC₂H₅ | OCH₃ | —CH₂CH₂OCH₂CH₂— | OCO(CH₂)₁₀CH₃ |
| (425) | OC₂H₅ | OCH₃ | —CH₂CH₂OCH₂CH₂OCH₂CH₂— | OCO(CH₂)₁₀CH₃ |
| (426) | OC₂H₅ | OCH₃ | —CH₂CH₂— | 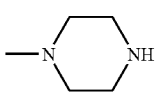 |
| (427) | OC₂H₅ | OCH₃ | —CH₂CH₂OCH₂CH₂— | 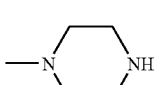 |
| (428) | OC₂H₅ | OCH₃ | —CH₂CH₂OCH₂CH₂OCH₂CH₂— | 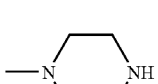 |
| (429) | OC₂H₅ | OCH₃ | —CH₂CH₂— | 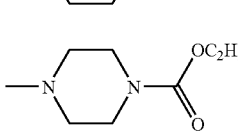 |
| (430) | OC₂H₅ | OCH₃ | —CH₂CH₂OCH₂CH₂— | 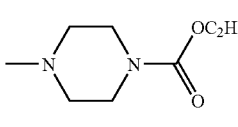 |
| (431) | OC₂H₅ | OCH₃ | —CH₂CH₂OCH₂CH₂OCH₂CH₂— | 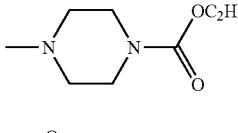 |
| (432) | OC₂H₅ | OCH₃ | —CH₂CH₂— | 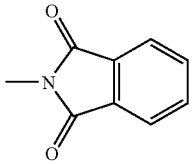 |

-continued

| R¹ | R² | Q | R³ |
|---|---|---|---|
| (433) OC₂H₅ | OCH₃ | —CH₂CH₂OCH₂CH₂— | N-phthalimide |
| (434) OC₂H₅ | OCH₃ | —CH₂CH₂OCH₂CH₂OCH₂CH₂— | N-phthalimide |
| (435) OCH₃ | OCH₃ | —CH₂CH₂— | OH |
| (436) OCH₃ | OCH₃ | —CH₂CH₂OCH₂CH₂— | OH |
| (437) OCH₃ | OCH₃ | —CH₂CH₂OCH₂CH₂OCH₂CH₂— | OH |
| (438) OCH₃ | OCH₃ | —CH₂CH₂— | OCH₃ |
| (439) OCH₃ | OCH₃ | —CH₂CH₂OCH₂CH₂— | OCH₃ |
| (440) OCH₃ | OCH₃ | —CH₂CH₂OCH₂CH₂OCH₂CH₂— | OCH₃ |
| (441) OCH₃ | OCH₃ | —CH₂CH₂— | NH₂ |
| (442) OCH₃ | OCH₃ | —CH₂CH₂OCH₂CH₂— | NH₂ |
| (443) OCH₃ | OCH₃ | —CH₂CH₂OCH₂CH₂OCH₂CH₂— | NH₂ |
| (444) OCH₃ | OCH₃ | —CH₂CH₂— | Cl |
| (445) OCH₃ | OCH₃ | —CH₂CH₂OCH₂CH₂— | Cl |
| (446) OCH₃ | OCH₃ | —CH₂CH₂OCH₂CH₂OCH₂CH₂— | Cl |
| (447) OCH₃ | OCH₃ | —CH₂CH₂— | N(CH₃)₂ |
| (448) OCH₃ | OCH₃ | —CH₂CH₂OCH₂CH₂— | N(CH₃)₂ |
| (449) OCH₃ | OCH₃ | —CH₂CH₂OCH₂CH₂OCH₂CH₂— | N(CH₃)₂ |
| (450) OCH₃ | OCH₃ | —CH₂— | COOH |
| (451) OCH₃ | OCH₃ | —CH₂CH₂OCH₂— | COOH |
| (452) OCH₃ | OCH₃ | —CH₂CH₂OCH₂CH₂OCH₂— | COOH |
| (453) OCH₃ | OCH₃ | —CH₂— | COOC₂H₅ |
| (454) OCH₃ | OCH₃ | —CH₂CH₂OCH₂— | COOC₂H₅ |
| (455) OCH₃ | OCH₃ | —CH₂CH₂OCH₂CH₂OCH₂— | COOC₂H₅ |
| (456) OCH₃ | OCH₃ | —CH₂CH₂— | OCO(CH₂)₆CH₃ |
| (457) OCH₃ | OCH₃ | —CH₂CH₂OCH₂CH₂— | OCO(CH₂)₆CH₃ |
| (458) OCH₃ | OCH₃ | —CH₂CH₂OCH₂CH₂OCH₂CH₂— | OCO(CH₂)₆CH₃ |
| (459) OCH₃ | OCH₃ | —CH₂CH₂— | OCO(CH₂)₁₀CH₃ |
| (460) OCH₃ | OCH₃ | —CH₂CH₂OCH₂CH₂— | OCO(CH₂)₁₀CH₃ |
| (461) OCH₃ | OCH₃ | —CH₂CH₂OCH₂CH₂OCH₂CH₂— | OCO(CH₂)₁₀CH₃ |
| (462) OCH₃ | OCH₃ | —CH₂CH₂— | piperazinyl |
| (463) OCH₃ | OCH₃ | —CH₂CH₂OCH₂CH₂— | piperazinyl |
| (464) OCH₃ | OCH₃ | —CH₂CH₂OCH₂CH₂OCH₂CH₂— | piperazinyl |
| (465) OCH₃ | OCH₃ | —CH₂CH₂— | 4-(ethoxycarbonyl)piperazin-1-yl |

-continued

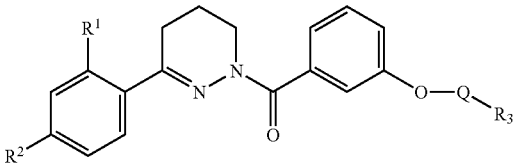

| | R¹ | R² | Q | R³ |
|---|---|---|---|---|
| (466) | OCH₃ | OCH₃ | —CH₂CH₂OCH₂CH₂— | 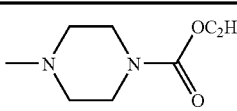 |
| (467) | OCH₃ | OCH₃ | —CH₂CH₂OCH₂CH₂OCH₂CH₂— | 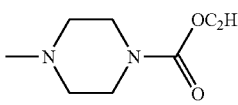 |
| (468) | OCH₃ | OCH₃ | —CH₂CH₂— | 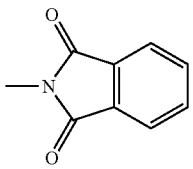 |
| (469) | OCH₃ | OCH₃ | —CH₂CH₂OCH₂CH₂— | 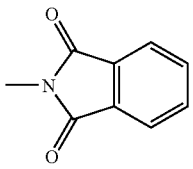 |
| (470) | OCH₃ | OCH₃ | —CH₂CH₂OCH₂CH₂OCH₂CH₂— | 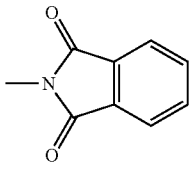 |
| (471) | OC₂H₅ | OC₂H₅ | —CH₂CH₂— | OH |
| (472) | OC₂H₅ | OC₂H₅ | —CH₂CH₂OCH₂CH₂— | OH |
| (473) | OC₂H₅ | OC₂H₅ | —CH₂CH₂OCH₂CH₂OCH₂CH₂— | OH |
| (474) | OC₂H₅ | OC₂H₅ | —CH₂CH₂— | OCH₃ |
| (475) | OC₂H₅ | OC₂H₅ | —CH₂CH₂OCH₂CH₂— | OCH₃ |
| (476) | OC₂H₅ | OC₂H₅ | —CH₂CH₂OCH₂CH₂OCH₂CH₂— | OCH₃ |
| (477) | OC₂H₅ | OC₂H₅ | —CH₂CH₂— | NH₂ |
| (478) | OC₂H₅ | OC₂H₅ | —CH₂CH₂OCH₂CH₂— | NH₂ |
| (479) | OC₂H₅ | OC₂H₅ | —CH₂CH₂OCH₂CH₂OCH₂CH₂— | NH₂ |
| (480) | OC₂H₅ | OC₂H₅ | —CH₂CH₂— | Cl |
| (481) | OC₂H₅ | OC₂H₅ | —CH₂CH₂OCH₂CH₂— | Cl |
| (482) | OC₂H₅ | OC₂H₅ | —CH₂CH₂OCH₂CH₂OCH₂CH₂— | Cl |
| (483) | OC₂H₅ | OC₂H₅ | —CH₂CH₂— | N(CH₃)₂ |
| (484) | OC₂H₅ | OC₂H₅ | —CH₂CH₂OCH₂CH₂— | N(CH₃)₂ |
| (485) | OC₂H₅ | OC₂H₅ | —CH₂CH₂OCH₂CH₂OCH₂CH₂— | N(CH₃)₂ |
| (486) | OC₂H₅ | OC₂H₅ | —CH₂— | COOH |
| (487) | OC₂H₅ | OC₂H₅ | —CH₂CH₂OCH₂— | COOH |
| (488) | OC₂H₅ | OC₂H₅ | —CH₂CH₂OCH₂CH₂OCH₂— | COOH |
| (489) | OC₂H₅ | OC₂H₅ | —CH₂— | COOC₂H₅ |
| (490) | OC₂H₅ | OC₂H₅ | —CH₂CH₂OCH₂— | COOC₂H₅ |
| (491) | OC₂H₅ | OC₂H₅ | —CH₂CH₂OCH₂CH₂OCH₂— | COOC₂H₅ |
| (492) | OC₂H₅ | OC₂H₅ | —CH₂CH₂— | OCO(CH₂)₆CH₃ |
| (493) | OC₂H₅ | OC₂H₅ | —CH₂CH₂OCH₂CH₂— | OCO(CH₂)₆CH₃ |
| (494) | OC₂H₅ | OC₂H₅ | —CH₂CH₂OCH₂CH₂OCH₂CH₂— | OCO(CH₂)₆CH₃ |
| (495) | OC₂H₅ | OC₂H₅ | —CH₂CH₂— | OCO(CH₂)₁₀CH₃ |
| (496) | OC₂H₅ | OC₂H₅ | —CH₂CH₂OCH₂CH₂— | OCO(CH₂)₁₀CH₃ |
| (497) | OC₂H₅ | OC₂H₅ | —CH₂CH₂OCH₂CH₂OCH₂CH₂— | OCO(CH₂)₁₀CH₃ |

-continued
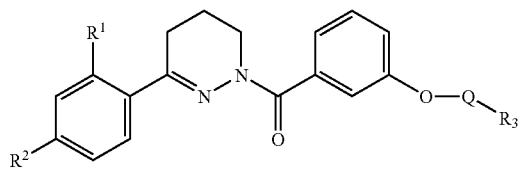
| | R¹ | R² | Q | R³ |
|---|---|---|---|---|
| (498) | OC₂H₅ | OC₂H₅ | —CH₂CH₂— | 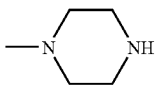 |
| (499) | OC₂H₅ | OC₂H₅ | —CH₂CH₂OCH₂CH₂— | 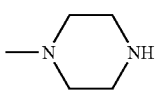 |
| (500) | OC₂H₅ | OC₂H₅ | —CH₂CH₂OCH₂CH₂OCH₂CH₂— | 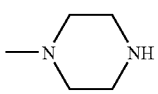 |
| (501) | OC₂H₅ | OC₂H₅ | —CH₂CH₂— | 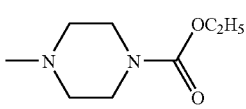 |
| (502) | OC₂H₅ | OC₂H₅ | —CH₂CH₂OCH₂CH₂— | 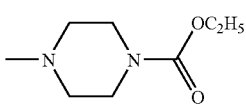 |
| (503) | OC₂H₅ | OC₂H₅ | —CH₂CH₂OCH₂CH₂OCH₂CH₂— | 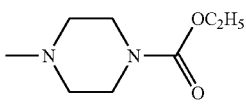 |
| (504) | OC₂H₅ | OC₂H₅ | —CH₂CH₂— | 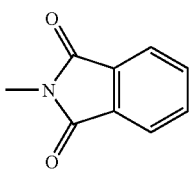 |
| (505) | OC₂H₅ | OC₂H₅ | —CH₂CH₂OCH₂CH₂— | 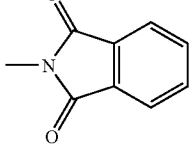 |
| (506) | OC₂H₅ | OC₂H₅ | —CH₂CH₂OCH₂CH₂OCH₂CH₂— | 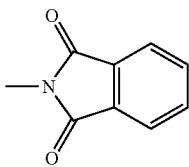 |

The examples below relate to pharmaceutical preparations:

EXAMPLE A

Injection Vials

A solution of 100 g of an active ingredient of the formula I and 5 g of disodium hydrogenphosphate in 3 l of bidistilled water is adjusted to pH 6.5 using 2N hydrochloric acid, sterile filtered, transferred into injection vials, lyophilised under sterile conditions and sealed under sterile conditions. Each injection vial contains 5 mg of active ingredient.

EXAMPLE B

Suppositories

A mixture of 20 g of an active ingredient of the formula I is melted with 100 g of soya lecithin and 1400 g of cocoa butter, poured into moulds and allowed to cool. Each suppository contains 20 mg of active ingredient.

EXAMPLE C

Solution

A solution is prepared from 1 g of an active ingredient of the formula I, 9.38 g of $NaH_2PO_4.2H_2O$, 28.48 g of $Na_2HPO_4.12H_2O$ and 0.1 g of benzalkonium chloride in 940 ml of bidistilled water. The pH is adjusted to 6.8, and the solution is made up to 1 l and sterilised by irradiation. This solution can be used in the form of eye drops.

EXAMPLE D

Ointment 500 mg of an active ingredient of the formula I are mixed with 99.5 g of Vaseline under aseptic conditions.

EXAMPLE E

Tablets

A mixture of 1 kg of active ingredient of the formula I, 4 kg of lactose, 1.2 kg of potato starch, 0.2 kg of talc and 0.1 kg of magnesium stearate is pressed in a conventional manner to give tablets in such a way that each tablet contains 10 mg of active ingredient.

EXAMPLE F

Coated Tablets

Tablets are pressed analogously to Example E and subsequently coated in a conventional manner with a coating of sucrose, potato starch, talc, tragacanth and dye.

EXAMPLE G

Capsules 2 kg of active ingredient of the formula I are introduced in a conventional manner into hard gelatine capsules in such a way that each capsule contains 20 mg of the active ingredient.

EXAMPLE H

Ampoules

A solution of 1 kg of active ingredient of the formula I in 60 l of bidistilled water is sterile filtered, transferred into ampoules, lyophilised under sterile conditions and sealed under sterile conditions. Each ampoule contains 10 mg of active ingredient.

EXAMPLE I

Inhalation Spray 14 g of active ingredient of the formula I are dissolved in 10 l of isotonic NaCl solution, and the solution is transferred into commercially available spray containers with pump mechanism. The solution can be sprayed into the mouth or nose. One spray shot (about 0.1 ml) corresponds to a dose of about 0.14 mg.

The invention claimed is:

1. Compounds of the formula I

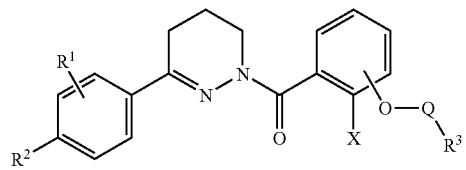

in which $R^1$ and $R^2$ are each, independently of one another, H, OH, $OR^4$, $SR^4$, $SOR^4$, $SO_2R^4$ or Hal, where $R^1$ and $R^2$ together may alternatively be —O—$CH_2$—O—, $R^3$ is Hal, OH, OA, NO2, NH2, $NHA^1$, $NA^1A^2$, CN, COOH, $COOA^1$, $CONH_2$, $CONHA^1$, $CONA^1A^2$, $NHCOA^1$, $NHSO_2A^1$, $NHCOOA^1$, $R^4$ is $A^1$, cycloalkyl having from 3 to 7 carbon atoms, alkylene cycloalkyl having from 4 to 8 carbon atoms or alkenyl having from 2 to 8 carbon atoms, $A^1$ and $A^2$ are each, independently of one another, alkyl having from 1 to 12 carbon atoms, which may be substituted by from 1 to 5 F and/or Cl atoms or OH-groups, where $A^1$ and $A^2$ together may alternatively be cycloalkyl or cycloalkylene having from 3 to 7 ring members, in which one or more $CH_2$ groups may be replaced by —S—, —O—, —NH—, —$NA^1$-, —$NCOA^1$- or —$NCOOA^1$-, X is H or Hal, Hal is F, Cl, Br or I and Q is alkyl or alkenyl having from 1 to 15 carbon atoms, in which from 1 to 5 —$CH_2$— groups may be replaced by —O—, —S—, —SO2—, —CH(Hal)-, —C(Hal)2-, —$CHA^1$-, —$CA^1A^2$-, —NH— or —$NA^1$-, and salts thereof.

2. A compounds of formula I according to claim 1, wherein $R^1$ and $R^2$ are each, independently of one another, methoxy, ethoxy, propoxy, cyclopentoxy, fluoro-, difluoro- or trifluoromethoxy, or 1-fluoro-, 2-fluoro-, 1,2-difluoro-, 2,2-difluoro-, 1,2,2-trifluoro- or 2,2,2-trifluoroethoxy.

3. A compound of formula I according to claim 1, wherein $A^1$ and $A^2$ are each, independently of one another, alkyl having from 1 to 12 carbon atoms, alkyl having from 1 to 10 carbon atoms which is substituted by from 1 to 5 fluorine and/or chlorine atoms, or together are alternatively cycloalkyl having from 3 to 7 carbon atoms.

4. A compound of formula I according to claim 1, wherein Q is alkylene having from 1 to 10 carbon atoms, in which from 1 to 3 carbon atoms may be replaced by —O—, —NH— or —NA$^1$-, and A$^1$ is as defined in claim 1.

5. A compound of formula I according to claim 1, wherein R$^3$ is preferably A$^1$, F, Cl, Br or I, hydroxyl, NH2, O-alkyl, NO2, alkylamino, cycloalkylamino, or dialkylamino, where alkyl has from I to 10 carbon atoms and cycloalkyl has from 3 to 7 carbon atoms, and A$^1$ is as defined in claim 1.

6. A compound of formulae 11 to 174 according to claim 1:

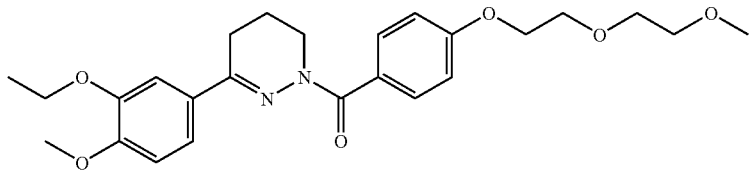

I1

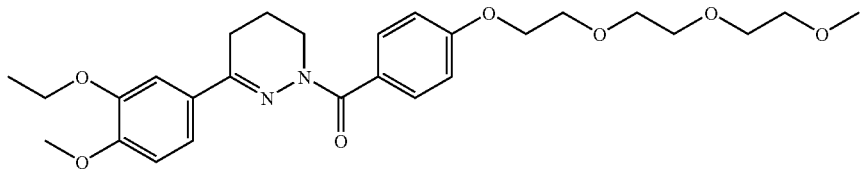

I3

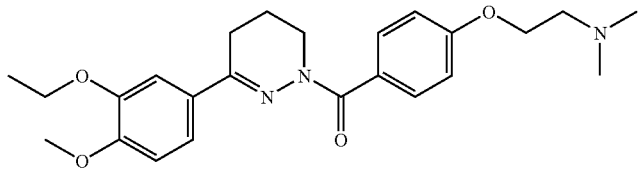

I5

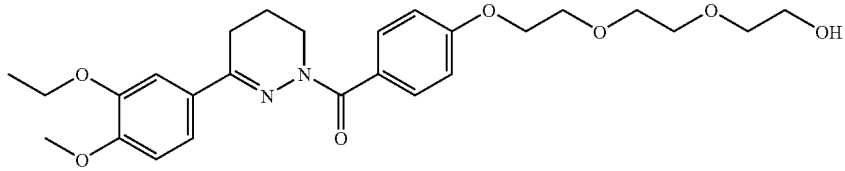

I7

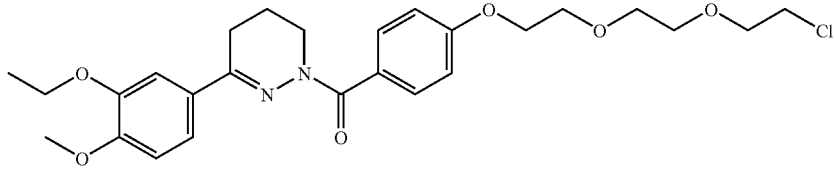

I8

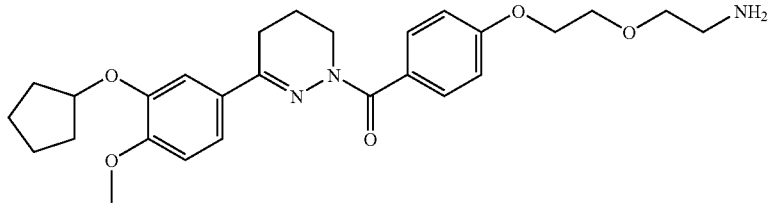

I10

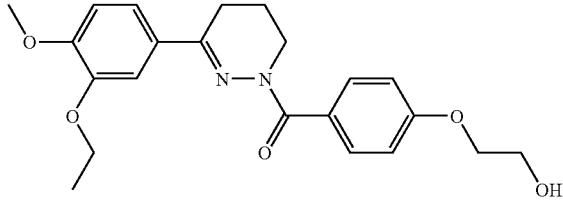

I11

-continued
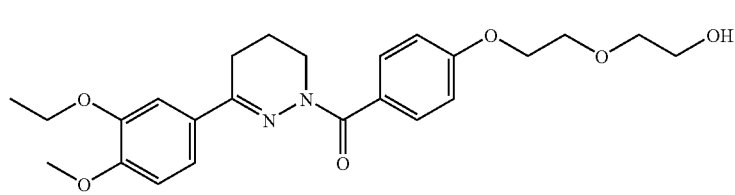
I12
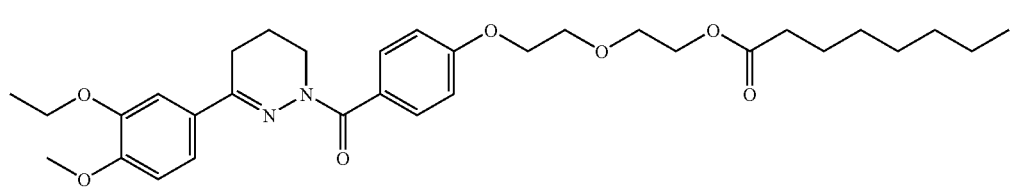
I13
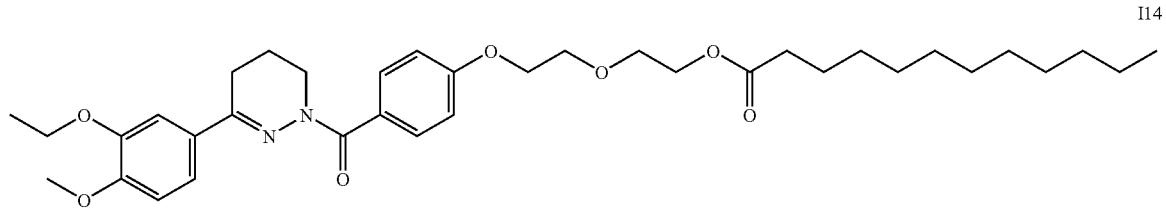
I14
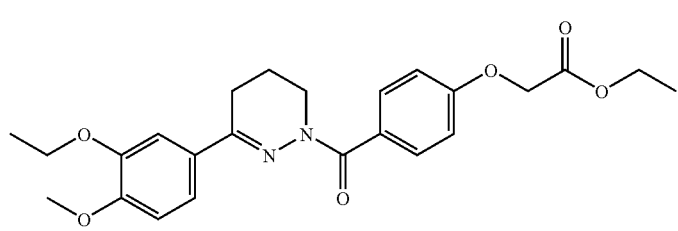
I16
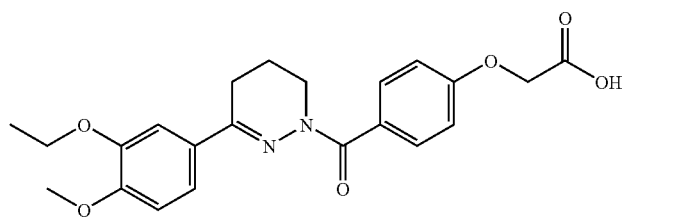
I17
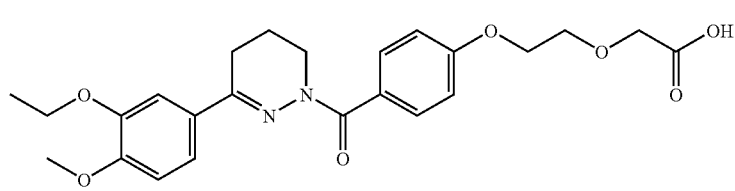
I18
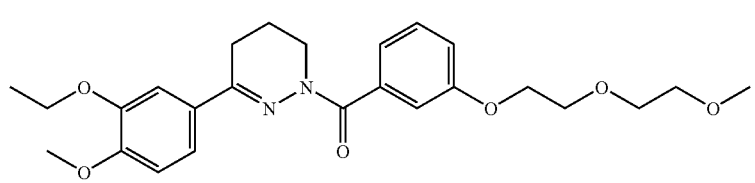
I19
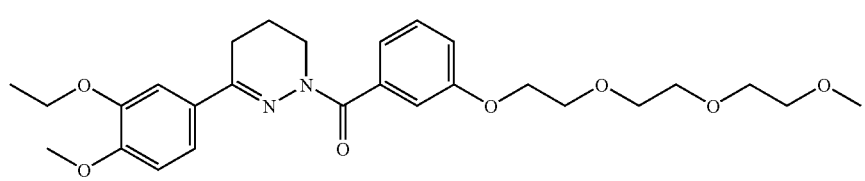
I20

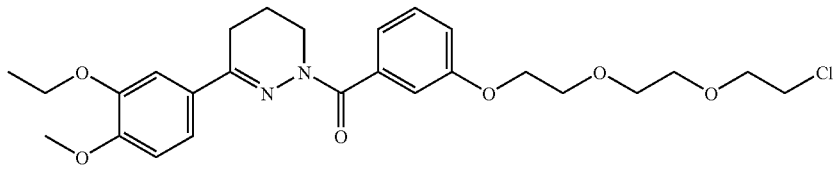 I21
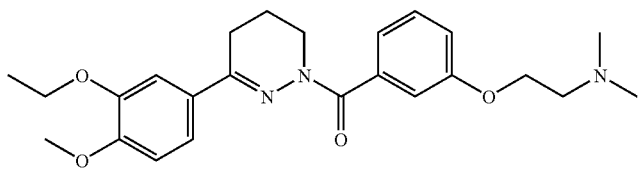 I23
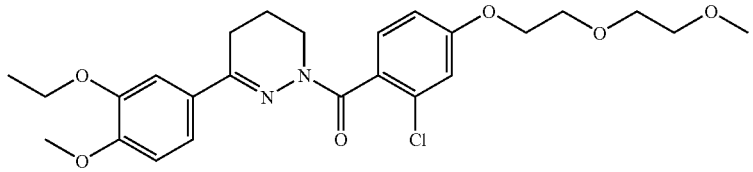 I25
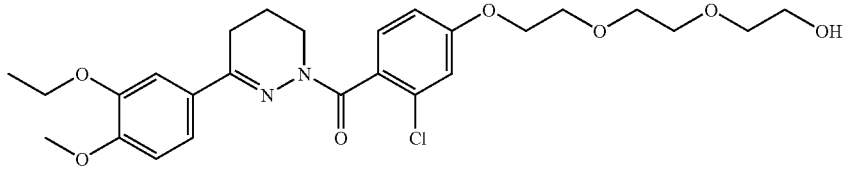 I26
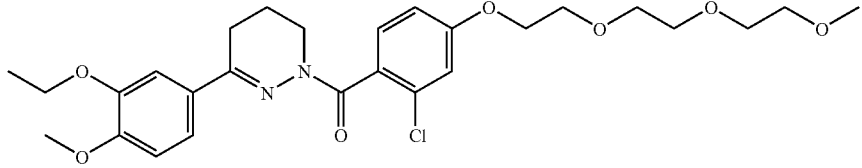 I27
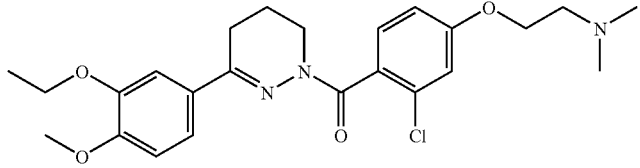 I28
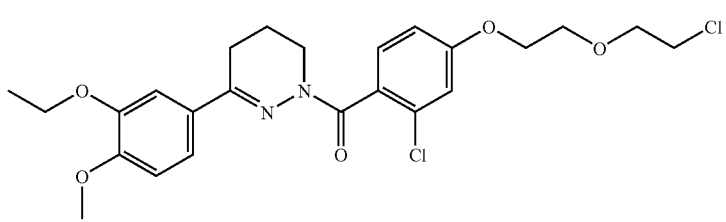 I30
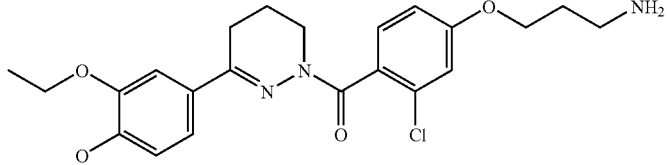 I31

-continued
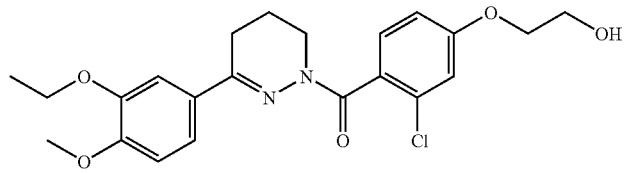
I32
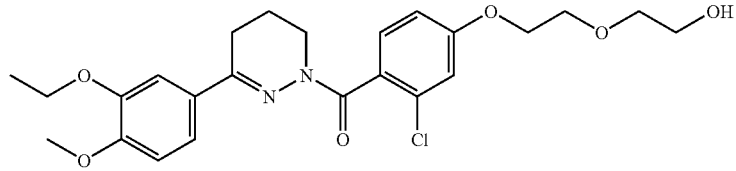
I33
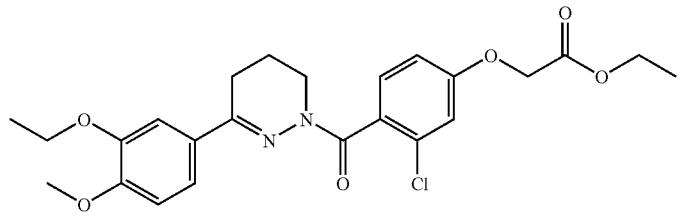
I36
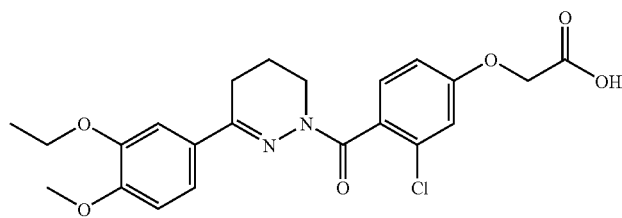
I37
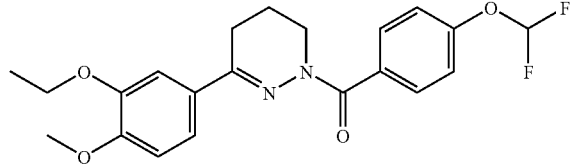
I41
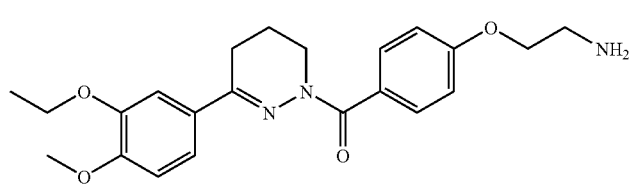
I42
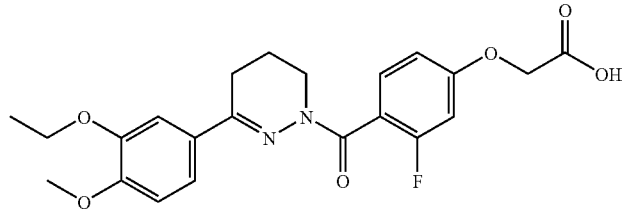
I43
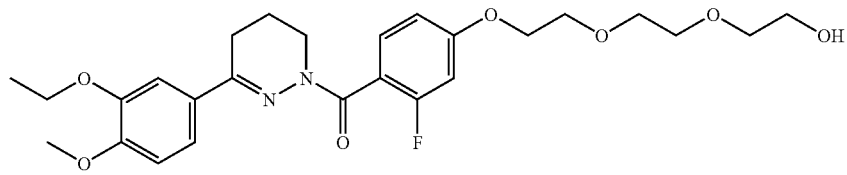
I44

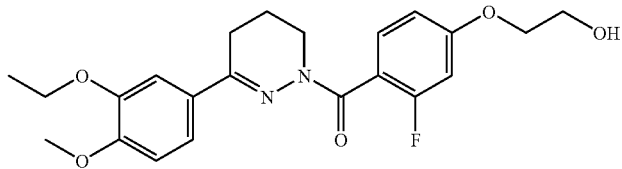
I45
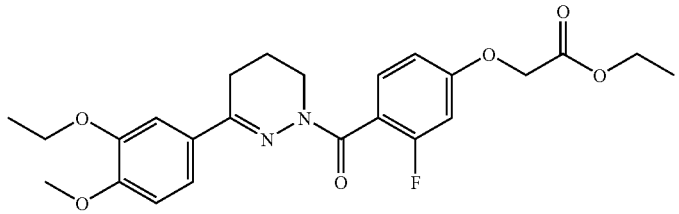
I46
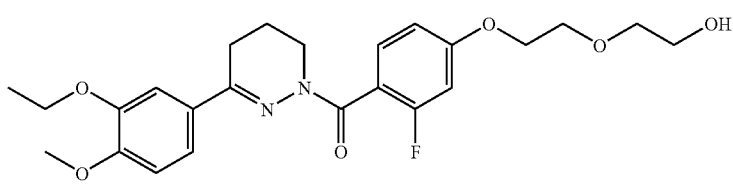
I47
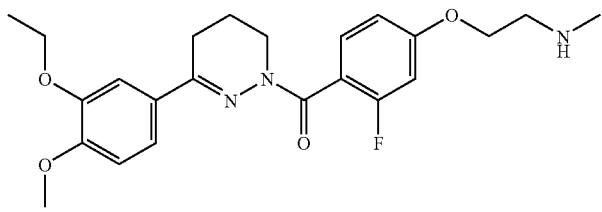
I48
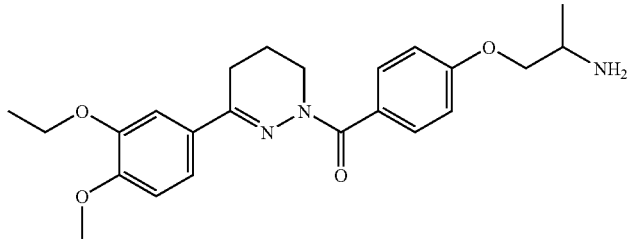
I49
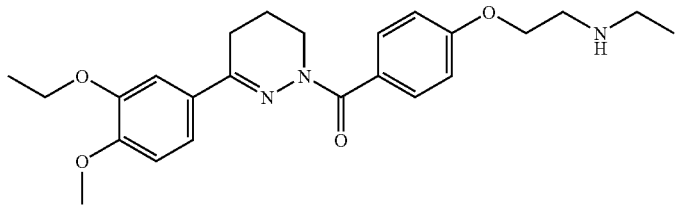
I50
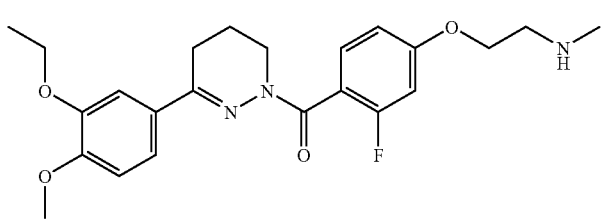
I52

-continued
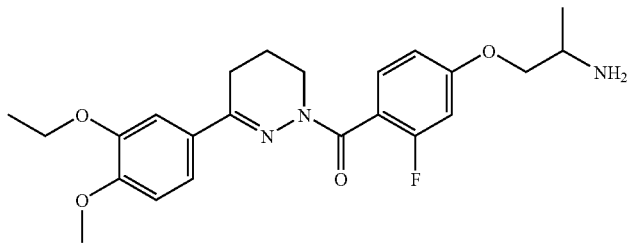
I53
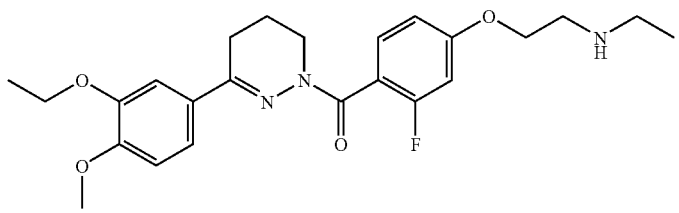
I54
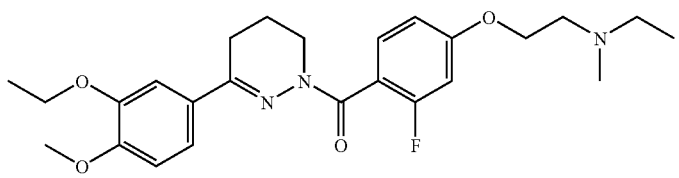
I55
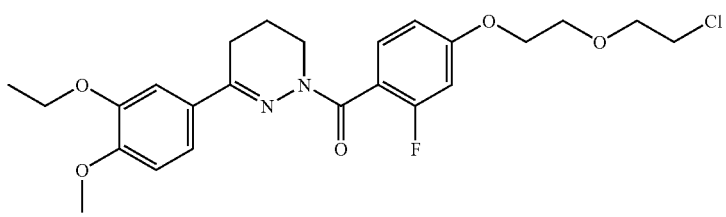
I57
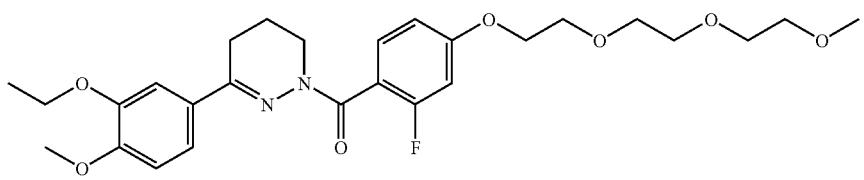
I58
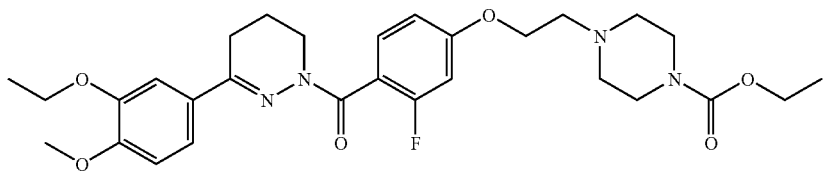
I60
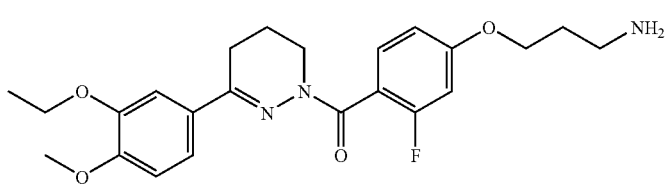
I62
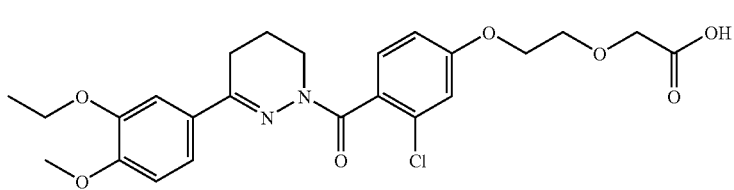
I63

-continued
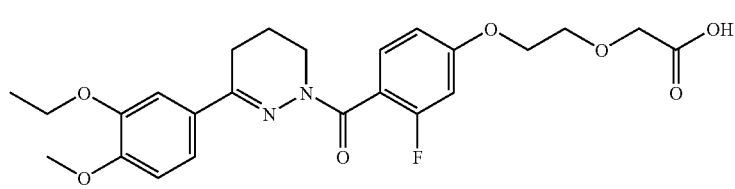
I64
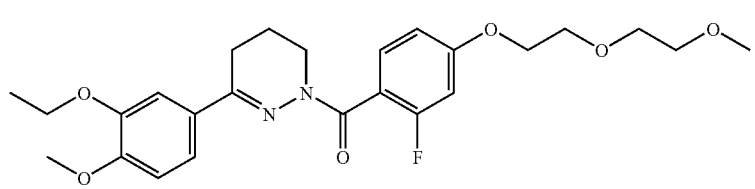
I65
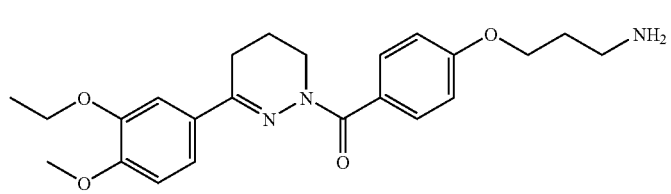
I66
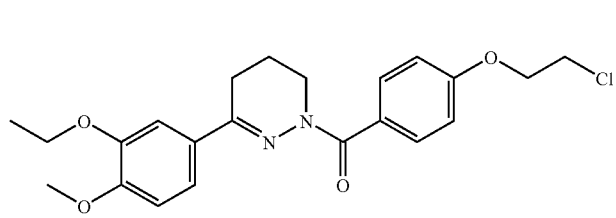
I69
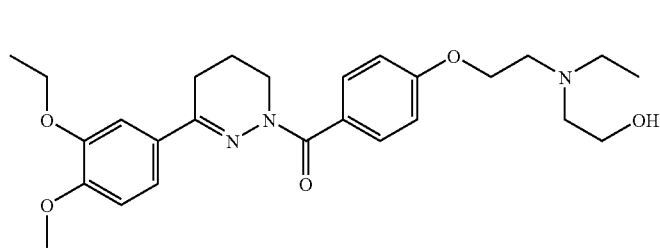
I73
or a salt or solvate thereof.
7. A compound of formula II
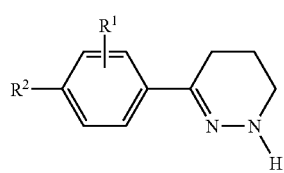
II
in which $R^1$ and $R^2$ are as defined in claim 1.
8. A compound of the formula IV
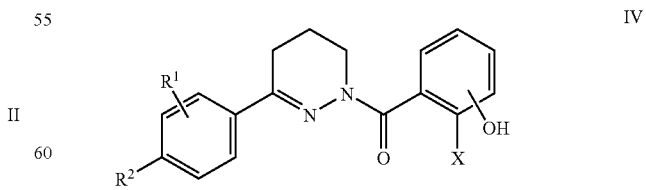
IV
in which X, $R^1$ and $R^2$ are as defined in claim 1.
9. A process for preparation of a compound of the formula I or a salt thereof, comprising reacting a compound of the formula II

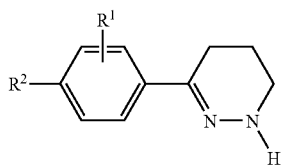

in which
R¹ and R² are as defined in claim 1,
with a compound of the formula III

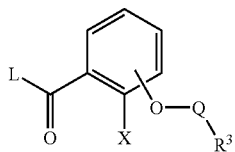

in which
R³ and Q are as defined in claim 1, and
L is Cl, Br, OH or a reactive esterified OH group, or
reacting a compound of the formula IV

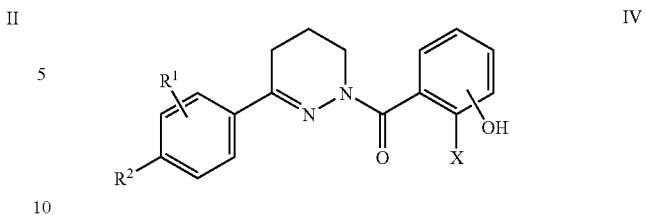

in which X, R¹ and R² are as defined in claim

L-Q-R³   V

1, with a compound of the formula V
in which
Q and R³ are as defined in claim 1, and
L is Cl, Br, OH or a reactive esterified OH group,
and/or converting a basic compound of the formula I into one of its salts by treatment with an acid.

10. A method for the preparation of a medicament, comprising combining a compound of the formula I according to claim 1 and/or a physiologically acceptable salt thereof with a pharmaceutically acceptable carrier.

11. A pharmaceutical composition, comprising at least one compound of the formula I according to claim 1 and/or one of its physiologically acceptable salts thereof.

* * * * *